US011814425B2

(12) United States Patent
Rotello et al.

(10) Patent No.: US 11,814,425 B2
(45) Date of Patent: *Nov. 14, 2023

(54) ANTIBODIES THAT BIND HUMAN PROTEIN TYROSINE PHOSPHATASE BETA (HPTPBETA) AND USES THEREOF

(71) Applicant: EyePoint Pharmaceuticals, Inc., Watertown, MA (US)

(72) Inventors: Rocco Jamie Rotello, Lebanon, OH (US); Kevin Gene Peters, Cincinnati, OH (US); Michael Glenn Davis, Lebanon, OH (US)

(73) Assignee: Eye Point Pharmaceuticals, Inc., Watertown, MA (US)

( * ) Notice: Subject to any disclaimer, the term of this patent is extended or adjusted under 35 U.S.C. 154(b) by 328 days.

This patent is subject to a terminal disclaimer.

(21) Appl. No.: 16/784,970

(22) Filed: Feb. 7, 2020

(65) Prior Publication Data

US 2020/0407430 A1 Dec. 31, 2020

Related U.S. Application Data

(60) Continuation of application No. 16/696,212, filed on Nov. 26, 2019, now abandoned, which is a continuation of application No. 15/894,442, filed on Feb. 12, 2018, now abandoned, which is a continuation of application No. 15/430,100, filed on Feb. 10, 2017, now Pat. No. 9,926,367, which is a continuation of application No. 13/958,990, filed on Aug. 5, 2013, now abandoned, which is a division of application No. 13/115,180, filed on May 25, 2011, now Pat. No. 8,524,235, which is a division of application No. 11/784,094, filed on Apr. 5, 2007, now Pat. No. 7,973,142.

(60) Provisional application No. 60/798,896, filed on May 9, 2006, provisional application No. 60/790,506, filed on Apr. 7, 2006.

(51) Int. Cl.
| C07K 16/18 | (2006.01) |
| C07K 16/28 | (2006.01) |
| C07K 16/40 | (2006.01) |
| A61K 39/00 | (2006.01) |

(52) U.S. Cl.
CPC .............. *C07K 16/18* (2013.01); *C07K 16/28* (2013.01); *C07K 16/40* (2013.01); *A61K 2039/505* (2013.01); *C07K 2317/55* (2013.01); *C07K 2317/73* (2013.01); *C07K 2317/75* (2013.01); *C07K 2317/76* (2013.01)

(58) Field of Classification Search
None
See application file for complete search history.

(56) References Cited

U.S. PATENT DOCUMENTS

| 4,179,337 A | 12/1979 | Davis et al. |
| 4,301,144 A | 11/1981 | Iwasaki et al. |
| 4,399,216 A | 8/1983 | Axel et al. |
| 4,496,689 A | 1/1985 | Mitra |
| 4,522,811 A | 6/1985 | Eppstein et al. |
| 4,640,835 A | 2/1987 | Shimizu et al. |
| 4,670,417 A | 6/1987 | Iwasaki et al. |
| 4,673,641 A | 6/1987 | George et al. |
| 4,740,461 A | 4/1988 | Kaufman |
| 4,791,192 A | 12/1988 | Nakagawa et al. |
| 4,816,567 A | 3/1989 | Cabilly et al. |
| 4,912,040 A | 3/1990 | Kaufman et al. |
| 4,959,455 A | 9/1990 | Clark et al. |
| 5,225,539 A | 7/1993 | Winter |
| 5,424,398 A | 6/1995 | Middeldorp et al. |
| 5,545,806 A | 8/1996 | Lonberg et al. |
| 5,545,807 A | 8/1996 | Surani et al. |
| 5,585,089 A | 12/1996 | Queen et al. |
| 5,625,825 A | 4/1997 | Rostoker et al. |
| 5,688,781 A | 11/1997 | Siegall et al. |
| 5,807,819 A | 9/1998 | Cheng et al. |
| 5,919,813 A | 7/1999 | De Juan, Jr. et al. |
| 5,980,929 A | 11/1999 | De Juan, Jr. |
| 5,994,128 A | 11/1999 | Fallaux et al. |
| 6,033,908 A | 3/2000 | Bout et al. |
| 6,075,181 A | 6/2000 | Kucherlapati et al. |
| 6,114,598 A | 9/2000 | Kucherlapati et al. |
| 6,133,426 A | 10/2000 | Gonzalez et al. |
| 6,150,584 A | 11/2000 | Kucherlapati et al. |
| 6,162,963 A | 12/2000 | Kucherlapati et al. |
| 6,342,219 B1 | 1/2002 | Thorpe et al. |
| 6,407,213 B1 | 6/2002 | Carter et al. |
| 6,455,026 B1 | 9/2002 | Mueller et al. |
| 6,455,035 B1 | 9/2002 | Suri et al. |
| 6,589,758 B1 | 7/2003 | Zhu |
| 6,596,722 B2 | 7/2003 | Moltzen et al. |

(Continued)

FOREIGN PATENT DOCUMENTS

| CN | 101802002 A | 8/2010 |
| CN | 107602702 A | 1/2018 |

(Continued)

OTHER PUBLICATIONS

Schroeder et al. (J Allergy Clin Immunol 2010, 125:S41-S52).*
Lloyd et al. Protein Engineering, Design & Selection 2009, 22:159-168.*

(Continued)

*Primary Examiner* — Sharon X Wen
(74) *Attorney, Agent, or Firm* — Sterne, Kessler, Goldstein & Fox P.L.L.C.

(57) ABSTRACT

Antibodies and antigen binding fragments thereof that bind to human protein tyrosine phosphatase beta (HPTPβ), and uses thereof.

10 Claims, 12 Drawing Sheets

Specification includes a Sequence Listing.

(56) References Cited

U.S. PATENT DOCUMENTS

| | | |
|---|---|---|
| 7,052,695 B2 | 5/2006 | Kalish |
| 7,226,755 B1 | 6/2007 | Peters et al. |
| 7,309,483 B2 | 12/2007 | Wiegand et al. |
| 7,354,579 B2 | 4/2008 | Holash et al. |
| 7,374,758 B2 | 5/2008 | Papadopoulos et al. |
| 7,507,568 B2 | 3/2009 | Evdokimov et al. |
| 7,588,924 B2 | 9/2009 | Evdokimov et al. |
| 7,589,212 B2 | 9/2009 | Gray et al. |
| 7,622,593 B2 | 11/2009 | Gray et al. |
| 7,632,862 B2 | 12/2009 | Peters et al. |
| 7,740,846 B2 | 6/2010 | Gerber et al. |
| 7,758,859 B2 | 7/2010 | Fuh et al. |
| 7,769,575 B2 | 8/2010 | Evdokimov et al. |
| 7,795,444 B2 | 9/2010 | Gray et al. |
| 7,973,142 B2 | 7/2011 | Rotello et al. |
| 8,106,078 B2 | 1/2012 | Gray et al. |
| 8,188,125 B2 | 5/2012 | Gray et al. |
| 8,258,268 B2 | 9/2012 | Wu et al. |
| 8,258,311 B2 | 9/2012 | Gray et al. |
| 8,329,916 B2 | 12/2012 | Amarasinghe et al. |
| 8,338,615 B2 | 12/2012 | Gray et al. |
| 8,349,322 B2 | 1/2013 | Borras et al. |
| 8,524,234 B2 | 9/2013 | Rotello et al. |
| 8,524,235 B2 | 9/2013 | Rotello et al. |
| 8,569,348 B2 | 10/2013 | Shalwitz et al. |
| 8,846,685 B2 | 9/2014 | Gray et al. |
| 8,883,832 B2 | 11/2014 | Shalwitz et al. |
| 8,895,563 B2 | 11/2014 | Gray et al. |
| 8,901,076 B2 | 12/2014 | Binz et al. |
| 8,946,232 B2 | 2/2015 | Gray et al. |
| 8,968,766 B2 | 3/2015 | Hughes et al. |
| 8,999,325 B2 * | 4/2015 | Peters ..................... A61P 7/10 |
| | | 424/178.1 |
| 8,999,953 B2 | 4/2015 | Loftsson et al. |
| 9,096,555 B2 | 8/2015 | Shalwitz et al. |
| 9,126,958 B2 | 9/2015 | Gray et al. |
| 9,174,950 B2 | 11/2015 | Shalwitz et al. |
| 9,248,172 B2 | 2/2016 | Srivastava et al. |
| 9,284,285 B2 | 3/2016 | Gray et al. |
| 9,403,789 B2 | 8/2016 | Eissenstat et al. |
| 9,440,963 B2 | 9/2016 | Peters et al. |
| 9,458,211 B1 | 10/2016 | Bakker et al. |
| 9,539,245 B2 | 1/2017 | Peters |
| 9,700,542 B2 | 7/2017 | Breslin et al. |
| RE46,592 E | 10/2017 | Gray et al. |
| 9,795,594 B2 | 10/2017 | Gray et al. |
| 9,926,367 B2 | 3/2018 | Rotello et al. |
| 9,949,956 B2 | 4/2018 | Shalwitz et al. |
| 9,968,674 B2 | 5/2018 | Ioffe et al. |
| 10,035,850 B2 | 7/2018 | Gekkieva et al. |
| 10,150,811 B2 | 12/2018 | Peters et al. |
| 10,220,048 B2 | 3/2019 | Peters et al. |
| 10,253,094 B2 * | 4/2019 | Peters ..................... A61P 35/00 |
| 10,276,202 B1 | 4/2019 | Pierre-Oliver et al. |
| 10,329,357 B2 * | 6/2019 | Peters ..................... A61P 27/06 |
| 10,463,650 B2 | 11/2019 | Gray et al. |
| 10,464,992 B2 | 11/2019 | Furfine et al. |
| 10,597,452 B2 * | 3/2020 | Peters ................. C07K 16/2896 |
| 10,604,569 B2 * | 3/2020 | Peters ..................... C07K 16/22 |
| 10,646,542 B2 | 5/2020 | Binz et al. |
| 10,815,300 B2 | 10/2020 | Peters |
| 10,894,824 B2 | 1/2021 | Peters |
| 11,136,389 B2 * | 10/2021 | Peters ..................... C07K 16/28 |
| 11,136,986 B2 | 10/2021 | Peters et al. |
| 11,180,551 B2 * | 11/2021 | Peters ................. A61K 39/3955 |
| 2003/0040463 A1 | 2/2003 | Wiegand et al. |
| 2003/0055006 A1 | 3/2003 | Siemeister et al. |
| 2003/0158083 A1 | 8/2003 | Peters |
| 2003/0215899 A1 | 11/2003 | Meng et al. |
| 2004/0077065 A1 | 4/2004 | Evdokimov et al. |
| 2004/0167183 A1 | 8/2004 | Klopfenstein et al. |
| 2004/0204863 A1 | 10/2004 | Kim et al. |
| 2004/0254197 A1 | 12/2004 | Tasaka et al. |
| 2005/0004056 A1 | 1/2005 | Meise et al. |
| 2005/0059639 A1 | 3/2005 | Wei |
| 2005/0158320 A1 | 7/2005 | Nichols et al. |
| 2005/0260132 A1 | 11/2005 | Chin et al. |
| 2006/0014204 A1 | 1/2006 | Gale et al. |
| 2007/0059762 A1 | 3/2007 | Araki et al. |
| 2007/0134234 A1 | 6/2007 | Smith et al. |
| 2007/0154482 A1 | 7/2007 | Sukhatme et al. |
| 2007/0299116 A1 | 12/2007 | Gray et al. |
| 2008/0004267 A1 | 1/2008 | Gray et al. |
| 2008/0076764 A1 | 3/2008 | Peters et al. |
| 2008/0108631 A1 | 5/2008 | Gray et al. |
| 2008/0268051 A1 | 10/2008 | Hughes et al. |
| 2009/0022715 A1 | 1/2009 | Rotello et al. |
| 2009/0227639 A1 | 9/2009 | Gray et al. |
| 2009/0246206 A1 | 10/2009 | Nielsen et al. |
| 2010/0016336 A1 | 1/2010 | Gray et al. |
| 2010/0030487 A1 | 2/2010 | Evdokimov et al. |
| 2010/0056610 A1 | 3/2010 | Peters et al. |
| 2010/0069448 A1 | 3/2010 | Gray et al. |
| 2010/0111894 A1 | 5/2010 | Benny-Ratsaby et al. |
| 2010/0226992 A1 | 9/2010 | Kabra |
| 2010/0256147 A1 | 10/2010 | Hangauer |
| 2011/0212951 A1 | 9/2011 | Gray et al. |
| 2011/0268656 A1 | 11/2011 | Ho et al. |
| 2011/0268694 A1 | 11/2011 | Shalwitz et al. |
| 2011/0274699 A1 | 11/2011 | Rotello et al. |
| 2012/0077853 A1 | 3/2012 | Gray et al. |
| 2012/0077975 A1 | 3/2012 | Gray et al. |
| 2012/0128625 A1 | 5/2012 | Shalwitz et al. |
| 2012/0129847 A1 | 5/2012 | Peters et al. |
| 2012/0237442 A1 | 9/2012 | Rossi et al. |
| 2013/0023542 A1 | 1/2013 | Gray et al. |
| 2013/0023543 A1 | 1/2013 | Gray et al. |
| 2013/0095065 A1 | 4/2013 | Peters et al. |
| 2013/0095105 A1 | 4/2013 | Peters et al. |
| 2013/0096140 A1 | 4/2013 | Gray et al. |
| 2013/0137741 A1 | 5/2013 | Kabra et al. |
| 2013/0190324 A1 | 7/2013 | Kompella et al. |
| 2013/0324558 A1 | 12/2013 | Gray et al. |
| 2013/0331386 A1 | 12/2013 | Shalwitz et al. |
| 2014/0010805 A1 | 1/2014 | Hart et al. |
| 2014/0044707 A1 | 2/2014 | Rotello et al. |
| 2014/0066458 A1 | 3/2014 | Shalwitz et al. |
| 2014/0073566 A1 | 3/2014 | Koh et al. |
| 2014/0179693 A1 | 6/2014 | Shalwitz et al. |
| 2014/0221666 A1 | 8/2014 | Gray et al. |
| 2014/0242026 A1 | 8/2014 | Shalwitz et al. |
| 2014/0249100 A1 | 9/2014 | Shalwitz et al. |
| 2014/0275103 A1 | 9/2014 | Peters et al. |
| 2014/0288134 A1 | 9/2014 | Peters et al. |
| 2015/0030603 A1 | 1/2015 | Kim et al. |
| 2015/0050277 A1 | 2/2015 | Peters et al. |
| 2015/0065781 A1 | 3/2015 | Bais et al. |
| 2015/0071941 A1 | 3/2015 | Sodhi et al. |
| 2015/0125455 A1 | 5/2015 | Green et al. |
| 2015/0125542 A1 | 5/2015 | Ohto et al. |
| 2015/0175676 A1 | 6/2015 | Fandl et al. |
| 2015/0190432 A1 | 7/2015 | Doiron et al. |
| 2015/0210656 A1 | 7/2015 | Gray et al. |
| 2015/0232575 A1 | 8/2015 | Peters et al. |
| 2015/0258120 A1 | 9/2015 | Zarnitsyn et al. |
| 2015/0259335 A1 | 9/2015 | Janusz et al. |
| 2015/0290235 A1 | 10/2015 | Gros et al. |
| 2015/0297675 A1 | 10/2015 | Osborne |
| 2015/0297740 A1 | 10/2015 | Rau et al. |
| 2016/0000871 A1 | 1/2016 | Quaggin |
| 2016/0008327 A1 | 1/2016 | Shalwitz et al. |
| 2016/0015810 A1 | 1/2016 | Deschatelets et al. |
| 2016/0030393 A1 | 2/2016 | Breslin et al. |
| 2016/0038467 A1 | 2/2016 | Peters |
| 2016/0045566 A1 | 2/2016 | Purcell et al. |
| 2016/0058828 A1 | 3/2016 | Dumont et al. |
| 2016/0082129 A1 | 3/2016 | Peters |
| 2016/0130321 A1 | 5/2016 | Burian |
| 2016/0130337 A1 | 5/2016 | Gekkieva et al. |
| 2016/0137717 A1 | 5/2016 | Burian |
| 2016/0144025 A1 | 5/2016 | Vitti et al. |
| 2016/0151410 A1 | 6/2016 | Ma et al. |
| 2016/0151448 A1 | 6/2016 | Van et al. |
| 2016/0159893 A1 | 6/2016 | Burian et al. |

(56) References Cited

U.S. PATENT DOCUMENTS

| | | |
|---|---|---|
| 2016/0168240 A1 | 6/2016 | Burian et al. |
| 2016/0075797 A1 | 8/2016 | Weaver et al. |
| 2016/0220540 A1 | 8/2016 | Peters et al. |
| 2016/0220541 A1 | 8/2016 | Peters et al. |
| 2016/0251421 A1 | 9/2016 | Brown et al. |
| 2016/0252526 A1 | 9/2016 | Bergmann et al. |
| 2016/0333090 A1 | 11/2016 | Horlick et al. |
| 2016/0374996 A1 | 12/2016 | Gray et al. |
| 2017/0079959 A1 | 3/2017 | Peters |
| 2017/0096479 A1 | 4/2017 | Koenig et al. |
| 2017/0145416 A1 | 5/2017 | Epstein et al. |
| 2017/0260265 A1 | 9/2017 | Duerr et al. |
| 2017/0275353 A1 | 9/2017 | Sheng et al. |
| 2017/0298019 A1 | 10/2017 | Gardner et al. |
| 2017/0319602 A1 | 11/2017 | Peters et al. |
| 2017/0349649 A1 | 12/2017 | Rotello et al. |
| 2018/0009890 A1 | 1/2018 | Peters et al. |
| 2018/0016245 A1 | 1/2018 | Shalwitz et al. |
| 2018/0022741 A1 | 1/2018 | Peters et al. |
| 2018/0022804 A1 | 1/2018 | Peters et al. |
| 2018/0037579 A1 | 2/2018 | Peters et al. |
| 2018/0044432 A1 | 2/2018 | Peters et al. |
| 2018/0092883 A1 | 4/2018 | Peters et al. |
| 2018/0207233 A1 | 7/2018 | Rudolf et al. |
| 2018/0221346 A1 | 8/2018 | Gray et al. |
| 2018/0237429 A1 | 8/2018 | Peters et al. |
| 2018/0237430 A1 | 8/2018 | Peters et al. |
| 2018/0251457 A1 | 9/2018 | Peters et al. |
| 2018/0353614 A1 | 12/2018 | Peters et al. |
| 2019/0023773 A1 | 1/2019 | Rotello et al. |
| 2019/0046609 A1 | 2/2019 | Yancopoulos |
| 2019/0076405 A1 | 3/2019 | Shalwitz |
| 2019/0077862 A1 | 3/2019 | Peters et al. |
| 2019/0077863 A1 | 3/2019 | Peters et al. |
| 2019/0218282 A1 | 7/2019 | Dengl et al. |
| 2019/0256889 A1 | 8/2019 | Quaggin |
| 2019/0290725 A1 | 9/2019 | Vitti et al. |
| 2019/0343918 A1 | 11/2019 | Graham et al. |
| 2019/0381008 A1 | 12/2019 | Zeitz et al. |
| 2020/0087412 A1 | 3/2020 | Fang et al. |
| 2020/0115455 A1 | 4/2020 | Bedi et al. |
| 2020/0140547 A1 | 5/2020 | Bedi et al. |
| 2021/0095017 A1 | 4/2021 | Peters et al. |
| 2021/0171618 A1 | 6/2021 | Peters |

FOREIGN PATENT DOCUMENTS

| | | |
|---|---|---|
| EP | 1165115 B1 | 5/2003 |
| EP | 1292335 B1 | 5/2007 |
| EP | 2004697 A2 | 12/2008 |
| EP | 2385763 A1 | 11/2011 |
| EP | 2451279 A1 | 5/2012 |
| EP | 2142189 B1 | 2/2013 |
| EP | 2592072 A2 | 5/2013 |
| EP | 2592073 A2 | 5/2013 |
| EP | 2624916 A2 | 8/2013 |
| EP | 2766043 A1 | 8/2014 |
| EP | 2766044 A1 | 8/2014 |
| EP | 2041129 B1 | 9/2014 |
| EP | 2041102 B1 | 11/2014 |
| EP | 2803663 A1 | 11/2014 |
| EP | 2038265 B1 | 3/2015 |
| EP | 2967066 A1 | 1/2016 |
| EP | 3168234 A1 | 5/2017 |
| EP | 2371865 B1 | 7/2017 |
| EP | 2592073 B1 | 8/2017 |
| EP | 2846836 B1 | 8/2019 |
| EP | 3628324 A1 | 4/2022 |
| WO | WO 9312227 A1 | 6/1993 |
| WO | WO-9312227 A1 | 6/1993 |
| WO | WO 9631598 A1 | 10/1996 |
| WO | WO-9818914 A1 | 5/1998 |
| WO | WO 9845331 A2 | 10/1998 |
| WO | WO 9845331 A3 | 12/1998 |
| WO | WO-0057901 A1 | 10/2000 |
| WO | WO-0065085 A1 | 11/2000 |
| WO | WO-0065088 A2 | 11/2000 |
| WO | WO 0224782 A1 | 3/2002 |
| WO | WO-0226774 A2 | 4/2002 |
| WO | WO-03084565 A2 | 10/2003 |
| WO | WO-2006068953 A2 | 6/2006 |
| WO | WO-2006116713 A1 | 11/2006 |
| WO | WO 2007033216 A2 | 3/2007 |
| WO | WO 2007087457 A2 | 8/2007 |
| WO | WO-2007113648 A2 | 10/2007 |
| WO | WO-2007116360 A2 | 10/2007 |
| WO | WO-2008002569 A2 | 1/2008 |
| WO | WO-2008002570 B1 | 4/2008 |
| WO | WO-2008002571 B1 | 4/2008 |
| WO | WO 2009006112 A1 | 1/2009 |
| WO | WO 2009055343 A2 | 4/2009 |
| WO | WO 2009136352 A1 | 11/2009 |
| WO | WO 2010060748 A1 | 6/2010 |
| WO | WO-2010081172 A1 | 7/2010 |
| WO | WO-2011005330 A1 | 1/2011 |
| WO | WO 2011135067 A1 | 11/2011 |
| WO | WO-2012047966 A2 | 4/2012 |
| WO | WO-2013056233 A1 | 4/2013 |
| WO | WO-2013056240 A1 | 4/2013 |
| WO | WO 2011087066 A1 | 5/2013 |
| WO | WO-2014145068 A1 | 9/2014 |
| WO | WO-2015138882 A1 | 9/2015 |
| WO | WO-2015152416 A1 | 10/2015 |
| WO | WO-2016022813 A1 | 2/2016 |
| WO | WO-2016049183 A1 | 3/2016 |
| WO | WO 2016115092 A1 | 7/2016 |
| WO | WO 2017035430 A2 | 3/2017 |
| WO | WO-2017053566 A1 | 3/2017 |
| WO | WO 2018017714 A1 | 1/2018 |
| WO | WO 2018067646 A1 | 4/2018 |
| WO | WO 2018229034 A1 | 12/2018 |
| WO | WO 2019168947 A1 | 9/2019 |
| WO | WO 2019175727 A1 | 9/2019 |
| WO | WO 2019222547 A1 | 11/2019 |
| WO | WO 2020068653 A1 | 2/2020 |

OTHER PUBLICATIONS

Rudikoff et al. (Proc Natl Acad Sci USA 1982 vol. 79 p. 1979).*
MacCallum et al. (J. Mol. Biol. 1996 262, 732-745).*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*
Lamminmaki et al. (JBC 2001,276:36687-36694).*
Piche-Nicholas et al. MABS 2018, 10:81-94.*
Amarasinghe.K.K.D., et al., Design and synthesis of potent, non-peptidic inhibitors of HPTPß, Bioorganic & Medicinal Chemistry Letters, 16:4252-4256, Elsevier, Netherlands (2006).
Baumer, S., et al., "Vascular endothelial cell-specific phosphotyrosine phosphatase (VEPTP) activity is required for blood vessel development," Blood 107(12):4754-4762, The American Society of Hematology, United States (Jun. 2006).
Bosse, R. and Vestweber D., "Only simultaneous blocking of the L- and P-selectin completely inhibits neutrophil C migration into mouse peritoneum", Eur. J. Immunol. 24:3019-3024, VCH Verlagsgesellschaft mbH, Germany (1994).
Broermann, A., et al., "Dissociation of VE-PTP from VE-cadherin is required for leukocyte extravasation and for VEGF-induced vascular permeability in vivo," J Exp Med. 208(12):2393-401, The Rockefeller University Press, United States (Nov. 2011).
Campochiaro, P.A., et al., "Enhanced Benefit in Diabetic Macular Edema from AKB-9778 Tie2 Activation Combined with Vascular Endothelial Growth Factor Suppression. Ophthalmology," 123(8):1-9, Elsevier, Inc., Netherlands (Aug. 2016).
Clackson, T., et al., "Making antibody fragments using phage display libraries," Nature. 352(6336):624-628, Nature Research, United Kingdom (Aug. 1991).

(56) References Cited

OTHER PUBLICATIONS

Clarke, JM et al., "Targeted inhibition of VEGF Receptor-2: An update on Ramucirumab," Expert Opin Biol Ther. 13(8): 1187-1196, Author Manuscript, Taylor & Francis, United Kingdom (Aug. 2013).
Colman, P.M., et al., "Effects of amino acid sequence changes on antibody-antigen interactions," Research in Immunology 145(1):33-36, Elsevier, Netherlands (Jan. 1994).
Co-Pending U.S. Appl. No. 17/804,396, inventors Peters, K., et al., filed May 27, 2022 (Not Published).
Crescioli, S., et al., "IgG4 Characteristics and Functions in Cancer Immunity," Curr Allergy Asthma Rep 16:7, Springer, Germany (2016).
Doukas, J., et al., "Topical administration of a multi-targeted kinase inhibitor suppresses choroidal neovascularization and retinal edema," J Cell Physiol. 216(1):29-37, Author Manuscript, John Wiley & Sons, Inc., United States (Jul. 2008).
Elias, L. and Hunt, W.C., "A literature analysis of prognostic factors for response and quality of response of patients with renal cell carcinoma to interleukin-2-based therapy," Oncology 61(2):91-101, S. Karger AG, Basel (2001).
E Silva, R.L., et al., Tyrosine kinase blocking collagen IV-derived peptide suppresses ocular neovascularization and vascular leakage, Sci Transl Med. 9(373), Author Manuscript, American Association for the Advancement of Science, United States (Jan. 2017).
Supplementary European Search Report and Search Opinion for EP Application No. EP 12840220.3, Munich, Germany, dated May 11, 2015, 7 pages.
Supplementary European Search Report and Search Opinion for EP Application No. EP 12840725.1, Munich, Germany, dated May 12, 2015.
Frye, M., et al., "Interfering with VE-PTP stabilizes endothelial junctions in vivo via Tie-2 in the absence of VE-cadherin," JEM 212(13):2267-2287, The Rockefeller University Press, United States (Dec. 2015).
Fukuhara, S., et al., "Differential function of Tie2 at cell-cell contacts and cell-substratum contacts regulated by angiopoietin-1," Nat Cell Biol. 10(5):513-526, Nature Publishing Group, Germany (May 2008).
Fukuhara, S. and Mochizuki, N., "Vascular endothelial cells and adjoining cells for their mutual adhesion/interaction for stabilization and angiogenesis," Seikagaku. The Journal of Japanese Biochemical Society 82(4):290-301, Japanese Biochemical Society, Japan (Apr. 2010).
Gallagher, D.C., et al., "Angiopoietin 2 is a Potential Mediator of High-Dose Interleutkin 2-Induced Vascular Leak," Clin Cancer Res 13(7):2115-2120, American Association for Cancer Research, United States (Apr. 2007).
Goel, S., et al., Effects of vascular-endothelial protein tyrosine phosphatase inhibition on breast cancer vasculature and metastatic progression. J Natl Cancer Inst. 21;105(16):1188-1201, Oxford University Press, United Kingdom (Aug. 2013).
Golay, J. and Introna, M., Mechanism of action of therapeutic monoclonal antibodies: promises and pitfalls of in vitro and in vivo assays. Arch Biochem Biophys. 526(2):146-153, Elsevier, Netherlands (Oct. 2012).
Gotsch, U., et al., "VE-cadherin antibody accelerates neutrophil recruitment in vivo," J Cell Sci. 110:583-588, The Company of Biologists Limited, Great Britain (Mar. 1997).
Gozes, Y., et al., "Anthrax Lethal Toxin Induces Ketotifen-Sensitive Intradermal Vascular Leakage in Certain Inbred Mice," Infect Immun. 74(2):1266-1272, The American Society for Microbiology, United States (Feb. 2006).
Gurnik, S., et al., "Angiopoietin-2-induced blood-brain barrier compromise and increased stroke size are rescued by VE-PTP-dependent restoration of Tie2 signaling," Acta Neuropathol 131(5):753-773, Springer, Germany (May 2016).
Hayashi, M., et al., VE-PTP regulates VEGFR2 activity in stalk cells to establish endothelial cell polarity and lumen formation. Nat Commun. 4:1672, Macmillan Publishing Limited, United Kingdom (2013).
Hudson, P.J. and Souriau, C., "Engineered antibodies," Nat Med. 9(1):129-34, Nature Publishing Group, Germany (Jan. 2003).
Imamura, T., et al., "Induction of vascular leakage through release of bradykinin and a novel kin in by cysteine proteinases from *Staphylococcus aureus*," J Exp Med. 201(10):1669-1676, The Rockefeller University Press, United States (May 2005).
International Search Report and Written Opinion for International Application No. PCT/US2012/060263, U.S. Patent and Trademark Office, Alexandria, VA, dated Dec. 6, 2012, 7 pages.
International Search Report and Written Opinion for International Application No. PCT/US2012/060273, U.S. Patent and Trademark Office, Alexandria, VA, dated Dec. 24, 2012, 9 pages.
International Search Report and Written Opinion for International Application No. PCT/US2019/052405, U.S. Patent and Trademark Office, Alexandria, VA, dated Feb. 5, 2020, 26 pages.
International Search Report and Written Opinion for International Application No. PCT/US2017/042855, U.S. Patent and Trademark Office, Alexandria, VA, dated Dec. 26, 2017, 21 pages.
International Union of Basic and Clinical Pharmacology/British Pharmacological Society (IUPHAR/BPS) Guide to Pharmacology Database: Ligand ID: 8371, International Nonproprietary Name: abicipar pegol; Link: https://www.guidetopharmacology.org/GRAC/LigandDisplayForward?tab=summary&ligandId=8371, printed Jun. 15, 2020.
International Union of Basic and Clinical Pharmacology/British Pharmacological Society (IUPHAR/BPS) Guide to Pharmacology Database: Ligand ID: 8371, International Nonproprietary Name: abicipar pegol, Peptide Sequence; Link: https://www.guidetopharmacology.org/GRAC/LigandDisplayForward?tab=structure&ligandId=8371, printed Jun. 15, 2020.
International Union of Basic and Clinical Pharmacology/British Pharmacological Society (IUPHAR/BPS) Guide to Pharmacology Database: Ligand ID: 8371, International Nonproprietary Name: abicipar pegol, Target: VEGFA, Link: https://www.guidetopharmacology.org/GRAC/LigandDisplayForward?tab=biology&ligandId=8371, printed Jun. 15, 2020.
International Union of Basic and Clinical Pharmacology/British Pharmacological Society (IUPHAR/BPS) Guide to Pharmacology Database: Ligand ID: 8371, International Nonproprietary Name: abicipar pegol, Clinical Data; Summary of Clinical Use, and Mechanism of Action and Pharmacodynamic Effects; Link: https://www.guidetopharmacology.org/GRAC/LigandDisplayForward?tab=biology&ligandId=8371, printed Jun. 15, 2020.
IUPHAR/BPS Guide to Pharmacology database for Ligand ID: 8371, Name: abicipar pegol, available at https://www.guidetopharmacology.org/GRAC/LigandDisplayForward?tab=summary&ligandId=8371, 5 pages, Accessed Nov. 21, 2019.
Jubala, C.M., et al., "CD20 expression in normal canine B cells and in canine non-Hodgkin Lymphoma," Vet Pathol. 42(4):468-476, SAGE Publications, New York (Jul. 2005).
Kienast, Y., et al., "Ang-2-VEGF-A CrossMab, a Novel Bispecific Human IgG1 Antibody Blocking VEGF-A and Ang-2 Functions Simultaneously, Mediates Potent antitumor, Antiangiogenic, and Antimetastic Efficacy," Clinical Cancer Research 19(24):6730-6740, American Association for Cancer Research, United States (Oct. 2013).
Kipriyanov, S.M. and Le Gall, F., "Generation and production of engineered antibodies," Mol Biotechnol. 26(1):39-60, Humana Press, Inc., Springer Science+Business Media, Germany (Jan. 2004).
Lo, B.K.C., "Antibody humanization by CDR grafting," Ch.7 in Methods in Mol Biol., Antibody Engineering: Methods and Protocols 248:135-59, Totowa, New Jersey (2004).
Luo, G., et al., "Molecular mechanism underlying the action of a novel fusion inhibitor of influenza A virus," J Virol. 71(5):4062-4070, American Society for Microbiology, United States (May 1997).

(56) References Cited

OTHER PUBLICATIONS

Marneros, A., et al., "Endogenous endostatin inhibits choroidal neovascularization," FASEB J. 21(14):3809-3818, Federation of American Societies for Experimental Biology, United States (Dec. 2007).

Mellberg, S., et al., "Transcriptional profiling reveals a critical role for tyrosine phosphatase VEPTP in regulation of VEGFR2 activity and endothelial cell morphogenesis," FASEB J. 23(5):1490-1502, Federation of American Societies for Experimental Biology, United States (May 2009).

Miles, A.A. and Miles, E.M., "Vascular reactions to histamine, histamine-liberator and leukotaxine in the skin of guinea-pigs," J Physiol. 118(2):228-257, Wiley-Blackwell on behalf of The Physiological Society, United States (Oct. 1952).

Morrissey, C., et al., "Differential expression of angiogenesis associated genes in prostate cancer bone, liver and lymph node metastases," Clin Exp Metastasis. 25(4):377-388, Springer Science+Business Media B.V., Germany (2008).

Muyldermans, S., "Single domain camel antibodies: current status," Reviews in Molecular Biotechnology 74(4):277-302, Elsevier, Netherlands (Jun. 2001).

Nguyen, Q.D., et al., "Vascular endothelial growth factor is a critical stimulus for diabetic macular edema," Am J Ophthalmol. 142(6):961-969, Elsevier, Inc., Netherlands (Dec. 2006).

Nishimura, E., "Current status and feature of diabetic retinopathy drug therapy," Journal of the Showa Medical Association 70(1):45-51, Showa Medical Association, Japan (Feb. 2010).

Notice of Allowance dated Jan. 15, 2020, in U.S. Appl. No. 16/180,850, Peters, K., filed Nov. 5, 2018, 9 pages.

Notice of Allowance dated Jan. 30, 2015, in U.S. Appl. No. 13/652,154, Peters, K., filed Oct. 15, 2012, 8 pages.

Notice of Allowance dated Nov. 30, 2018, in U.S. Appl. No. 15/654,289, Peters, K., filed Jul. 19, 2017, 7 pages.

Notice of Allowance dated Sep. 26, 2018, in U.S. Appl. No. 15/438,218, Peters, K., filed Feb. 21, 2017, 8 pages.

Nottebaum, A.F., et al. VE-PTP maintains the endothelial barrier via plakoglobin and becomes dissociated from VE-cadherin by leukocytes and by VEGF, J Exp Med. 205(12):2929-2945, The Rockefeller University Press, United States (Nov. 2008).

Office Action dated Sep. 5, 2013, in U.S. Appl. No. 13/652,154, Peters, K., et al., filed Oct. 15, 2012, 23 pages.

Office Action dated Apr. 7, 2014, in U.S. Appl. No. 13/652,154, Peters, K., et al., filed Oct. 15, 2012, 25 pages.

Office Action dated Sep. 11, 2013, in U.S. Appl. No. 13/652,203, Peters, K., et al., filed Oct. 15, 2012, 10 pages.

Office Action dated May 15, 2014, in U.S. Appl. No. 13/652,203, Peters, K., et al., filed Oct. 15, 2012, 12 pages.

Office Action dated Apr. 17, 2015, in U.S. Appl. No. 13/652,203, Peters, K., et al., filed Oct. 15, 2012, 12 pages.

Office Action dated Aug. 22, 2016 in U.S. Appl. No. 13/652,203, Peters, K., et al., filed Oct. 15, 2012, 15 pages.

Office Action dated Jan. 4, 2016, in U.S. Appl. No. 13/652,203, Peters, K., et al., filed Oct. 15, 2012, 17 pages.

Office Action dated Mar. 1, 2018, in U.S. Appl. No. 15/438,218, Peters, K., et al., filed Feb. 21, 2017, 10 pages.

Office Action dated Aug. 3, 2018, in U.S. Appl. No. 15/438,218, Peters, K., et al., filed Feb. 21, 2017, 8 pages.

Office Action dated Jul. 6, 2018, in U.S. Appl. No. 15/654,289, Peters, K., et al., filed Jul. 19, 2017, 8 pages.

Office Action dated Jul. 9, 2018, in U.S. Appl. No. 15/463,340, Peters, K., et al., filed Mar. 20, 2017, 14 pages.

Office Action dated Sep. 22, 2016, in U.S. Appl. No. 14/627,463, Peters, K., et al., filed Feb. 20, 2015, 24 pages.

Office Action dated Aug. 30, 2019, in U.S. Appl. No. 16/180,850, Peters, K., et al., filed Nov. 5, 2018, 11 pages.

Office Action dated Aug. 30, 2019, in U.S. Appl. No. 16/180,854, Peters, K., et al., filed Nov. 5, 2018, 11 pages.

Oliner, J., et al., "Suppression of angiogenesis and tumor growth by selective inhibition of angiopoietin-2," Cancer Cell. 6(5):507-516, Cell Press, United States (Nov. 2004).

Park, Y-H., et al., "Effect of sorafenib on experimental choroidal neovascularization in the rat," Clin Experiment Ophthalmol. 38(7):718-726, Royal Australian and New Zealand College of Ophthalmologists, Australia (Oct. 2010).

Paul, W.E., (ed.) Fundamental Immunology, 3rd Edition, Chapter 9, pp. 292-295, Raven Press, New York (1993).

Praidou, A., et al., "Angiogenic growth factors and their inhibitors in diabetic retinopathy," Curr Diabetes Rev. 6(5):304-312, Bentham Science Publishers Ltd., United Arab Emirates (Sep. 2010).

Riemer, A.B., et al., "Matching of trastuzumab (Herceptin) epitope mimics onto the surface of Her-2/neu—a new method of epitope definition. Mol Immunol. 42(9):1121-1124, Elsevier, Netherlands (May 2005).

Rudikoff, et al. Single amino acid substitution altering antigen-binding specificity. Proc Natl Acad Sci USA 79(6):1979-1983, United States National Academy of Sciences, United States (Mar. 1982).

Saharinen, P., et al., "Angiopoietins assemble distinct Tie2 signalling complexes in endothelial cell-cell and cell-matrix contacts," Nat Cell Biol. 10(5):527-537, Supplementary Information, Nature Publishing Group, Germany (May 2008).

Shen J, et al., "In Vivo Immunostaining Demonstrates Macrophages Associate with Growing and Regressing Vessels," Invest. Ophthalmol. Vis. Sci., 48(9):4335-4341, Association for Research in Vision and Ophthalmology, United States (2007).

Shen, J., et al., "Targeting VE-PTP activates TIE2 and stabilizes the ocular vasculature," J Clin Invest. 124(10):4564-4576, American Society for Clinical Investigation, United States (Oct. 2014).

Sidwell, R.W., et al. "Utilization of pulse oximetry for the study of the inhibitory effects of antiviral agents on influenza virus in mice," Antimicrob Agents Chemother. 36(2):473-476, American Society for Microbiology, United States (Feb. 1992).

Simeon, R. and Chen, Z., "In vitro-engineered non-antibody protein therapeutics," Protein Cell 9(1):3-14 Springer Nature Switzerland AG, Germany (2018).

Skolnick, J. and Fetrow, J.S., "From genes to protein structure and function: novel applications of computational approaches in the genomic era," Trends Biotechnol. 18(1):34-39, Elsevier Science Ltd., Netherlands (Jan. 2000).

Smith, L. E. H., et al., "Oxygen-induced retinopathy in the mouse," Invest Ophthalmol Vis Sci. 35(1):101-111, Association for Research in Vision and Ophthalmology (Jan. 1994).

Sone, H., et al., "Effects of intraocular or systemic administration of neutralizing antibody against vascular endothelial growth factor on the murine experimental model of retinopathy," Life Sci. 65(24):2573-2580, Elsevier, Netherlands (1999).

Stancovski, I., et al., "Mechanistic aspects of the opposing effects of monoclonal antibodies to the ERBB2 receptor on tumor growth," Proc Natl Acad Sci U SA. 88(19):8691-8695, United States National Academy of Sciences, United States (Oct. 1991).

Tam, S.H., et al., "Functional Biophysical, and Structural Characterization of Human IgG1 and Ig4 Fc Variants with Ablated Immune Functionality," Antibodies 6, 12, MDPI, Basel, Switzerland (2017).

Tobe, T., et al., "Targeted Disruption of the FGF2 Gene Does Not Prevent Choroidal Neovascularization in a Murine Model," Am. J. Pathol., 153(5):1641-1646, American Society to Investigative Pathology (1998).

Trieu, M., et al., "Vasculotide, an Angiopoietin-1 Mimetic, Restores Microcirculatory Perfusion and Microvascular Leakage and Decreases Fluid Resuscitation Requirements in Hemorrhagic Shock," Anesthesiology 128(2):361-74, Lippincot Williams & Wilkins, United States (Feb. 2018).

Van Der Flier, F.E., et al., "Antibody neutralization of vascular endothelial growth factor (VEGF) fails to attenuate vascular permeability and brain edema in experimental pneumococcal meningitis," J Neuroimmunol. 160(1-2):170-177, Elsevier, Netherlands (Mar. 2005).

Varughese, M., et al., "Internalization of a Bacillus anthracis protective antigen-c-Myc fusion protein mediated by cell surface anti-c-Myc antibodies," Mol Med. 4(2):87-95, Springer Nature, Germany (Feb. 1998).
Wang, Q., et al., "Novel VEGF Decoy Receptor Fusion Protein Conbercept Targeting Multiple VEGF Isoforms Provide Remark-

(56) References Cited

OTHER PUBLICATIONS able Anti-Angiogenesis Effect In Vivo," PLOS ONE, 8(8):e70544, PLOS, United States (Aug. 2013).
Wang, X., et al., "IgG Fc engineering to modulate antibody effector functions," Protein Cell 9(1):63-73, Springer Nature, Germany (2018).
Witte, L., et al., "Monoclonal antibodies targeting the VEGF receptor-2 (Flk1/KDR) as an antiangiogenic therapeutic strategy," Cancer Metastasis Rev. 17(2):155-161, Kluwer Academic Publishers, Netherlands (Jun. 1998).
Wu, H., et al., "Humanization of a murine monoclonal antibody by simultaneous optimization of framework and CDR residues," J Mol Biol. 294(1):151-162, Academic Press, United States (Nov. 1999).
Yacyshyn, O.K., et al., "Tyrosine phosphatase beta regulates angiopoietin-Tie2 signaling in human endothelial cells," Angiogenesis 12(1):25-33 Springer Science+Business Media B.V., Germany (2009).
Yang, J., et al., "Comparison of Binding Characteristics and In Vitro Activities of Three Inhibitors of Vascular Endothelial Growth Factor A," Molecular Pharmaceutics 11 (10):3421-3430, American Chemical Society (2014).
Yu, L., et al., "Interaction between bevacizumab and murine VEGF-A: A reassessment," Invest Ophthalmol Vis Sci. 49(2):522-527, Association for Research in Vision and Ophthalmology, United States (Feb. 2008).
Adamsky, et al. Glial tumor cell adhesion is mediated by binding of the FNIII domain of receptor protein tyrosine phosphatase beta (RPTPbeta) to tenascin C. Oncogene. Feb. 1, 2001;20(5):609-18.
Altschul, et al. Gapped BLAST and PSI-BLAST: a new generation of protein database search programs. Nucleic Acids Res. Sep. 1, 1997;25(17):3389-402.
Annex, et al. Growth factor-induced therapeutic angiogenesis in the heart: protein therapy. Cardiovasc Res. Feb. 15, 2005;65(3):649-55.
Ardelt, et al. Estradiol regulates angiopoietin-1 mRNA expression through estrogen receptor-alpha in a rodent experimental stroke model. Stroke. Feb. 2005;36(2):337-41. Epub Jan. 6, 2005.
Attwood. Genomics. The Babel of bioinformatics. Science. Oct. 20, 2000;290(5491):471-3.
Auerbach, et al. Angiogenesis assays: a critical overview. Clin Chem. Jan. 2003;49(1):32-40.
Barany, et al. Solid-phase peptide synthesis: a silver anniversary report. Int J Pept Protein Res. Dec. 1987;30(6):705-39.
Bartlett, et al. Molecular Recognition in Chemical and Biological Problems; Cavet: A Program to Facilitate the Structure-Derived Design of Biologically Active Molecules. Special Pub., Royal Chem. Soc. 1989; 78:182-196.
Bohm. The computer program LUDI: a new method for the de novo design of enzyme inhibitors. J Comput Aided Mol Des. Feb. 1992;6(1):61-78.
Bussolino, et al. Molecular mechanisms of blood vessel formation. Trends Biochem Sci. Jul. 1997;22(7):251-6.
Campbell Monoclonal Antibody Technology, 1984, Chapter 1, pp. 1-32.
Carano, et al. Angiogenesis and bone repair. Drug Discov Today. Nov. 1, 2003;8(21):980-9.
Carvalho, et al. The role of angiogenesis in a murine tibial model of distraction osteogenesis. Bone. May 2004;34(5):849-61.
Chanteau, et al. Synthesis of anthropomorphic molecules: the NanoPutians. J Org Chem. Nov. 14, 2003;68(23):8750-66.
Clackson, et al., Making Antibody Fragments Using Phage Display Libraries, Nature, 1991, 352:624-8.
Cohen, et al. Molecular modeling software and methods for medicinal chemistry. J Med Chem. Mar. 1990;33(3):883-94.
Collaborative Computational Project, No. 4. The CCP4 suite: programs for protein crystallography. Acta Crystallogr D Biol Crystallogr. Sep. 1, 1994;50(Pt 5):760-3.
Daar. Emerging resistance profiles of newly approved antiretroviral drugs. Top HIV Med. Oct.-Nov. 2008;16(4):110-6.
Dean. Recent advances in drug design methods: where will they lead? Bioessays. Sep. 1994;16(9):683-7.

European search report and opinion dated Apr. 5, 2012 for EP Application No. 11155518.1.
Fachinger, et al. Functional interaction of vascular endothelial-protein-tyrosine phosphatase with the angiopoietin receptor Tie-2. Oncogene. Oct. 21, 1999;18(43):5948-53.
Feng, et al. Lung cancer cell migration is regulated via repressing growth factor PTN/RPTP [beta]/[zeta] signaling by menin. Oncogene. Sep. 30, 2010;29(39):5416-26. doi: 10.1038/onc.2010.282. Epub Jul. 19, 2010.
Flower. Modelling G-protein-coupled receptors for drug design. Biochim Biophys Acta. Nov. 16, 1999;1422(3):207-34.
Foehr, et al. Targeting of the receptor protein tyrosine phosphatase beta with a monoclonal antibody delays tumor growth in a glioblastoma model. Cancer Res. Feb. 15, 2006;66(4):2271-8.
Folkman. Tumor angiogenesis. The Molecular Basis of Cancer (eds. Mendelsohn, J., Howley, P. M., Israel, M. A. & Liotta, L. A.) Ch. 10. 206-232 (1995).
Gaits, et al. Increase in receptor-like protein tyrosine phosphatase activity and expression level on density-dependent growth arrest of endothelial cells. Biochem J. Oct. 1, 1995;311 ( Pt 1):97-103.
Goodford. A computational procedure for determining energetically favorable binding sites on biologically important macromolecules. J Med Chem 28(7):849-857 (1985).
Goodsell, et al. Automated docking of substrates to proteins by simulated annealing. Proteins. 1990;8(3):195-202.
Hagerstrand, et al. Gene expression analyses of grade II gliomas and identification of rPTP/ as a candidate oligodendroglioma marker. Neuro Oncol. Feb. 2008;10(1):2-9. Epub Nov. 14, 2007.
Harder, et al. Characterization and kinetic analysis of the intracellular domain of human protein tyrosine phosphatase 13 (HPTP(3) using synthetic phosphopeptides. Biochem J. 1994; 296:395-401.
Henikoff, et al. Amino acid substitution matrices from protein blocks. Proc Natl Acad Sci U S A. Nov. 15, 1992;89(22):10915-9.
Hopkins, et al. Inhibitors of kinesin activity from structure-based computer screening. Biochemistry. Mar. 14, 2000;39(10):2805-14.
Houghten, et al. New Approaches to Immunization, Vaccines 86, Cold Spring Harbor Laboratory, p. 21-25, 1986.
Huang, et al. HCPTPA, a Protein Tyrosine Phosphatase that Regulates Vascular Endothelial Growth Factor Receptor-Mediated Signal Transduction and Biological Activity. J Biol. Chem. 1999; 53:38183-38188.
International search report and written opinion dated Jan. 17, 2008 for PCT/IB2007/051239.
Itoh, et al. Purification and characterization of the catalytic domains of the human receptor-linked protein tyrosine phosphatases HPTP beta, leukocyte common antigen (LCA), and leukocyte common antigen-related molecule (LAR). J Biol Chem. Jun. 15, 1992;267(17):12356-63.
Jeansson, et al., Angiopoietin-1 is essential in mouse vasculature during development and In response to injury, The Journal of Clinical Investigation, Jun. 2011, 121(6):2278-89.
Jones, et al. Development and validation of a genetic algorithm for flexible docking. J Mol Biol. Apr. 4, 1997;267(3):727-48.
Jones, et al. Molecular recognition of receptor sites using a genetic algorithm with a description of desolvation. J Mol Biol. Jan. 6, 1995;245(1):43-53.
Keen. Radioligand Binding Methods for Membrane Preparations and Intact cells, Methods in Molecular Biology, 83:Receptor Signal Transduction Protocols, edited Humana Press Inc., Totoway N.J. (1997).
Kohler, et al. Continuous cultures of fused cells secreting antibody of predefined specificity. 1975. Biotechnology. 1992;24:524-6.
Krueger, et al. Structural diversity and evolution of human receptor-like protein tyrosine phosphatases. EMBO J. Oct. 1990;9(10):3241-52.
Kugathasan, et al. Role of angiopoietin-1 in experimental and human pulmonary arterial hypertension. Chest. Dec. 2005;128(6 Suppl):633S-642S.
Kuntz, et al. A geometric approach to macromolecule-ligand interactions. J Mol Biol. Oct. 25, 1982;161(2):269-88.
Lederman et al. A single amino acid substitution in a common African allele of the CD4 molecule ablates binding of the monoclonal antibody, OKT4. Mol Immunol 28(11):1171-1181 (1991).

(56) References Cited

OTHER PUBLICATIONS

Li, et al. beta-Endorphin omission analogs: dissociation of immunoreactivity from other biological activities. Proc Natl Acad Sci U S A. Jun. 1980;77(6):3211-4.
Lin, et al. Inhibition of tumor angiogenesis using a soluble receptor establishes a role for Tie2 in pathologic vascular growth. J Clin Invest. Oct. 15, 1997;100(8):2072-8.
Lip, et al. Plasma vascular endothelial growth factor, angiopoietin-2, and soluble angiopoietin receptor tie-2 in diabetic retinopathy: effects of laser photocoagulation and angiotensin receptor blockade. Br J Ophthalmol. Dec. 2004;88(12):1543-6.
Lorente, et al. Functional comparison of long and short splice forms of RPTPbeta: implications for glioblastoma treatment. Neuro Oncol. Apr. 2005;7(2):154-63.
Ma, et al. RNase Protection Assay. Methods. Dec. 1996;10(3):273-8.
Martin. 3D database searching in drug design. J Med Chem. Jun. 12, 1992;35(12):2145-54.
Meadows. "Keeping Up with Drug Safety Information," 2006: FDA Consumer Magazine: http://www.fda.gov/fdac/features/2006/306_drugsafety.html accessed Mar. 17, 2008.
Merrifield et al. Solid Phase Peptide Synthesis I. J Am Chem Soc 85:2149-2154 (1963).
Miranker, et al. Functionality maps of binding sites: a multiple copy simultaneous search method. Proteins. 1991;11(1):29-34.
"Morrison, et al., Chimeric Human Antibody Molecules: Mouse Antigen-binding Domains with Human Constant Region Domains, Proc. Natl., Acad. Sci., USA, 1984, 81:6851-55".
Muller, et al. A role for receptor tyrosine phosphatase zeta in glioma cell migration. Oncogene. Oct. 2, 2003;22(43):6661-8.
Muller, et al. Receptor protein tyrosine phosphatase zeta as a therapeutic target for glioblastoma therapy. Expert Opin Ther Targets. Jun. 2004;8(3):211-20.
Navaza. AMoRe: An Automated Package for Molecular Replacement. Acta Cryst. 1994; A50:157-163.
Nawroth, et al. VE-PTP and VE-cadherin ectodomains interact to facilitate regulation of phosphorylation and cell contacts. EMBO J. Sep. 16, 2002;21(18):4885-95.
Nguyen, et al. Cellular interactions in vascular growth and differentiation. Int Rev Cytol. 2001;204:1-48.
Nishibata, et al. Automatic Creation of Drug Candidate Structures Based on Receptor Structure. Starting Point for Artificial Lead Generation. Tetrahedron. 1991; 47(43):8985-8990.
Notice of allowance dated May 10, 2013 for U.S. Appl. No. 13/115,180.
Notice of allowance dated May 19, 2011 for U.S. Appl. No. 11/784,094.
Notice of allowance dated Nov. 13, 2017 for U.S. Appl. No. 15/430,100.
Office action dated Jan. 25, 2013 for U.S. Appl. No. 13/115,180.
Office action dated Apr. 4, 2011 for U.S. Appl. No. 11/784,094.
Office action dated May 5, 2010 for U.S. Appl. No. 11/784,094.
Office action dated Aug. 11, 2016 for U.S. Appl. No. 13/958,990.
Office action dated Sep. 17, 2010 for U.S. Appl. No. 11/784,094.
O'Reilly, et al. Angiostatin: a novel angiogenesis inhibitor that mediates the suppression of metastases by a Lewis lung carcinoma. Cell. Oct. 21, 1994;79(2):315-28.
O'Reilly, et al. Endostatin: an endogenous inhibitor of angiogenesis and tumor growth. Cell. Jan. 24, 1997;88(2):277-85.
Owens, et al. The genetic engineering of monoclonal antibodies. J Immunol Methods. Feb. 10, 1994;168(2):149-65.
Paul. Fundamental Immunology. Chapter 8 Immunogenicity and antigen structure., 3d ed., p. 242, 1993.
Rarey, et al. A fast flexible docking method using an incremental construction algorithm. J Mol Biol. Aug. 23, 1996;261(3):470-89.
Riechmann et al. Reshaping human antibodies for therapy. Nature, 332.6162:323-7 (1988).
Saliba. Heparin in the treatment of burns: a review. Burns. Jun. 2001;27(4):349-58.
Schindelholz, et al. Regulation of CNS and motor axon guidance in *Drosophila* by the receptor tyrosine phosphatase DPTP52F. Development. Nov. 2001;128(21):4371-82.
Schoneberg, et al. Structural basis of G protein-coupled receptor function. Mol Cell Endocrinol. May 25, 1999;151(1-2):181-93.
Sexton. Recent advances in our understanding of peptide hormone receptors and RAMPS. Curr Opin Drug Discov Devel. Sep. 1999;2(5):440-8.
Shintei, et al., Newly Revised Disease and Drugs, Yakuji Nippo Limited, 1986 (Third print), p. 504-510. (English Translation).
Shiojima, et al. Disruption of coordinated cardiac hypertrophy and angiogenesis contributes to the transition to heart failure. J Clin Invest. Aug. 2005;115(8):2108-18.
Shoichet, et al. Lead discovery using molecular docking. Curr Opin Chem Biol. Aug. 2002;6(4):439-46.
Siddiqui, et al. Combination of angiopoietin-1 and vascular endothelial growth factor gene therapy enhances arteriogenesis in the ischemic myocardium. Biochem Biophys Res Commun. Oct. 24, 2003;310(3):1002-9.
Simons. Angiogenesis: where do we stand now? Circulation. Mar. 29, 2005;111(12):1556-66.
Simons, et al. Clinical trials in coronary angiogenesis: issues, problems, consensus: An expert panel summary. Circulation. Sep. 12, 2000;102(11):E73-86.
Skolnick, et al. From genes to protein structure and function: novel applications of computational approaches in the genomic era. Trends Biotechnol. Jan. 2000;18(1):34-9.
Stahl, et al. Detailed analysis of scoring functions for virtual screening. J Med Chem. Mar. 29, 2001;44(7):1035-42.
Stetler-Stevenson. The role of matrix metalloproteinases in tumor invasion, metastasis, and angiogenesis. Surg Oncol Clin N Am. Apr. 2001;10(2):383-92, x.
Suggitt, et al. 50 years of preclinical anticancer drug screening: empirical to target-driven approaches. Clin Cancer Res. Feb. 1, 2005;11(3):971-81.
Suri, et al. Increased vascularization in mice overexpressing angiopoietin-1. Science. Oct. 16, 1998;282(5388):468-71.
Takahashi, et al. Adenoviral-Delivered Angiopoietin-1 Reduces the Infarction and Attenuates the Progression of Cardiac Dysfunction in the Rate Model of Acute Myocardial Infarction. Molecular Therapy. 2003; 8(4):584-592.
Teicher, et al. Potentiation of cytotoxic cancer therapies by TNP-470 alone and with other anti-angiogenic agents. Int J Cancer. Jun. 15, 1994;57(6):920-5.
Thomson, et al., A lymphatic defect causes ocular hypertension and glaucoma in mice, The Journal of Clinical Investigation, Oct. 2014, 124(10):4320-4.
Thurston. Complementary actions of VEGF and angiopoietin-1 on blood vessel growth and leakage. J Anat. Jun. 2002;200(6):575-80.
Thurston, et al. Angiopoietin-1 protects the adult vasculature against plasma leakage. Nat Med. Apr. 2000;6(4):460-3.
Ulbricht, et al. Expression and function of the receptor protein tyrosine phosphatase zeta and its ligand pleiotrophin in human astrocytomas. J Neuropathol Exp Neurol. Dec. 2003;62(12):1265-75.
Vailhe, et al. In vitro models of vasculogenesis and angiogenesis. Lab Invest. Apr. 2001;81(4):439-52.
Vestweber, et al., Molecular Mechanisms That Control Endothelial Cell Contacts, J. Pathol 2000, 190:281-91.
Wang, et al. Expression and characterization of wild type, truncated, and mutant forms of the intracellular region of the receptor-like protein tyrosine phosphatase HPTP beta. J Biol Chem. Aug. 15, 1992;267(23):16696-702.
Weidner, et al. Tumor angiogenesis and metastasis—correlation in invasive breast carcinoma. N Engl J Med. Jan. 3, 1991;324(1):1-8.
Whitaker, et al. Vascular endothelial growth factor receptor-2 and neuropilin-1 form a receptor complex that is responsible for the differential signaling potency of VEGF(165) and VEGF(121). J Biol Chem. Jul. 6, 2001;276(27):25520-31. Epub May 1, 2001.
Winderlich, et al. VE-PTP controls blood vessel development by balancing Tie-2 activity. J Cell Biol. May 18, 2009;185(4):657-71. doi: 10.1083/jcb.200811159.

(56) References Cited

OTHER PUBLICATIONS

Wright, et al. Protein-tyrosine phosphatases in the vessel wall: differential expression after acute arterial injury. Arterioscler Thromb Vasc Biol. May 2000;20(5):1189-98.

Yamakawa, et al. Levels of expression of pleiotrophin and protein tyrosine phosphatase zeta are decreased in human colorectal cancers. Cancer Lett. Jan. 8, 1999;135(1):91-6.

Yancopoulos, et al. Vascular-specific growth factors and blood vessel formation. Nature. Sep. 14, 2000;407(6801):242-8.

Zagzag, et al. Tenascin expression in astrocytomas correlates with angiogenesis. Cancer Res. Feb. 15, 1995;55(4):907-14.

Zhang, et al. Vascular endothelial growth factor and angiopoietins in focal cerebral ischemia. Trends Cardiovasc Med. Feb. 2002;12(2):62-6.

* cited by examiner

SEQUENCE LISTING

```
<160> NUMBER OF SEQ ID NOS: 11

<210> SEQ ID NO 1
<211> LENGTH: 4623
<212> TYPE: DNA
<213> ORGANISM: Homo sapiens
<220> FEATURE:
<221> NAME/KEY: CDS
<222> LOCATION: (1)..(4623)

<400> SEQUENCE: 1 atg ctg agc cat gga gcc ggg ttg gcc ttg tgg atc aca ctg agc ctg      48
Met Leu Ser His Gly Ala Gly Leu Ala Leu Trp Ile Thr Leu Ser Leu
1               5                   10                  15 ctg cag act gga ctg gcg gag cca gag aga tgt aac ttc acc ctg gcg      96
Leu Gln Thr Gly Leu Ala Glu Pro Glu Arg Cys Asn Phe Thr Leu Ala
            20                  25                  30 gag tcc aag gcc tcc agc cat tct gtg tct atc cag tgg aga att ttg     144
Glu Ser Lys Ala Ser Ser His Ser Val Ser Ile Gln Trp Arg Ile Leu
        35                  40                  45 ggc tca ccc tgt aac ttt agc ctc atc tat agc agt gac acc ctg ggg     192
Gly Ser Pro Cys Asn Phe Ser Leu Ile Tyr Ser Ser Asp Thr Leu Gly
    50                  55                  60 gcc gcg ttg tgc cct acc ttt cgg ata gac aac aca tac gga tgt         240
Ala Ala Leu Cys Pro Thr Phe Arg Ile Asp Asn Thr Thr Tyr Gly Cys
65                  70                  75                  80 aac ctt caa gat tta caa gca gga acc atc tat aac ttc aag att att     288
Asn Leu Gln Asp Leu Gln Ala Gly Thr Ile Tyr Asn Phe Lys Ile Ile
                85                  90                  95 tct ctg gat gaa gag aga act gtg gtc ttg caa aca gat cct tta cct     336
Ser Leu Asp Glu Glu Arg Thr Val Val Leu Gln Thr Asp Pro Leu Pro
            100                 105                 110 cct gct agg ttt gga gtc agt aaa gag aag acg tca acc ggc ttg         384
Pro Ala Arg Phe Gly Val Ser Lys Glu Lys Thr Thr Ser Thr Gly Leu
        115                 120                 125 cat gtt tgg tgg act cct tct tcc gga aaa gtc acc tca tat gag gtg     432
```

```
                His Val Trp Trp Thr Pro Ser Ser Gly Lys Val Thr Ser Tyr Glu Val
                    130                 135                 140 caa tta ttt gat gaa aat aac caa aag ata cag ggg gtt caa att caa       480
Gln Leu Phe Asp Glu Asn Asn Gln Lys Ile Gln Gly Val Gln Ile Gln
145                 150                 155                 160 gaa agt act tca tgg aat gaa tac act ttt ttc aat ctc act gct ggt       528
Glu Ser Thr Ser Trp Asn Glu Tyr Thr Phe Phe Asn Leu Thr Ala Gly
                    165                 170                 175 agt aaa tac aat att gcc atc aca gct gtt tct gga gga aaa cgt tct       576
Ser Lys Tyr Asn Ile Ala Ile Thr Ala Val Ser Gly Gly Lys Arg Ser
            180                 185                 190 ttt tca gtt tat acc aat gga tca aca gtg cca tct cca gtg aaa gat       624
Phe Ser Val Tyr Thr Asn Gly Ser Thr Val Pro Ser Pro Val Lys Asp
                195                 200                 205 att ggt att tcc aca aaa gcc aat tct ctc ctg att tcc tgg tcc cat       672
Ile Gly Ile Ser Thr Lys Ala Asn Ser Leu Leu Ile Ser Trp Ser His
210                 215                 220 ggt tct ggg aat gtg gaa cga tac cgg ctg atg cta atg gat aaa ggg       720
Gly Ser Gly Asn Val Glu Arg Tyr Arg Leu Met Leu Met Asp Lys Gly
225                 230                 235                 240 atc cta gtt cat ggc ggt gtt gtg gac aaa cat gct act tcc tat gct       768
Ile Leu Val His Gly Gly Val Val Asp Lys His Ala Thr Ser Tyr Ala
                245                 250                 255 ttt cac ggg ctg acc cct ggc tac ctc tac aac ctc act gtt atg act       816
Phe His Gly Leu Thr Pro Gly Tyr Leu Tyr Asn Leu Thr Val Met Thr
            260                 265                 270 gag gct gca ggg ctg caa aac tac agg tgg aaa cta gtc agg aca gcc       864
Glu Ala Ala Gly Leu Gln Asn Tyr Arg Trp Lys Leu Val Arg Thr Ala
275                 280                 285 ccc atg gaa gtc tca aat ctg aag gta aca aat gat ggc agt ttg acc       912
Pro Met Glu Val Ser Asn Leu Lys Val Thr Asn Asp Gly Ser Leu Thr
290                 295                 300 tct cta aaa gtc aaa tgg caa aga cct cct gga aat gtg gat tct tac       960
Ser Leu Lys Val Lys Trp Gln Arg Pro Pro Gly Asn Val Asp Ser Tyr
305                 310                 315                 320 aat atc acc ctg tct cac aaa ggg acc atc aag gaa tcc aga gta tta      1008
Asn Ile Thr Leu Ser His Lys Gly Thr Ile Lys Glu Ser Arg Val Leu
                325                 330                 335 gca cct tgg att act gaa act cac ttt aaa gag tta gtc ccc ggt cga      1056
Ala Pro Trp Ile Thr Glu Thr His Phe Lys Glu Leu Val Pro Gly Arg
            340                 345                 350 ctt tat caa gtt act gtc agc tgt gtc tct ggt gaa ctg tct gct cag      1104
Leu Tyr Gln Val Thr Val Ser Cys Val Ser Gly Glu Leu Ser Ala Gln
355                 360                 365 aag atg gca gtg ggc aga aca ttc ccc ctg gct gtc ctc cag ctt cgt      1152
Lys Met Ala Val Gly Arg Thr Phe Pro Leu Ala Val Leu Gln Leu Arg
370                 375                 380 gtc aaa cat gcc aat gaa acc tca ctg agt atc atg tgg cag acc cct      1200
Val Lys His Ala Asn Glu Thr Ser Leu Ser Ile Met Trp Gln Thr Pro
385                 390                 395                 400 gta gca gaa tgg gag aaa tac atc att tcc cta gct gac aga gac ctc      1248
Val Ala Glu Trp Glu Lys Tyr Ile Ile Ser Leu Ala Asp Arg Asp Leu
                405                 410                 415 tta ctg atc cac aag tca ctc tcc aaa gat gcc aaa gaa ttc act ttt      1296
Leu Leu Ile His Lys Ser Leu Ser Lys Asp Ala Lys Glu Phe Thr Phe
            420                 425                 430 act gac ctg gtg cct gga cga aaa tac atg gct aca gtc acc agt att      1344
Thr Asp Leu Val Pro Gly Arg Lys Tyr Met Ala Thr Val Thr Ser Ile
435                 440                 445
```

-continued

| | |
|---|---|
| agt gga gac tta aaa aat tcc tct tca gta aaa gga aga aca gtg cct<br>Ser Gly Asp Leu Lys Asn Ser Ser Ser Val Lys Gly Arg Thr Val Pro<br>450                                455                           460 | 1392 |
| gcc caa gtg act gac ttg cat gtg gcc aac caa gga atg acc agt agt<br>Ala Gln Val Thr Asp Leu His Val Ala Asn Gln Gly Met Thr Ser Ser<br>465                              470                           475                       480 | 1440 |
| ctg ttt act aac tgg acc cag gca caa gga gac gta gaa ttt tac caa<br>Leu Phe Thr Asn Trp Thr Gln Ala Gln Gly Asp Val Glu Phe Tyr Gln<br>                        485                           490                          495 | 1488 |
| gtc tta ctg atc cat gaa aat gtg gtc att aaa aat gaa agc atc tcc<br>Val Leu Leu Ile His Glu Asn Val Val Ile Lys Asn Glu Ser Ile Ser<br>                   500                           505                         510 | 1536 |
| agt gag acc agc aga tac agc ttc cac tct ctc aag tcc ggc agc ctg<br>Ser Glu Thr Ser Arg Tyr Ser Phe His Ser Leu Lys Ser Gly Ser Leu<br>             515                           520                         525 | 1584 |
| tac tcc gtg gtg gta aca aca gtg agt gga ggg atc tct tcc cga caa<br>Tyr Ser Val Val Val Thr Thr Val Ser Gly Gly Ile Ser Ser Arg Gln<br>530                                535                           540 | 1632 |
| gtg gtt gtg gag gga aga aca gtc cct tcc agt gtg agt gga gta acg<br>Val Val Val Glu Gly Arg Thr Val Pro Ser Ser Val Ser Gly Val Thr<br>545                                550                           555                       560 | 1680 |
| gtg aac aat tcc ggt cgt aat gac tac ctc agc gtt tcc tgg ctg ctg<br>Val Asn Asn Ser Gly Arg Asn Asp Tyr Leu Ser Val Ser Trp Leu Leu<br>                   565                           570                         575 | 1728 |
| gcg ccc gga gat gtg gat aac tat gag gta aca ttg tct cat gac ggc<br>Ala Pro Gly Asp Val Asp Asn Tyr Glu Val Thr Leu Ser His Asp Gly<br>             580                           585                         590 | 1776 |
| aag gtg gtt cag tcc ctt gtc att gcc aag tct gtc aga gaa tgt tcc<br>Lys Val Val Gln Ser Leu Val Ile Ala Lys Ser Val Arg Glu Cys Ser<br>                   595                           600                         605 | 1824 |
| ttc agc tcc ctc acc cca ggc cgc ctc tac acc gtg acc ata act aca<br>Phe Ser Ser Leu Thr Pro Gly Arg Leu Tyr Thr Val Thr Ile Thr Thr<br>610                                615                           620 | 1872 |
| agg agt ggc aag tat gaa aat cac tcc ttc agc caa gag cgg aca gtg<br>Arg Ser Gly Lys Tyr Glu Asn His Ser Phe Ser Gln Glu Arg Thr Val<br>625                                630                           635                       640 | 1920 |
| cct gac aaa gtc cag gga gtc agt gtt agc aac tca gcc agg agt gac<br>Pro Asp Lys Val Gln Gly Val Ser Val Ser Asn Ser Ala Arg Ser Asp<br>                   645                           650                         655 | 1968 |
| tat tta agg gta tcc tgg gtg cat gcc act gga gac ttt gat cac tat<br>Tyr Leu Arg Val Ser Trp Val His Ala Thr Gly Asp Phe Asp His Tyr<br>             660                           665                         670 | 2016 |
| gaa gtc acc att aaa aac aaa aac aac ttc att caa act aaa agc att<br>Glu Val Thr Ile Lys Asn Lys Asn Asn Phe Ile Gln Thr Lys Ser Ile<br>                   675                           680                         685 | 2064 |
| ccc aag tca gaa aac gaa tgt gta ttt gtt cag cta gtc cct gga cgg<br>Pro Lys Ser Glu Asn Glu Cys Val Phe Val Gln Leu Val Pro Gly Arg<br>             690                           695                         700 | 2112 |
| ttg tac agt gtc act gtt act aca aaa agt gga caa tat gaa gcc aat<br>Leu Tyr Ser Val Thr Val Thr Thr Lys Ser Gly Gln Tyr Glu Ala Asn<br>705                                710                           715                       720 | 2160 |
| gaa caa ggg aat ggg aga aca att cca gag cct gtt aag gat cta aca<br>Glu Gln Gly Asn Gly Arg Thr Ile Pro Glu Pro Val Lys Asp Leu Thr<br>                   725                           730                         735 | 2208 |
| ttg cgc aac agg agc act gag gac ttg cat gtg act tgg tca gga gct<br>Leu Arg Asn Arg Ser Thr Glu Asp Leu His Val Thr Trp Ser Gly Ala<br>             740                           745                         750 | 2256 |
| aat ggg gat gtc gac caa tat gag atc cag ctg ctc ttc aat gac atg<br>Asn Gly Asp Val Asp Gln Tyr Glu Ile Gln Leu Leu Phe Asn Asp Met<br>                   755                           760                         765 | 2304 |

```
aaa gta ttt cct cct ttt cac ctt gta aat acc gca acc gag tat cga      2352
Lys Val Phe Pro Pro Phe His Leu Val Asn Thr Ala Thr Glu Tyr Arg
    770             775                 780 ttt act tcc cta aca cca ggc cgc caa tac aaa att ctt gtc ttg acg      2400
Phe Thr Ser Leu Thr Pro Gly Arg Gln Tyr Lys Ile Leu Val Leu Thr
785             790                 795                 800 att agc ggg gat gta cag cag tca gcc ttc att gag ggc ttc aca gtt      2448
Ile Ser Gly Asp Val Gln Gln Ser Ala Phe Ile Glu Gly Phe Thr Val
                805                 810                 815 cct agt gct gtc aaa aat att cac att tct ccc aat gga gca aca gat      2496
Pro Ser Ala Val Lys Asn Ile His Ile Ser Pro Asn Gly Ala Thr Asp
            820                 825                 830 agc ctg acg gtg aac tgg act cct ggt ggg gga gac gtt gat tcc tac      2544
Ser Leu Thr Val Asn Trp Thr Pro Gly Gly Gly Asp Val Asp Ser Tyr
        835                 840                 845 acg gtg tcg gca ttc agg cac agt caa aag gtt gac tct cag act att      2592
Thr Val Ser Ala Phe Arg His Ser Gln Lys Val Asp Ser Gln Thr Ile
    850                 855                 860 ccc aag cac gtc ttt gag cac acg ttc cac aga ctg gag gcc ggg gag      2640
Pro Lys His Val Phe Glu His Thr Phe His Arg Leu Glu Ala Gly Glu
865                 870                 875                 880 cag tac cag atc atg att gcc tca gtc agc ggg tcc ctg aag aat cag      2688
Gln Tyr Gln Ile Met Ile Ala Ser Val Ser Gly Ser Leu Lys Asn Gln
                885                 890                 895 ata aat gtg gtt ggg cgg aca gtt cca gca tct gtc caa gga gta att      2736
Ile Asn Val Val Gly Arg Thr Val Pro Ala Ser Val Gln Gly Val Ile
            900                 905                 910 gca gac aat gca tac agc agt tat tcc tta ata gta agt tgg caa aaa      2784
Ala Asp Asn Ala Tyr Ser Ser Tyr Ser Leu Ile Val Ser Trp Gln Lys
        915                 920                 925 gct gct ggt gtg gca gaa aga tat gat atc ctg ctt cta act gaa aat      2832
Ala Ala Gly Val Ala Glu Arg Tyr Asp Ile Leu Leu Leu Thr Glu Asn
    930                 935                 940 gga atc ctt ctg cgc aac aca tca gag cca gcc acc act aag caa cac      2880
Gly Ile Leu Leu Arg Asn Thr Ser Glu Pro Ala Thr Thr Lys Gln His
945                 950                 955                 960 aaa ttt gaa gat cta aca cca ggc aag aaa tac aag ata cag atc cta      2928
Lys Phe Glu Asp Leu Thr Pro Gly Lys Lys Tyr Lys Ile Gln Ile Leu
                965                 970                 975 act gtc agt gga ggc ctc ttt agc aag gaa gcc cag act gaa ggc cga      2976
Thr Val Ser Gly Gly Leu Phe Ser Lys Glu Ala Gln Thr Glu Gly Arg
            980                 985                 990 aca gtc cca gca gct gtc acc gac ctg agg atc aca gag aac tcc acc      3024
Thr Val Pro Ala Ala Val Thr Asp Leu Arg Ile Thr Glu Asn Ser Thr
        995                 1000                1005 agg cac ctg tcc ttc cgc tgg acc gcc tca gag ggg gag ctc agc         3069
Arg His Leu Ser Phe Arg Trp Thr Ala Ser Glu Gly Glu Leu Ser
    1010                1015                1020 tgg tac aac atc ttt ttg tac aac cca gat ggg aat ctc cag gag         3114
Trp Tyr Asn Ile Phe Leu Tyr Asn Pro Asp Gly Asn Leu Gln Glu
1025                1030                1035 aga gct caa gtt gac cca cta gtc cag agc ttc tct ttc cag aac         3159
Arg Ala Gln Val Asp Pro Leu Val Gln Ser Phe Ser Phe Gln Asn
            1040                1045                1050 ttg cta caa ggc aga atg tac aag atg gtg att gta act cac agt         3204
Leu Leu Gln Gly Arg Met Tyr Lys Met Val Ile Val Thr His Ser
        1055                1060                1065 ggg gag ctg tct aat gag tct ttc ata ttt ggt aga aca gtc cca         3249
Gly Glu Leu Ser Asn Glu Ser Phe Ile Phe Gly Arg Thr Val Pro
```

|  |  |  |  |  |  |  |  |  |  |  |  |  |
|---|---|---|---|---|---|---|---|---|---|---|---|---|
| gcc | tct | gtg | agt | cat | ctc | agg | ggg | tcc | aat | cgg | aac | acg | aca | gac | 3294 |
| Ala | Ser | Val | Ser | His | Leu | Arg | Gly | Ser | Asn | Arg | Asn | Thr | Thr | Asp |  |
|  | 1085 |  |  |  | 1090 |  |  |  | 1095 |  |  |  |  |  |  |
| agc | ctt | tgg | ttc | aac | tgg | agt | cca | gcc | tct | ggg | gac | ttt | gac | ttt | 3339 |
| Ser | Leu | Trp | Phe | Asn | Trp | Ser | Pro | Ala | Ser | Gly | Asp | Phe | Asp | Phe |  |
|  | 1100 |  |  |  | 1105 |  |  |  | 1110 |  |  |  |  |  |  |
| tat | gag | ctg | att | ctc | tat | aat | ccc | aat | ggc | aca | aag | aag | gaa | aac | 3384 |
| Tyr | Glu | Leu | Ile | Leu | Tyr | Asn | Pro | Asn | Gly | Thr | Lys | Lys | Glu | Asn |  |
|  | 1115 |  |  |  | 1120 |  |  |  | 1125 |  |  |  |  |  |  |
| tgg | aaa | gac | aag | gac | ctg | acg | gag | tgg | cgg | ttt | caa | ggc | ctt | gtt | 3429 |
| Trp | Lys | Asp | Lys | Asp | Leu | Thr | Glu | Trp | Arg | Phe | Gln | Gly | Leu | Val |  |
|  | 1130 |  |  |  | 1135 |  |  |  | 1140 |  |  |  |  |  |  |
| cct | gga | agg | aag | tac | gtg | ctg | tgg | gtg | gta | act | cac | agt | gga | gat | 3474 |
| Pro | Gly | Arg | Lys | Tyr | Val | Leu | Trp | Val | Val | Thr | His | Ser | Gly | Asp |  |
|  | 1145 |  |  |  | 1150 |  |  |  | 1155 |  |  |  |  |  |  |
| ctc | agc | aat | aaa | gtc | aca | gcg | gag | agc | aga | aca | gct | cca | agt | cct | 3519 |
| Leu | Ser | Asn | Lys | Val | Thr | Ala | Glu | Ser | Arg | Thr | Ala | Pro | Ser | Pro |  |
|  | 1160 |  |  |  | 1165 |  |  |  | 1170 |  |  |  |  |  |  |
| ccc | agt | ctt | atg | tca | ttt | gct | gac | att | gca | aac | aca | tcc | ttg | gcc | 3564 |
| Pro | Ser | Leu | Met | Ser | Phe | Ala | Asp | Ile | Ala | Asn | Thr | Ser | Leu | Ala |  |
|  | 1175 |  |  |  | 1180 |  |  |  | 1185 |  |  |  |  |  |  |
| atc | acg | tgg | aaa | ggg | ccc | cca | gac | tgg | aca | gac | tac | aac | gac | ttt | 3609 |
| Ile | Thr | Trp | Lys | Gly | Pro | Pro | Asp | Trp | Thr | Asp | Tyr | Asn | Asp | Phe |  |
|  | 1190 |  |  |  | 1195 |  |  |  | 1200 |  |  |  |  |  |  |
| gag | ctg | cag | tgg | ttg | ccc | aga | gat | gca | ctt | act | gtc | ttc | aac | ccc | 3654 |
| Glu | Leu | Gln | Trp | Leu | Pro | Arg | Asp | Ala | Leu | Thr | Val | Phe | Asn | Pro |  |
|  | 1205 |  |  |  | 1210 |  |  |  | 1215 |  |  |  |  |  |  |
| tac | aac | aac | aga | aaa | tca | gaa | gga | cgc | att | gtg | tat | ggt | ctt | cgt | 3699 |
| Tyr | Asn | Asn | Arg | Lys | Ser | Glu | Gly | Arg | Ile | Val | Tyr | Gly | Leu | Arg |  |
|  | 1220 |  |  |  | 1225 |  |  |  | 1230 |  |  |  |  |  |  |
| cca | ggg | aga | tcc | tat | caa | ttc | aac | gtc | aag | act | gtc | agt | ggt | gat | 3744 |
| Pro | Gly | Arg | Ser | Tyr | Gln | Phe | Asn | Val | Lys | Thr | Val | Ser | Gly | Asp |  |
|  | 1235 |  |  |  | 1240 |  |  |  | 1245 |  |  |  |  |  |  |
| tcc | tgg | aaa | act | tac | agc | aaa | cca | att | ttt | gga | tct | gtg | agg | aca | 3789 |
| Ser | Trp | Lys | Thr | Tyr | Ser | Lys | Pro | Ile | Phe | Gly | Ser | Val | Arg | Thr |  |
|  | 1250 |  |  |  | 1255 |  |  |  | 1260 |  |  |  |  |  |  |
| aag | cct | gac | aag | ata | caa | aac | ctg | cat | tgc | cgg | cct | cag | aac | tcc | 3834 |
| Lys | Pro | Asp | Lys | Ile | Gln | Asn | Leu | His | Cys | Arg | Pro | Gln | Asn | Ser |  |
|  | 1265 |  |  |  | 1270 |  |  |  | 1275 |  |  |  |  |  |  |
| acg | gcc | att | gcc | tgt | tct | tgg | atc | cct | cct | gat | tct | gac | ttt | gat | 3879 |
| Thr | Ala | Ile | Ala | Cys | Ser | Trp | Ile | Pro | Pro | Asp | Ser | Asp | Phe | Asp |  |
|  | 1280 |  |  |  | 1285 |  |  |  | 1290 |  |  |  |  |  |  |
| ggt | tat | agt | att | gaa | tgc | cgg | aaa | atg | gac | acc | caa | gaa | gtt | gag | 3924 |
| Gly | Tyr | Ser | Ile | Glu | Cys | Arg | Lys | Met | Asp | Thr | Gln | Glu | Val | Glu |  |
|  | 1295 |  |  |  | 1300 |  |  |  | 1305 |  |  |  |  |  |  |
| ttt | tcc | aga | aag | ctg | gag | aaa | gaa | aaa | tct | ctg | ctc | aac | atc | atg | 3969 |
| Phe | Ser | Arg | Lys | Leu | Glu | Lys | Glu | Lys | Ser | Leu | Leu | Asn | Ile | Met |  |
|  | 1310 |  |  |  | 1315 |  |  |  | 1320 |  |  |  |  |  |  |
| atg | cta | gtg | ccc | cat | aag | agg | tac | ctg | gtg | tcc | atc | aaa | gtg | cag | 4014 |
| Met | Leu | Val | Pro | His | Lys | Arg | Tyr | Leu | Val | Ser | Ile | Lys | Val | Gln |  |
|  | 1325 |  |  |  | 1330 |  |  |  | 1335 |  |  |  |  |  |  |
| tcg | gcc | ggc | atg | acc | agc | gag | gtg | gtt | gaa | gac | agc | act | atc | aca | 4059 |
| Ser | Ala | Gly | Met | Thr | Ser | Glu | Val | Val | Glu | Asp | Ser | Thr | Ile | Thr |  |
|  | 1340 |  |  |  | 1345 |  |  |  | 1350 |  |  |  |  |  |  |
| atg | ata | gac | cgc | ccc | cct | cct | cca | ccc | cca | cac | att | cgt | gtg | aat | 4104 |
| Met | Ile | Asp | Arg | Pro | Pro | Pro | Pro | Pro | Pro | His | Ile | Arg | Val | Asn |  |
|  | 1355 |  |  |  | 1360 |  |  |  | 1365 |  |  |  |  |  |  |
| gaa | aag | gat | gtg | cta | att | agc | aag | tct | tcc | atc | aac | ttt | act | gtc | 4149 |

```
              Glu  Lys  Asp  Val  Leu  Ile  Ser  Lys  Ser  Ser  Ile  Asn  Phe  Thr  Val
                   1370                1375               1380 aac  tgc  agc  tgg  ttc  agc  gac  acc  aat  gga  gct  gtg  aaa  tac  ttc            4194
Asn  Cys  Ser  Trp  Phe  Ser  Asp  Thr  Asn  Gly  Ala  Val  Lys  Tyr  Phe
    1385                1390                1395 aca  gtg  gtg  gtg  aga  gag  gct  gat  ggc  agt  gat  gag  ctg  aag  cca            4239
Thr  Val  Val  Val  Arg  Glu  Ala  Asp  Gly  Ser  Asp  Glu  Leu  Lys  Pro
    1400                1405                1410 gaa  cag  cag  cac  cct  ctc  cct  tcc  tac  ctg  gag  tac  agg  cac  aat            4284
Glu  Gln  Gln  His  Pro  Leu  Pro  Ser  Tyr  Leu  Glu  Tyr  Arg  His  Asn
    1415                1420                1425 gcc  tcc  att  cgg  gtg  tat  cag  act  aat  tat  ttt  gcc  agc  aaa  tgt            4329
Ala  Ser  Ile  Arg  Val  Tyr  Gln  Thr  Asn  Tyr  Phe  Ala  Ser  Lys  Cys
    1430                1435                1440 gcc  gaa  aat  cct  aac  agc  aac  tcc  aag  agt  ttt  aac  att  aag  ctt            4374
Ala  Glu  Asn  Pro  Asn  Ser  Asn  Ser  Lys  Ser  Phe  Asn  Ile  Lys  Leu
    1445                1450                1455 gga  gca  gag  atg  gag  agc  cta  ggt  gga  aaa  tgc  gat  ccc  act  cag            4419
Gly  Ala  Glu  Met  Glu  Ser  Leu  Gly  Gly  Lys  Cys  Asp  Pro  Thr  Gln
    1460                1465                1470 caa  aaa  ttc  tgt  gat  gga  cca  ctg  aag  cca  cac  act  gcc  tac  aga            4464
Gln  Lys  Phe  Cys  Asp  Gly  Pro  Leu  Lys  Pro  His  Thr  Ala  Tyr  Arg
    1475                1480                1485 atc  agc  att  cga  gct  ttt  aca  cag  ctc  ttt  gat  gag  gac  ctg  aag            4509
Ile  Ser  Ile  Arg  Ala  Phe  Thr  Gln  Leu  Phe  Asp  Glu  Asp  Leu  Lys
    1490                1495                1500 gaa  ttc  aca  aag  cca  ctc  tat  tca  gac  aca  ttt  ttt  tct  tta  ccc            4554
Glu  Phe  Thr  Lys  Pro  Leu  Tyr  Ser  Asp  Thr  Phe  Phe  Ser  Leu  Pro
    1505                1510                1515 atc  act  act  gaa  tca  gag  ccc  ttg  ttt  gga  gct  att  gaa  cgc  ggc            4599
Ile  Thr  Thr  Glu  Ser  Glu  Pro  Leu  Phe  Gly  Ala  Ile  Glu  Arg  Gly
    1520                1525                1530 cgc  cat  cat  cat  cat  cat  cac  gga                                                4623
Arg  His  His  His  His  His  His  Gly
    1535                1540

<210> SEQ ID NO 2
<211> LENGTH: 1541
<212> TYPE: PRT
<213> ORGANISM: Homo sapiens

<400> SEQUENCE: 2

Met  Leu  Ser  His  Gly  Ala  Gly  Leu  Ala  Leu  Trp  Ile  Thr  Leu  Ser  Leu
  1                5                  10                 15

Leu  Gln  Thr  Gly  Leu  Ala  Glu  Pro  Glu  Arg  Cys  Asn  Phe  Thr  Leu  Ala
                 20                  25                 30

Glu  Ser  Lys  Ala  Ser  Ser  His  Ser  Val  Ser  Ile  Gln  Trp  Arg  Ile  Leu
             35                  40                 45

Gly  Ser  Pro  Cys  Asn  Phe  Ser  Leu  Ile  Tyr  Ser  Ser  Asp  Thr  Leu  Gly
         50                  55                 60

Ala  Ala  Leu  Cys  Pro  Thr  Phe  Arg  Ile  Asp  Asn  Thr  Thr  Tyr  Gly  Cys
 65                  70                 75                  80

Asn  Leu  Gln  Asp  Leu  Gln  Ala  Gly  Thr  Ile  Tyr  Asn  Phe  Lys  Ile  Ile
                 85                  90                 95

Ser  Leu  Asp  Glu  Glu  Arg  Thr  Val  Val  Leu  Gln  Thr  Asp  Pro  Leu  Pro
                100                 105                110

Pro  Ala  Arg  Phe  Gly  Val  Ser  Lys  Glu  Lys  Thr  Thr  Ser  Thr  Gly  Leu
            115                 120                 125
```

-continued

```
His Val Trp Trp Thr Pro Ser Ser Gly Lys Val Thr Ser Tyr Glu Val
130                 135                 140

Gln Leu Phe Asp Glu Asn Asn Gln Lys Ile Gln Gly Val Gln Ile Gln
145                 150                 155                 160

Glu Ser Thr Ser Trp Asn Glu Tyr Thr Phe Phe Asn Leu Thr Ala Gly
                165                 170                 175

Ser Lys Tyr Asn Ile Ala Ile Thr Ala Val Ser Gly Gly Lys Arg Ser
            180                 185                 190

Phe Ser Val Tyr Thr Asn Gly Ser Thr Val Pro Ser Pro Val Lys Asp
        195                 200                 205

Ile Gly Ile Ser Thr Lys Ala Asn Ser Leu Leu Ile Ser Trp Ser His
210                 215                 220

Gly Ser Gly Asn Val Glu Arg Tyr Arg Leu Met Leu Met Asp Lys Gly
225                 230                 235                 240

Ile Leu Val His Gly Val Val Asp Lys His Ala Thr Ser Tyr Ala
                245                 250                 255

Phe His Gly Leu Thr Pro Gly Tyr Leu Tyr Asn Leu Thr Val Met Thr
                260                 265                 270

Glu Ala Ala Gly Leu Gln Asn Tyr Arg Trp Lys Leu Val Arg Thr Ala
            275                 280                 285

Pro Met Glu Val Ser Asn Leu Lys Val Thr Asn Asp Gly Ser Leu Thr
        290                 295                 300

Ser Leu Lys Val Lys Trp Gln Arg Pro Pro Gly Asn Val Asp Ser Tyr
305                 310                 315                 320

Asn Ile Thr Leu Ser His Lys Gly Thr Ile Lys Glu Ser Arg Val Leu
                325                 330                 335

Ala Pro Trp Ile Thr Glu Thr His Phe Lys Glu Leu Val Pro Gly Arg
                340                 345                 350

Leu Tyr Gln Val Thr Val Ser Cys Val Ser Gly Glu Leu Ser Ala Gln
            355                 360                 365

Lys Met Ala Val Gly Arg Thr Phe Pro Leu Ala Val Leu Gln Leu Arg
        370                 375                 380

Val Lys His Ala Asn Glu Thr Ser Leu Ser Ile Met Trp Gln Thr Pro
385                 390                 395                 400

Val Ala Glu Trp Glu Lys Tyr Ile Ile Ser Leu Ala Asp Arg Asp Leu
                405                 410                 415

Leu Leu Ile His Lys Ser Leu Ser Lys Asp Ala Lys Glu Phe Thr Phe
                420                 425                 430

Thr Asp Leu Val Pro Gly Arg Lys Tyr Met Ala Thr Val Thr Ser Ile
            435                 440                 445

Ser Gly Asp Leu Lys Asn Ser Ser Val Lys Gly Arg Thr Val Pro
        450                 455                 460

Ala Gln Val Thr Asp Leu His Val Ala Asn Gln Gly Met Thr Ser Ser
465                 470                 475                 480

Leu Phe Thr Asn Trp Thr Gln Ala Gln Gly Asp Val Glu Phe Tyr Gln
                485                 490                 495

Val Leu Leu Ile His Glu Asn Val Val Ile Lys Asn Glu Ser Ile Ser
                500                 505                 510

Ser Glu Thr Ser Arg Tyr Ser Phe His Ser Leu Lys Ser Gly Ser Leu
            515                 520                 525

Tyr Ser Val Val Thr Thr Val Ser Gly Ile Ser Ser Arg Gln
        530                 535                 540

Val Val Val Glu Gly Arg Thr Val Pro Ser Ser Val Ser Gly Val Thr
```

```
545                 550                 555                 560
Val Asn Ser Gly Arg Asn Asp Tyr Leu Ser Val Ser Trp Leu Leu
                565                 570                 575

Ala Pro Gly Asp Val Asp Asn Tyr Glu Val Thr Leu Ser His Asp Gly
            580                 585                 590

Lys Val Gln Ser Leu Val Ile Ala Lys Ser Val Arg Glu Cys Ser
            595                 600                 605

Phe Ser Ser Leu Thr Pro Gly Arg Leu Tyr Thr Val Thr Ile Thr Thr
        610                 615                 620

Arg Ser Gly Lys Tyr Glu Asn His Ser Phe Ser Gln Glu Arg Thr Val
625                 630                 635                 640

Pro Asp Lys Val Gln Gly Val Ser Val Ser Asn Ser Ala Arg Ser Asp
                645                 650                 655

Tyr Leu Arg Val Ser Trp Val His Ala Thr Gly Asp Phe Asp His Tyr
            660                 665                 670

Glu Val Thr Ile Lys Asn Lys Asn Asn Phe Ile Gln Thr Lys Ser Ile
        675                 680                 685

Pro Lys Ser Glu Asn Glu Cys Val Phe Val Gln Leu Val Pro Gly Arg
    690                 695                 700

Leu Tyr Ser Val Thr Val Thr Thr Lys Ser Gly Gln Tyr Glu Ala Asn
705                 710                 715                 720

Glu Gln Gly Asn Gly Arg Thr Ile Pro Glu Pro Val Lys Asp Leu Thr
                725                 730                 735

Leu Arg Asn Arg Ser Thr Glu Asp Leu His Val Thr Trp Ser Gly Ala
            740                 745                 750

Asn Gly Asp Val Asp Gln Tyr Glu Ile Gln Leu Leu Phe Asn Asp Met
        755                 760                 765

Lys Val Phe Pro Pro Phe His Leu Val Asn Thr Ala Thr Glu Tyr Arg
    770                 775                 780

Phe Thr Ser Leu Thr Pro Gly Arg Gln Tyr Lys Ile Leu Val Leu Thr
785                 790                 795                 800

Ile Ser Gly Asp Val Gln Gln Ser Ala Phe Ile Glu Gly Phe Thr Val
                805                 810                 815

Pro Ser Ala Val Lys Asn Ile His Ile Ser Pro Asn Gly Ala Thr Asp
            820                 825                 830

Ser Leu Thr Val Asn Trp Thr Pro Gly Gly Gly Asp Val Asp Ser Tyr
        835                 840                 845

Thr Val Ser Ala Phe Arg His Ser Gln Lys Val Asp Ser Gln Thr Ile
    850                 855                 860

Pro Lys His Val Phe Glu His Thr Phe His Arg Leu Glu Ala Gly Glu
865                 870                 875                 880

Gln Tyr Gln Ile Met Ile Ala Ser Val Ser Gly Ser Leu Lys Asn Gln
                885                 890                 895

Ile Asn Val Val Gly Arg Thr Val Pro Ala Ser Val Gln Gly Val Ile
            900                 905                 910

Ala Asp Asn Ala Tyr Ser Ser Tyr Ser Leu Ile Val Ser Trp Gln Lys
        915                 920                 925

Ala Ala Gly Val Ala Glu Arg Tyr Asp Ile Leu Leu Leu Thr Glu Asn
    930                 935                 940

Gly Ile Leu Leu Arg Asn Thr Ser Glu Pro Ala Thr Thr Lys Gln His
945                 950                 955                 960

Lys Phe Glu Asp Leu Thr Pro Gly Lys Lys Tyr Lys Ile Gln Ile Leu
                965                 970                 975
```

```
Thr Val Ser Gly Gly Leu Phe Ser Lys Glu Ala Gln Thr Glu Gly Arg
            980             985              990

Thr Val Pro Ala Ala Val Thr Asp Leu Arg Ile Thr Glu Asn Ser Thr
            995             1000             1005

Arg His Leu Ser Phe Arg Trp Thr Ala Ser Glu Gly Glu Leu Ser
    1010             1015             1020

Trp Tyr Asn Ile Phe Leu Tyr Asn Pro Asp Gly Asn Leu Gln Glu
    1025             1030             1035

Arg Ala Gln Val Asp Pro Leu Val Gln Ser Phe Ser Phe Gln Asn
    1040             1045             1050

Leu Leu Gln Gly Arg Met Tyr Lys Met Val Ile Val Thr His Ser
    1055             1060             1065

Gly Glu Leu Ser Asn Glu Ser Phe Ile Phe Gly Arg Thr Val Pro
    1070             1075             1080

Ala Ser Val Ser His Leu Arg Gly Ser Asn Arg Asn Thr Thr Asp
    1085             1090             1095

Ser Leu Trp Phe Asn Trp Ser Pro Ala Ser Gly Asp Phe Asp Phe
    1100             1105             1110

Tyr Glu Leu Ile Leu Tyr Asn Pro Asn Gly Thr Lys Lys Glu Asn
    1115             1120             1125

Trp Lys Asp Lys Asp Leu Thr Glu Trp Arg Phe Gln Gly Leu Val
    1130             1135             1140

Pro Gly Arg Lys Tyr Val Leu Trp Val Val Thr His Ser Gly Asp
    1145             1150             1155

Leu Ser Asn Lys Val Thr Ala Glu Ser Arg Thr Ala Pro Ser Pro
    1160             1165             1170

Pro Ser Leu Met Ser Phe Ala Asp Ile Ala Asn Thr Ser Leu Ala
    1175             1180             1185

Ile Thr Trp Lys Gly Pro Pro Asp Trp Thr Asp Tyr Asn Asp Phe
    1190             1195             1200

Glu Leu Gln Trp Leu Pro Arg Asp Ala Leu Thr Val Phe Asn Pro
    1205             1210             1215

Tyr Asn Asn Arg Lys Ser Glu Gly Arg Ile Val Tyr Gly Leu Arg
    1220             1225             1230

Pro Gly Arg Ser Tyr Gln Phe Asn Val Lys Thr Val Ser Gly Asp
    1235             1240             1245

Ser Trp Lys Thr Tyr Ser Lys Pro Ile Phe Gly Ser Val Arg Thr
    1250             1255             1260

Lys Pro Asp Lys Ile Gln Asn Leu His Cys Arg Pro Gln Asn Ser
    1265             1270             1275

Thr Ala Ile Ala Cys Ser Trp Ile Pro Pro Asp Ser Asp Phe Asp
    1280             1285             1290

Gly Tyr Ser Ile Glu Cys Arg Lys Met Asp Thr Gln Glu Val Glu
    1295             1300             1305

Phe Ser Arg Lys Leu Glu Lys Glu Lys Ser Leu Leu Asn Ile Met
    1310             1315             1320

Met Leu Val Pro His Lys Arg Tyr Leu Val Ser Ile Lys Val Gln
    1325             1330             1335

Ser Ala Gly Met Thr Ser Glu Val Val Glu Asp Ser Thr Ile Thr
    1340             1345             1350

Met Ile Asp Arg Pro Pro Pro Pro Pro His Ile Arg Val Asn
    1355             1360             1365
```

```
Glu Lys Asp Val Leu Ile Ser Lys Ser Ser Ile Asn Phe Thr Val
    1370                1375                1380

Asn Cys Ser Trp Phe Ser Asp Thr Asn Gly Ala Val Lys Tyr Phe
    1385                1390                1395

Thr Val Val Val Arg Glu Ala Asp Gly Ser Asp Glu Leu Lys Pro
    1400                1405                1410

Glu Gln Gln His Pro Leu Pro Ser Tyr Leu Glu Tyr Arg His Asn
    1415                1420                1425

Ala Ser Ile Arg Val Tyr Gln Thr Asn Tyr Phe Ala Ser Lys Cys
    1430                1435                1440

Ala Glu Asn Pro Asn Ser Asn Ser Lys Ser Phe Asn Ile Lys Leu
    1445                1450                1455

Gly Ala Glu Met Glu Ser Leu Gly Gly Lys Cys Asp Pro Thr Gln
    1460                1465                1470

Gln Lys Phe Cys Asp Gly Pro Leu Lys Pro His Thr Ala Tyr Arg
    1475                1480                1485

Ile Ser Ile Arg Ala Phe Thr Gln Leu Phe Asp Glu Asp Leu Lys
    1490                1495                1500

Glu Phe Thr Lys Pro Leu Tyr Ser Asp Thr Phe Phe Ser Leu Pro
    1505                1510                1515

Ile Thr Thr Glu Ser Glu Pro Leu Phe Gly Ala Ile Glu Arg Gly
    1520                1525                1530

Arg His His His His His Gly
    1535                1540

<210> SEQ ID NO 3
<211> LENGTH: 1621
<212> TYPE: PRT
<213> ORGANISM: Homo sapiens

<400> SEQUENCE: 3

Met Leu Ser His Gly Ala Gly Leu Ala Leu Trp Ile Thr Leu Ser Leu
1               5                   10                  15

Leu Gln Thr Gly Leu Ala Glu Pro Glu Arg Cys Asn Phe Thr Leu Ala
            20                  25                  30

Glu Ser Lys Ala Ser Ser His Ser Val Ser Ile Gln Trp Arg Ile Leu
        35                  40                  45

Gly Ser Pro Cys Asn Phe Ser Leu Ile Tyr Ser Ser Asp Thr Leu Gly
    50                  55                  60

Ala Ala Leu Cys Pro Thr Phe Arg Ile Asp Asn Thr Thr Tyr Gly Cys
65                  70                  75                  80

Asn Leu Gln Asp Leu Gln Ala Gly Thr Ile Tyr Asn Phe Lys Ile Ile
                85                  90                  95

Ser Leu Asp Glu Glu Arg Thr Val Val Leu Gln Thr Asp Pro Leu Pro
            100                 105                 110

Pro Ala Arg Phe Gly Val Ser Lys Glu Lys Thr Thr Ser Thr Gly Leu
        115                 120                 125

His Val Trp Trp Thr Pro Ser Ser Gly Lys Val Thr Ser Tyr Glu Val
    130                 135                 140

Gln Leu Phe Asp Glu Asn Asn Gln Lys Ile Gln Gly Val Gln Ile Gln
145                 150                 155                 160

Glu Ser Thr Ser Trp Asn Glu Tyr Thr Phe Phe Asn Leu Thr Ala Gly
                165                 170                 175

Ser Lys Tyr Asn Ile Ala Ile Thr Ala Val Ser Gly Gly Lys Arg Ser
            180                 185                 190
```

```
Phe Ser Val Tyr Thr Asn Gly Ser Thr Val Pro Ser Pro Val Lys Asp
        195                 200                 205

Ile Gly Ile Ser Thr Lys Ala Asn Ser Leu Leu Ile Ser Trp Ser His
210                 215                 220

Gly Ser Gly Asn Val Glu Arg Tyr Arg Leu Met Leu Met Asp Lys Gly
225                 230                 235                 240

Ile Leu Val His Gly Val Val Asp Lys His Ala Thr Ser Tyr Ala
                    245                 250                 255

Phe His Gly Leu Ser Pro Gly Tyr Leu Tyr Asn Leu Thr Val Met Thr
            260                 265                 270

Glu Ala Ala Gly Leu Gln Asn Tyr Arg Trp Lys Leu Val Arg Thr Ala
                275                 280                 285

Pro Met Glu Val Ser Asn Leu Lys Val Thr Asn Asp Gly Ser Leu Thr
        290                 295                 300

Ser Leu Lys Val Lys Trp Gln Arg Pro Pro Gly Asn Val Asp Ser Tyr
305                 310                 315                 320

Asn Ile Thr Leu Ser His Lys Gly Thr Ile Lys Glu Ser Arg Val Leu
                325                 330                 335

Ala Pro Trp Ile Thr Glu Thr His Phe Lys Glu Leu Val Pro Gly Arg
                340                 345                 350

Leu Tyr Gln Val Thr Val Ser Cys Val Ser Gly Glu Leu Ser Ala Gln
            355                 360                 365

Lys Met Ala Val Gly Arg Thr Phe Pro Asp Lys Val Ala Asn Leu Glu
370                 375                 380

Ala Asn Asn Asn Gly Arg Met Arg Ser Leu Val Ser Trp Ser Pro
385                 390                 395                 400

Pro Ala Gly Asp Trp Glu Gln Tyr Arg Ile Leu Leu Phe Asn Asp Ser
                405                 410                 415

Val Val Leu Leu Asn Ile Thr Val Gly Lys Glu Glu Thr Gln Tyr Val
                420                 425                 430

Met Asp Asp Thr Gly Leu Val Pro Gly Arg Gln Tyr Glu Val Glu Val
        435                 440                 445

Ile Val Glu Ser Gly Asn Leu Lys Asn Ser Glu Arg Cys Gln Gly Arg
    450                 455                 460

Thr Val Pro Leu Ala Val Leu Gln Leu Arg Val Lys His Ala Asn Glu
465                 470                 475                 480

Thr Ser Leu Ser Ile Met Trp Gln Thr Pro Val Ala Glu Trp Glu Lys
                485                 490                 495

Tyr Ile Ile Ser Leu Ala Asp Arg Asp Leu Leu Leu Ile His Lys Ser
                500                 505                 510

Leu Ser Lys Asp Ala Lys Glu Phe Thr Phe Thr Asp Leu Val Pro Gly
            515                 520                 525

Arg Lys Tyr Met Ala Thr Val Thr Ser Ile Ser Gly Asp Leu Lys Asn
        530                 535                 540

Ser Ser Ser Val Lys Gly Arg Thr Val Pro Ala Gln Val Thr Asp Leu
545                 550                 555                 560

His Val Ala Asn Gln Gly Met Thr Ser Ser Leu Phe Thr Asn Trp Thr
                565                 570                 575

Gln Ala Gln Gly Asp Val Glu Phe Tyr Gln Val Leu Leu Ile His Glu
            580                 585                 590

Asn Val Val Ile Lys Asn Glu Ser Ile Ser Ser Glu Thr Ser Arg Tyr
                595                 600                 605
```

-continued

```
Ser Phe His Ser Leu Lys Ser Gly Ser Leu Tyr Ser Val Val Thr
610                 615                 620

Thr Val Ser Gly Gly Ile Ser Ser Arg Gln Val Val Glu Gly Arg
625                 630                 635                 640

Thr Val Pro Ser Val Ser Gly Val Thr Val Asn Asn Ser Gly Arg
                645                 650                 655

Asn Asp Tyr Leu Ser Val Ser Trp Leu Leu Ala Pro Gly Asp Val Asp
            660                 665                 670

Asn Tyr Glu Val Thr Leu Ser His Asp Gly Lys Val Val Gln Ser Leu
        675                 680                 685

Val Ile Ala Lys Ser Val Arg Glu Cys Ser Phe Ser Ser Leu Thr Pro
690                 695                 700

Gly Arg Leu Tyr Thr Val Thr Ile Thr Thr Arg Ser Gly Lys Tyr Glu
705                 710                 715                 720

Asn His Ser Phe Ser Gln Glu Arg Thr Val Pro Asp Lys Val Gln Gly
                725                 730                 735

Val Ser Val Ser Asn Ser Ala Arg Ser Asp Tyr Leu Arg Val Ser Trp
            740                 745                 750

Val His Ala Thr Gly Asp Phe Asp His Tyr Glu Val Thr Ile Lys Asn
        755                 760                 765

Lys Asn Asn Phe Ile Gln Thr Lys Ser Ile Pro Lys Ser Glu Asn Glu
770                 775                 780

Cys Val Phe Val Gln Leu Val Pro Gly Arg Leu Tyr Ser Val Thr Val
785                 790                 795                 800

Thr Thr Lys Ser Gly Gln Tyr Glu Ala Asn Glu Gln Gly Asn Gly Arg
                805                 810                 815

Thr Ile Pro Glu Pro Val Lys Asp Leu Thr Leu Arg Asn Arg Ser Thr
            820                 825                 830

Glu Asp Leu His Val Thr Trp Ser Gly Ala Asn Gly Asp Val Asp Gln
        835                 840                 845

Tyr Glu Ile Gln Leu Leu Phe Asn Asp Met Lys Val Phe Pro Pro Phe
850                 855                 860

His Leu Val Asn Thr Ala Thr Glu Tyr Arg Phe Thr Ser Leu Thr Pro
865                 870                 875                 880

Gly Arg Gln Tyr Lys Ile Leu Val Leu Thr Ile Ser Gly Asp Val Gln
                885                 890                 895

Gln Ser Ala Phe Ile Glu Gly Phe Thr Val Pro Ser Ala Val Lys Asn
            900                 905                 910

Ile His Ile Ser Pro Asn Gly Ala Thr Asp Ser Leu Thr Val Asn Trp
        915                 920                 925

Thr Pro Gly Gly Gly Asp Val Asp Ser Tyr Thr Val Ser Ala Phe Arg
930                 935                 940

His Ser Gln Lys Val Asp Ser Gln Thr Ile Pro Lys His Val Phe Glu
945                 950                 955                 960

His Thr Phe His Arg Leu Glu Ala Gly Glu Gln Tyr Gln Ile Met Ile
                965                 970                 975

Ala Ser Val Ser Gly Ser Leu Lys Asn Gln Ile Asn Val Val Gly Arg
            980                 985                 990

Thr Val Pro Ala Ser Val Gln Gly Val Ile Ala Asp Asn Ala Tyr Ser
        995                 1000                1005

Ser Tyr Ser Leu Ile Val Ser Trp Gln Lys Ala Ala Gly Val Ala
        1010                1015                1020

Glu Arg Tyr Asp Ile Leu Leu Leu Thr Glu Asn Gly Ile Leu Leu
```

```
              1025                1030                1035

Arg Asn Thr Ser Glu Pro Ala Thr Thr Lys Gln His Lys Phe Glu
    1040                1045                1050

Asp Leu Thr Pro Gly Lys Lys Tyr Lys Ile Gln Ile Leu Thr Val
    1055                1060                1065

Ser Gly Gly Leu Phe Ser Lys Glu Ala Gln Thr Glu Gly Arg Thr
    1070                1075                1080

Val Pro Ala Ala Val Thr Asp Leu Arg Ile Thr Glu Asn Ser Thr
    1085                1090                1095

Arg His Leu Ser Phe Arg Trp Thr Ala Ser Glu Gly Glu Leu Ser
    1100                1105                1110

Trp Tyr Asn Ile Phe Leu Tyr Asn Pro Asp Gly Asn Leu Gln Glu
    1115                1120                1125

Arg Ala Gln Val Asp Pro Leu Val Gln Ser Phe Ser Phe Gln Asn
    1130                1135                1140

Leu Leu Gln Gly Arg Met Tyr Lys Met Val Ile Val Thr His Ser
    1145                1150                1155

Gly Glu Leu Ser Asn Glu Ser Phe Ile Phe Gly Arg Thr Val Pro
    1160                1165                1170

Ala Ser Val Ser His Leu Arg Gly Ser Asn Arg Asn Thr Thr Asp
    1175                1180                1185

Ser Leu Trp Phe Asn Trp Ser Pro Ala Ser Gly Asp Phe Asp Phe
    1190                1195                1200

Tyr Glu Leu Ile Leu Tyr Asn Pro Asn Gly Thr Lys Lys Glu Asn
    1205                1210                1215

Trp Lys Asp Lys Asp Leu Thr Glu Trp Arg Phe Gln Gly Leu Val
    1220                1225                1230

Pro Gly Arg Lys Tyr Val Leu Trp Val Val Thr His Ser Gly Asp
    1235                1240                1245

Leu Ser Asn Lys Val Thr Ala Glu Ser Arg Thr Ala Pro Ser Pro
    1250                1255                1260

Pro Ser Leu Met Ser Phe Ala Asp Ile Ala Asn Thr Ser Leu Ala
    1265                1270                1275

Ile Thr Trp Lys Gly Pro Pro Asp Trp Thr Asp Tyr Asn Asp Phe
    1280                1285                1290

Glu Leu Gln Trp Leu Pro Arg Asp Ala Leu Thr Val Phe Asn Pro
    1295                1300                1305

Tyr Asn Asn Arg Lys Ser Glu Gly Arg Ile Val Tyr Gly Leu Arg
    1310                1315                1320

Pro Gly Arg Ser Tyr Gln Phe Asn Val Lys Thr Val Ser Gly Asp
    1325                1330                1335

Ser Trp Lys Thr Tyr Ser Lys Pro Ile Phe Gly Ser Val Arg Thr
    1340                1345                1350

Lys Pro Asp Lys Ile Gln Asn Leu His Cys Arg Pro Gln Asn Ser
    1355                1360                1365

Thr Ala Ile Ala Cys Ser Trp Ile Pro Pro Asp Ser Asp Phe Asp
    1370                1375                1380

Gly Tyr Ser Ile Glu Cys Arg Lys Met Asp Thr Gln Glu Val Glu
    1385                1390                1395

Phe Ser Arg Lys Leu Glu Lys Glu Lys Ser Leu Leu Asn Ile Met
    1400                1405                1410

Met Leu Val Pro His Lys Arg Tyr Leu Val Ser Ile Lys Val Gln
    1415                1420                1425
```

```
Ser Ala Gly Met Thr Ser Glu Val Val Glu Asp Ser Thr Ile Thr
    1430            1435                1440

Met Ile Asp Arg Pro Pro Pro Pro Pro His Ile Arg Val Asn
    1445            1450                1455

Glu Lys Asp Val Leu Ile Ser Lys Ser Ser Ile Asn Phe Thr Val
    1460            1465                1470

Asn Cys Ser Trp Phe Ser Asp Thr Asn Gly Ala Val Lys Tyr Phe
    1475            1480                1485

Thr Val Val Val Arg Glu Ala Asp Gly Ser Asp Glu Leu Lys Pro
    1490            1495                1500

Glu Gln Gln His Pro Leu Pro Ser Tyr Leu Glu Tyr Arg His Asn
    1505            1510                1515

Ala Ser Ile Arg Val Tyr Gln Thr Asn Tyr Phe Ala Ser Lys Cys
    1520            1525                1530

Ala Glu Asn Pro Asn Ser Asn Ser Lys Ser Phe Asn Ile Lys Leu
    1535            1540                1545

Gly Ala Glu Met Glu Ser Leu Gly Gly Lys Arg Asp Pro Thr Gln
    1550            1555                1560

Gln Lys Phe Cys Asp Gly Pro Leu Lys Pro His Thr Ala Tyr Arg
    1565            1570                1575

Ile Ser Ile Arg Ala Phe Thr Gln Leu Phe Asp Glu Asp Leu Lys
    1580            1585                1590

Glu Phe Thr Lys Pro Leu Tyr Ser Asp Thr Phe Phe Ser Leu Pro
    1595            1600                1605

Ile Thr Thr Glu Ser Glu Pro Leu Phe Gly Ala Ile Glu
    1610            1615                1620

<210> SEQ ID NO 4
<211> LENGTH: 775
<212> TYPE: PRT
<213> ORGANISM: Homo sapiens

<400> SEQUENCE: 4

Met Leu Ser His Gly Ala Gly Leu Ala Leu Trp Ile Thr Leu Ser Leu
1               5                   10                  15

Leu Gln Thr Gly Leu Ala Glu Pro Glu Arg Cys Asn Phe Thr Leu Ala
                20                  25                  30

Glu Ser Lys Ala Ser Ser His Ser Val Ser Ile Gln Trp Arg Ile Leu
            35                  40                  45

Gly Ser Pro Cys Asn Phe Ser Leu Ile Tyr Ser Ser Asp Thr Leu Gly
        50                  55                  60

Ala Ala Leu Cys Pro Thr Phe Arg Ile Asp Asn Thr Thr Tyr Gly Cys
65                  70                  75                  80

Asn Leu Gln Asp Leu Gln Ala Gly Thr Ile Tyr Asn Phe Lys Ile Ile
                85                  90                  95

Ser Leu Asp Glu Glu Arg Thr Val Val Leu Gln Thr Asp Pro Leu Pro
            100                 105                 110

Pro Ala Arg Phe Gly Val Ser Lys Glu Lys Thr Thr Ser Thr Gly Leu
        115                 120                 125

His Val Trp Trp Thr Pro Ser Ser Gly Lys Val Thr Ser Tyr Glu Val
    130                 135                 140

Gln Leu Phe Asp Glu Asn Asn Gln Lys Ile Gln Gly Val Gln Ile Gln
145                 150                 155                 160

Glu Ser Thr Ser Trp Asn Glu Tyr Thr Phe Phe Asn Leu Thr Ala Gly
```

```
                165                 170                 175
Ser Lys Tyr Asn Ile Ala Ile Thr Ala Val Ser Gly Gly Lys Arg Ser
                180                 185                 190

Phe Ser Val Tyr Thr Asn Gly Ser Thr Val Pro Ser Pro Val Lys Asp
                195                 200                 205

Ile Gly Ile Ser Thr Lys Ala Asn Ser Leu Leu Ile Ser Trp Ser His
                210                 215                 220

Gly Ser Gly Asn Val Glu Arg Tyr Arg Leu Met Leu Met Asp Lys Gly
225                 230                 235                 240

Ile Leu Val His Gly Val Val Asp Lys His Ala Thr Ser Tyr Ala
                    245                 250                 255

Phe His Gly Leu Thr Pro Gly Tyr Leu Tyr Asn Leu Thr Val Met Thr
                260                 265                 270

Glu Ala Ala Gly Leu Gln Asn Tyr Arg Trp Lys Leu Val Arg Thr Ala
                275                 280                 285

Pro Met Glu Val Ser Asn Leu Lys Val Thr Asn Asp Gly Ser Leu Thr
                290                 295                 300

Ser Leu Lys Val Lys Trp Gln Arg Pro Pro Gly Asn Val Asp Ser Tyr
305                 310                 315                 320

Asn Ile Thr Leu Ser His Lys Gly Thr Ile Lys Glu Ser Arg Val Leu
                    325                 330                 335

Ala Pro Trp Ile Thr Glu Thr His Phe Lys Glu Leu Val Pro Gly Arg
                340                 345                 350

Leu Tyr Gln Val Thr Val Ser Cys Val Ser Gly Glu Leu Ser Ala Gln
                355                 360                 365

Lys Met Ala Val Gly Arg Thr Phe Pro Leu Ala Val Leu Gln Leu Arg
370                 375                 380

Val Lys His Ala Asn Glu Thr Ser Leu Ser Ile Met Trp Gln Thr Pro
385                 390                 395                 400

Val Ala Glu Trp Glu Lys Tyr Ile Ile Ser Leu Ala Asp Arg Asp Leu
                    405                 410                 415

Leu Leu Ile His Lys Ser Leu Ser Lys Asp Ala Lys Glu Phe Thr Phe
                    420                 425                 430

Thr Asp Leu Val Pro Gly Arg Lys Tyr Met Ala Thr Val Thr Ser Ile
                435                 440                 445

Ser Gly Asp Leu Lys Asn Ser Ser Val Lys Gly Arg Thr Val Pro
                450                 455                 460

Ala Gln Val Thr Asp Leu His Val Ala Asn Gln Gly Met Thr Ser Ser
465                 470                 475                 480

Leu Phe Thr Asn Trp Thr Gln Ala Gln Gly Asp Val Glu Phe Tyr Gln
                    485                 490                 495

Val Leu Leu Ile His Glu Asn Val Ile Lys Asn Glu Ser Ile Ser
                500                 505                 510

Ser Glu Thr Ser Arg Tyr Ser Phe His Ser Leu Lys Ser Gly Ser Leu
                515                 520                 525

Tyr Ser Val Val Val Thr Thr Val Ser Gly Gly Ile Ser Ser Arg Gln
                530                 535                 540

Val Val Val Glu Gly Arg Thr Val Pro Ser Ser Val Ser Gly Val Thr
545                 550                 555                 560

Val Asn Asn Ser Gly Arg Asn Asp Tyr Leu Ser Val Ser Trp Leu Leu
                    565                 570                 575

Ala Pro Gly Asp Val Asp Asn Tyr Glu Val Thr Leu Ser His Asp Gly
                580                 585                 590
```

```
Lys Val Gln Ser Leu Val Ile Ala Lys Ser Val Arg Glu Cys Ser
            595                 600                 605
Phe Ser Ser Leu Thr Pro Gly Arg Leu Tyr Thr Val Thr Ile Thr Thr
610                 615                 620
Arg Ser Gly Lys Tyr Glu Asn His Ser Phe Ser Gln Glu Arg Thr Val
625                 630                 635                 640
Pro Asp Lys Val Gln Gly Val Ser Val Ser Asn Ser Ala Arg Ser Asp
                645                 650                 655
Tyr Leu Arg Val Ser Trp Val His Ala Thr Gly Asp Phe Asp His Tyr
            660                 665                 670
Glu Val Thr Ile Lys Asn Lys Asn Asn Phe Ile Gln Thr Lys Ser Ile
            675                 680                 685
Pro Lys Ser Glu Asn Glu Cys Val Phe Val Gln Leu Val Pro Gly Arg
            690                 695                 700
Leu Tyr Ser Val Thr Val Thr Thr Lys Ser Gly Gln Tyr Glu Ala Asn
705                 710                 715                 720
Glu Gln Gly Asn Gly Arg Thr Ile Pro Glu Lys Gly Asn Ser Ala Asp
                725                 730                 735
Ile Gln His Ser Gly Gly Arg Ser Ser Leu Glu Gly Pro Arg Phe Glu
            740                 745                 750
Gly Lys Pro Ile Pro Asn Pro Leu Leu Gly Leu Asp Ser Thr Arg Thr
            755                 760                 765
Gly His His His His His His
            770                 775

<210> SEQ ID NO 5
<211> LENGTH: 421
<212> TYPE: PRT
<213> ORGANISM: Homo sapiens

<400> SEQUENCE: 5

Met Leu Ser His Gly Ala Gly Leu Ala Leu Trp Ile Thr Leu Ser Leu
1               5                   10                  15
Leu Gln Thr Gly Leu Ala Glu Pro Glu Arg Cys Asn Phe Thr Leu Ala
            20                  25                  30
Glu Ser Lys Ala Ser Ser His Ser Val Ser Ile Gln Trp Arg Ile Leu
        35                  40                  45
Gly Ser Pro Cys Asn Phe Ser Leu Ile Tyr Ser Ser Asp Thr Leu Gly
    50                  55                  60
Ala Ala Leu Cys Pro Thr Phe Arg Ile Asp Asn Thr Thr Tyr Gly Cys
65                  70                  75                  80
Asn Leu Gln Asp Leu Gln Ala Gly Thr Ile Tyr Asn Phe Lys Ile Ile
                85                  90                  95
Ser Leu Asp Glu Glu Arg Thr Val Val Leu Gln Thr Asp Pro Leu Pro
            100                 105                 110
Pro Ala Arg Phe Gly Val Ser Lys Glu Lys Thr Thr Ser Thr Gly Leu
        115                 120                 125
His Val Trp Trp Thr Pro Ser Ser Gly Lys Val Thr Ser Tyr Glu Val
    130                 135                 140
Gln Leu Phe Asp Glu Asn Asn Gln Lys Ile Gln Gly Val Gln Ile Gln
145                 150                 155                 160
Glu Ser Thr Ser Trp Asn Glu Tyr Thr Phe Phe Asn Leu Thr Ala Gly
                165                 170                 175
Ser Lys Tyr Asn Ile Ala Ile Thr Ala Val Ser Gly Gly Lys Arg Ser
```

```
            180                 185                 190
Phe Ser Val Tyr Thr Asn Gly Ser Thr Val Pro Ser Pro Val Lys Asp
            195                 200                 205

Ile Gly Ile Ser Thr Lys Ala Asn Ser Leu Leu Ile Ser Trp Ser His
        210                 215                 220

Gly Ser Gly Asn Val Glu Arg Tyr Arg Leu Met Leu Met Asp Lys Gly
225                 230                 235                 240

Ile Leu Val His Gly Val Val Asp Lys His Ala Thr Ser Tyr Ala
                245                 250                 255

Phe His Gly Leu Thr Pro Gly Tyr Leu Tyr Asn Leu Thr Val Met Thr
            260                 265                 270

Glu Ala Ala Gly Leu Gln Asn Tyr Arg Trp Lys Leu Val Arg Thr Ala
        275                 280                 285

Pro Met Glu Val Ser Asn Leu Lys Val Thr Asn Asp Gly Ser Leu Thr
    290                 295                 300

Ser Leu Lys Val Lys Trp Gln Arg Pro Pro Gly Asn Val Asp Ser Tyr
305                 310                 315                 320

Asn Ile Thr Leu Ser His Lys Gly Thr Ile Lys Glu Ser Arg Val Leu
                325                 330                 335

Ala Pro Trp Ile Thr Glu Thr His Phe Lys Glu Leu Val Pro Gly Arg
            340                 345                 350

Leu Tyr Gln Val Thr Val Ser Cys Val Ser Gly Glu Leu Ser Ala Gln
        355                 360                 365

Lys Met Ala Val Gly Arg Thr Phe Lys Gly Asn Ser Ala Asp Ile Gln
    370                 375                 380

His Ser Gly Gly Arg Ser Ser Leu Glu Gly Pro Arg Phe Glu Gly Lys
385                 390                 395                 400

Pro Ile Pro Asn Pro Leu Leu Gly Leu Asp Ser Thr Arg Thr Gly His
                405                 410                 415

His His His His His
            420

<210> SEQ ID NO 6
<211> LENGTH: 247
<212> TYPE: PRT
<213> ORGANISM: Homo sapiens

<400> SEQUENCE: 6

Met Leu Ser His Gly Ala Gly Leu Ala Leu Trp Ile Thr Leu Ser Leu
1               5                   10                  15

Leu Gln Thr Gly Leu Ala Glu Pro Glu Arg Cys Asn Phe Thr Leu Ala
            20                  25                  30

Glu Ser Lys Ala Ser Ser His Ser Val Ser Ile Gln Trp Arg Ile Leu
        35                  40                  45

Gly Ser Pro Cys Asn Phe Ser Leu Ile Tyr Ser Ser Asp Thr Leu Gly
    50                  55                  60

Ala Ala Leu Cys Pro Thr Phe Arg Ile Asp Asn Thr Thr Tyr Gly Cys
65                  70                  75                  80

Asn Leu Gln Asp Leu Gln Ala Gly Thr Ile Tyr Asn Phe Lys Ile Ile
                85                  90                  95

Ser Leu Asp Glu Glu Arg Thr Val Val Leu Gln Thr Asp Pro Leu Pro
            100                 105                 110

Pro Ala Arg Phe Gly Val Ser Lys Glu Lys Thr Thr Ser Thr Gly Leu
        115                 120                 125
```

His Val Trp Trp Thr Pro Ser Ser Gly Lys Val Thr Ser Tyr Glu Val
        130                 135                 140

Gln Leu Phe Asp Glu Asn Asn Gln Lys Ile Gln Gly Val Gln Ile Gln
145                 150                 155                 160

Glu Ser Thr Ser Trp Asn Glu Tyr Thr Phe Phe Asn Leu Thr Ala Gly
                165                 170                 175

Ser Lys Tyr Asn Ile Ala Ile Thr Ala Val Ser Gly Gly Lys Arg Ser
                180                 185                 190

Phe Ser Val Tyr Thr Asn Gly Ser Thr Val Lys Gly Asn Ser Ala Asp
                195                 200                 205

Ile Gln His Ser Gly Gly Arg Ser Ser Leu Glu Gly Pro Arg Phe Glu
210                 215                 220

Gly Lys Pro Ile Pro Asn Pro Leu Leu Gly Leu Asp Ser Thr Arg Thr
225                 230                 235                 240

Gly His His His His His His
                245

<210> SEQ ID NO 7
<211> LENGTH: 1632
<212> TYPE: PRT
<213> ORGANISM: Mus musculus

<400> SEQUENCE: 7

Met Leu Arg His Gly Ala Leu Thr Ala Leu Trp Ile Thr Leu Ser Val
1               5                   10                  15

Val Gln Thr Gly Val Ala Glu Gln Val Lys Cys Asn Phe Thr Leu Leu
                20                  25                  30

Glu Ser Arg Val Ser Ser Leu Ser Ala Ser Ile Gln Trp Arg Thr Phe
                35                  40                  45

Ala Ser Pro Cys Asn Phe Ser Leu Ile Tyr Ser Ser Asp Thr Ser Gly
            50                  55                  60

Pro Met Trp Cys His Pro Ile Arg Ile Asp Asn Phe Thr Tyr Gly Cys
65                  70                  75                  80

Asn Pro Lys Asp Leu Gln Ala Gly Thr Val Tyr Asn Phe Arg Ile Val
                85                  90                  95

Ser Leu Asp Gly Glu Glu Ser Thr Leu Val Leu Gln Thr Asp Pro Leu
                100                 105                 110

Pro Pro Ala Arg Phe Glu Val Asn Arg Glu Lys Thr Ala Ser Thr Thr
            115                 120                 125

Leu Gln Val Arg Trp Thr Pro Ser Ser Gly Lys Val Ser Trp Tyr Glu
130                 135                 140

Val Gln Leu Phe Asp His Asn Asn Gln Lys Ile Gln Glu Val Gln Val
145                 150                 155                 160

Gln Glu Ser Thr Thr Trp Ser Gln Tyr Thr Phe Leu Asn Leu Thr Glu
                165                 170                 175

Gly Asn Ser Tyr Lys Val Ala Ile Thr Ala Val Ser Gly Glu Lys Arg
                180                 185                 190

Ser Phe Pro Val Tyr Ile Asn Gly Ser Thr Val Pro Ser Pro Val Lys
                195                 200                 205

Asp Leu Gly Ile Ser Pro Asn Pro Asn Ser Leu Leu Ile Ser Trp Ser
210                 215                 220

Arg Gly Ser Gly Asn Val Glu Gln Tyr Arg Leu Val Leu Met Asp Lys
225                 230                 235                 240

Gly Ala Ile Val Gln Asp Thr Asn Val Asp Arg Arg Asp Thr Ser Tyr
                245                 250                 255

```
Ala Phe His Glu Leu Thr Pro Gly His Leu Tyr Asn Leu Thr Ile Val
            260                 265                 270

Thr Met Ala Ser Gly Leu Gln Asn Ser Arg Trp Lys Leu Val Arg Thr
        275                 280                 285

Ala Pro Met Glu Val Ser Asn Leu Lys Val Thr Asn Asp Gly Arg Leu
    290                 295                 300

Thr Ser Leu Asn Val Lys Trp Gln Lys Pro Pro Gly Asp Val Asp Ser
305                 310                 315                 320

Tyr Ser Ile Thr Leu Ser His Gln Gly Thr Ile Lys Glu Ser Lys Thr
                325                 330                 335

Leu Ala Pro Pro Val Thr Glu Thr Gln Phe Lys Asp Leu Val Pro Gly
            340                 345                 350

Arg Leu Tyr Gln Val Thr Ile Ser Cys Ile Ser Gly Glu Leu Ser Ala
        355                 360                 365

Glu Lys Ser Ala Ala Gly Arg Thr Val Pro Glu Lys Val Arg Asn Leu
    370                 375                 380

Val Ser Tyr Asn Glu Ile Trp Met Lys Ser Phe Thr Val Asn Trp Thr
385                 390                 395                 400

Pro Pro Ala Gly Asp Trp Glu His Tyr Arg Ile Val Leu Phe Asn Glu
                405                 410                 415

Ser Leu Val Leu Leu Asn Thr Thr Val Gly Lys Glu Glu Thr His Tyr
            420                 425                 430

Ala Leu Asp Gly Leu Glu Leu Ile Pro Gly Arg Gln Tyr Glu Ile Glu
        435                 440                 445

Val Ile Val Glu Ser Gly Asn Leu Arg Asn Ser Glu Arg Cys Gln Gly
    450                 455                 460

Arg Thr Val Pro Leu Ala Val Leu Gln Leu Arg Val Lys His Ala Asn
465                 470                 475                 480

Glu Thr Ser Leu Gly Ile Thr Trp Arg Ala Pro Leu Gly Glu Trp Glu
                485                 490                 495

Lys Tyr Ile Ile Ser Leu Met Asp Arg Glu Leu Leu Val Ile His Lys
            500                 505                 510

Ser Leu Ser Lys Asp Ala Lys Glu Phe Thr Phe Thr Asp Leu Met Pro
        515                 520                 525

Gly Arg Asn Tyr Lys Ala Thr Val Thr Ser Met Ser Gly Asp Leu Lys
    530                 535                 540

Gln Ser Ser Ser Ile Lys Gly Arg Thr Val Pro Ala Gln Val Thr Asp
545                 550                 555                 560

Leu His Val Asn Asn Gln Gly Met Thr Ser Ser Leu Phe Thr Asn Trp
                565                 570                 575

Thr Lys Ala Leu Gly Asp Val Glu Phe Tyr Gln Val Leu Leu Ile His
            580                 585                 590

Glu Asn Val Val Val Lys Asn Glu Ser Val Ser Ser Asp Thr Ser Arg
        595                 600                 605

Tyr Ser Phe Arg Ala Leu Lys Pro Gly Ser Leu Tyr Ser Val Val Val
    610                 615                 620

Thr Thr Val Ser Gly Gly Ile Ser Ser Arg Gln Val Val Ala Glu Gly
625                 630                 635                 640

Arg Thr Val Pro Ser Ser Val Ser Gly Val Thr Val Asn Asn Ser Gly
                645                 650                 655

Arg Asn Asp Tyr Leu Ser Val Ser Trp Leu Pro Ala Pro Gly Glu Val
            660                 665                 670
```

-continued

```
Asp His Tyr Val Val Ser Leu Ser His Glu Gly Lys Val Asp Gln Phe
            675                 680                 685

Leu Ile Ile Ala Lys Ser Val Ser Glu Cys Ser Phe Ser Ser Leu Thr
        690                 695                 700

Pro Gly Arg Leu Tyr Asn Val Thr Val Thr Thr Lys Ser Gly Asn Tyr
705                 710                 715                 720

Ala Ser His Ser Phe Thr Glu Glu Arg Thr Val Pro Asp Lys Val Gln
                725                 730                 735

Gly Ile Ser Val Ser Asn Ser Ala Arg Ser Asp Tyr Leu Lys Val Ser
                740                 745                 750

Trp Val His Ala Thr Gly Asp Phe Asp His Tyr Glu Val Thr Ile Lys
        755                 760                 765

Asn Arg Glu Ser Phe Ile Gln Thr Lys Thr Ile Pro Lys Ser Glu Asn
770                 775                 780

Glu Cys Glu Phe Ile Glu Leu Val Pro Gly Arg Leu Tyr Ser Val Thr
785                 790                 795                 800

Val Ser Thr Lys Ser Gly Gln Tyr Glu Ala Ser Glu Gln Gly Thr Gly
                805                 810                 815

Arg Thr Ile Pro Glu Pro Val Lys Asp Leu Thr Leu Leu Asn Arg Ser
        820                 825                 830

Thr Glu Asp Leu His Val Thr Trp Ser Arg Ala Asn Gly Asp Val Asp
        835                 840                 845

Gln Tyr Glu Val Gln Leu Leu Phe Asn Asp Met Lys Val Phe Pro His
        850                 855                 860

Ile His Leu Val Asn Thr Ala Thr Glu Tyr Lys Phe Thr Ala Leu Thr
865                 870                 875                 880

Pro Gly Arg His Tyr Lys Ile Leu Val Leu Thr Ile Ser Gly Asp Val
                885                 890                 895

Gln Gln Ser Ala Phe Ile Glu Gly Leu Thr Val Pro Ser Thr Val Lys
        900                 905                 910

Asn Ile His Ile Ser Ala Asn Gly Ala Thr Asp Arg Leu Met Val Thr
        915                 920                 925

Trp Ser Pro Gly Gly Gly Asp Val Asp Ser Tyr Val Val Ser Ala Phe
        930                 935                 940

Arg Gln Asp Glu Lys Val Asp Ser Gln Thr Ile Pro Lys His Ala Ser
945                 950                 955                 960

Glu His Thr Phe His Arg Leu Glu Ala Gly Ala Lys Tyr Arg Ile Ala
                965                 970                 975

Ile Val Ser Val Ser Gly Ser Leu Arg Asn Gln Ile Asp Ala Leu Gly
        980                 985                 990

Gln Thr Val Pro Ala Ser Val Gln  Glu Val Val Ala Ala  Asn Ala Tyr
        995                 1000                1005

Ser Ser  Asn Ser Leu Thr Val  Ser Trp Gln Lys Ala  Leu Gly Val
        1010                1015                1020

Ala Glu  Arg Tyr Asp Ile Leu  Leu Leu Asn Glu Asn  Gly Leu Leu
        1025                1030                1035

Leu Ser  Asn Val Ser Glu Pro  Ala Thr Ala Arg Gln  His Lys Phe
        1040                1045                1050

Glu Asp  Leu Thr Pro Gly Lys  Lys Tyr Lys Met Gln  Ile Leu Thr
        1055                1060                1065

Val Ser  Gly Gly Leu Phe Ser  Lys Glu Ser Gln Ala  Glu Gly Arg
        1070                1075                1080

Thr Val  Pro Ala Ala Val Thr  Asn Leu Arg Ile Thr  Glu Asn Ser
```

|      |      |      |      |      | 1085 |      |      |      | 1090 |      |      |      |      | 1095 |
|------|------|------|------|------|------|------|------|------|------|------|------|------|------|------|
| Ser  | Arg  | Tyr  | Leu  | Ser  | Phe  | Gly  | Trp  | Thr  | Ala  | Ser  | Glu  | Gly  | Glu  | Leu  |
|      |      |      |      |      | 1100 |      |      |      | 1105 |      |      |      | 1110 |      |
| Ser  | Trp  | Tyr  | Asn  | Ile  | Phe  | Leu  | Tyr  | Asn  | Pro  | Asp  | Arg  | Thr  | Leu  | Gln  |
|      |      |      |      |      | 1115 |      |      |      | 1120 |      |      | 1125 |      |      |
| Glu  | Arg  | Ala  | Gln  | Val  | Asp  | Pro  | Leu  | Val  | Gln  | Ser  | Phe  | Ser  | Phe  | Gln  |
|      |      |      |      |      | 1130 |      |      |      | 1135 |      |      |      | 1140 |      |
| Asn  | Leu  | Leu  | Gln  | Gly  | Arg  | Met  | Tyr  | Lys  | Met  | Val  | Ile  | Val  | Thr  | His  |
|      |      |      |      |      | 1145 |      |      |      | 1150 |      |      | 1155 |      |      |
| Ser  | Gly  | Glu  | Leu  | Ser  | Asn  | Glu  | Ser  | Phe  | Ile  | Phe  | Gly  | Arg  | Thr  | Val  |
|      |      |      |      |      | 1160 |      |      |      | 1165 |      |      | 1170 |      |      |
| Pro  | Ala  | Ala  | Val  | Asn  | His  | Leu  | Lys  | Gly  | Ser  | His  | Arg  | Asn  | Thr  | Thr  |
|      |      |      |      |      | 1175 |      |      |      | 1180 |      |      | 1185 |      |      |
| Asp  | Ser  | Leu  | Trp  | Phe  | Ser  | Trp  | Ser  | Pro  | Ala  | Ser  | Gly  | Asp  | Phe  | Asp  |
|      |      |      |      |      | 1190 |      |      |      | 1195 |      |      | 1200 |      |      |
| Phe  | Tyr  | Glu  | Leu  | Ile  | Leu  | Tyr  | Asn  | Pro  | Asn  | Gly  | Thr  | Lys  | Lys  | Glu  |
|      |      |      |      |      | 1205 |      |      |      | 1210 |      |      | 1215 |      |      |
| Asn  | Trp  | Lys  | Glu  | Lys  | Asp  | Val  | Thr  | Glu  | Trp  | Arg  | Phe  | Gln  | Gly  | Leu  |
|      |      |      |      |      | 1220 |      |      |      | 1225 |      |      | 1230 |      |      |
| Val  | Pro  | Gly  | Arg  | Lys  | Tyr  | Thr  | Leu  | Tyr  | Val  | Val  | Thr  | His  | Ser  | Gly  |
|      |      |      |      |      | 1235 |      |      |      | 1240 |      |      | 1245 |      |      |
| Asp  | Leu  | Ser  | Asn  | Lys  | Val  | Thr  | Gly  | Glu  | Gly  | Arg  | Thr  | Ala  | Pro  | Ser  |
|      |      |      |      |      | 1250 |      |      |      | 1255 |      |      | 1260 |      |      |
| Pro  | Pro  | Ser  | Leu  | Leu  | Ser  | Phe  | Ala  | Asp  | Val  | Ala  | Asn  | Thr  | Ser  | Leu  |
|      |      |      |      |      | 1265 |      |      |      | 1270 |      |      | 1275 |      |      |
| Ala  | Ile  | Thr  | Trp  | Lys  | Gly  | Pro  | Pro  | Asp  | Trp  | Thr  | Asp  | Tyr  | Asn  | Asp  |
|      |      |      |      |      | 1280 |      |      |      | 1285 |      |      | 1290 |      |      |
| Phe  | Glu  | Leu  | Gln  | Trp  | Phe  | Pro  | Gly  | Asp  | Ala  | Leu  | Thr  | Ile  | Phe  | Asn  |
|      |      |      |      |      | 1295 |      |      |      | 1300 |      |      | 1305 |      |      |
| Pro  | Tyr  | Ser  | Ser  | Arg  | Lys  | Ser  | Glu  | Gly  | Arg  | Ile  | Val  | Tyr  | Gly  | Leu  |
|      |      |      |      |      | 1310 |      |      |      | 1315 |      |      | 1320 |      |      |
| His  | Pro  | Gly  | Arg  | Ser  | Tyr  | Gln  | Phe  | Ser  | Val  | Lys  | Thr  | Val  | Ser  | Gly  |
|      |      |      |      |      | 1325 |      |      |      | 1330 |      |      | 1335 |      |      |
| Asp  | Ser  | Trp  | Lys  | Thr  | Tyr  | Ser  | Lys  | Pro  | Ile  | Ser  | Gly  | Ser  | Val  | Arg  |
|      |      |      |      |      | 1340 |      |      |      | 1345 |      |      | 1350 |      |      |
| Thr  | Lys  | Pro  | Asp  | Lys  | Ile  | Gln  | Asn  | Leu  | His  | Cys  | Arg  | Pro  | Gln  | Asn  |
|      |      |      |      |      | 1355 |      |      |      | 1360 |      |      | 1365 |      |      |
| Ser  | Thr  | Ala  | Ile  | Ala  | Cys  | Ser  | Trp  | Ile  | Pro  | Pro  | Asp  | Ser  | Asp  | Phe  |
|      |      |      |      |      | 1370 |      |      |      | 1375 |      |      | 1380 |      |      |
| Asp  | Gly  | Tyr  | Ser  | Ile  | Glu  | Cys  | Arg  | Lys  | Met  | Asp  | Thr  | Gln  | Glu  | Ile  |
|      |      |      |      |      | 1385 |      |      |      | 1390 |      |      | 1395 |      |      |
| Glu  | Phe  | Ser  | Arg  | Lys  | Leu  | Glu  | Lys  | Glu  | Lys  | Ser  | Leu  | Leu  | Asn  | Ile  |
|      |      |      |      |      | 1400 |      |      |      | 1405 |      |      | 1410 |      |      |
| Met  | Met  | Leu  | Val  | Pro  | His  | Lys  | Arg  | Tyr  | Leu  | Val  | Ser  | Ile  | Lys  | Val  |
|      |      |      |      |      | 1415 |      |      |      | 1420 |      |      | 1425 |      |      |
| Gln  | Ser  | Ala  | Gly  | Met  | Thr  | Ser  | Glu  | Val  | Val  | Glu  | Asp  | Ser  | Thr  | Ile  |
|      |      |      |      |      | 1430 |      |      |      | 1435 |      |      | 1440 |      |      |
| Thr  | Met  | Ile  | Asp  | Arg  | Pro  | Pro  | Gln  | Pro  | Pro  | Pro  | His  | Ile  | Arg  | Val  |
|      |      |      |      |      | 1445 |      |      |      | 1450 |      |      | 1455 |      |      |
| Asn  | Glu  | Lys  | Asp  | Val  | Leu  | Ile  | Ser  | Lys  | Ser  | Ser  | Ile  | Asn  | Phe  | Thr  |
|      |      |      |      |      | 1460 |      |      |      | 1465 |      |      | 1470 |      |      |
| Val  | Asn  | Cys  | Ser  | Trp  | Phe  | Ser  | Asp  | Thr  | Asn  | Gly  | Ala  | Val  | Lys  | Tyr  |
|      |      |      |      |      | 1475 |      |      |      | 1480 |      |      | 1485 |      |      |

-continued

```
Phe Ala Val Val Arg Glu Ala Asp Ser Met Asp Glu Leu Lys
    1490            1495                1500

Pro Glu Gln Gln His Pro Leu Pro Ser Tyr Leu Glu Tyr Arg His
    1505            1510                1515

Asn Ala Ser Ile Arg Val Tyr Gln Thr Asn Tyr Phe Ala Ser Lys
    1520            1525                1530

Cys Ala Glu Ser Pro Asp Ser Ser Lys Ser Phe Asn Ile Lys
    1535            1540                1545

Leu Gly Ala Glu Met Asp Ser Leu Gly Gly Lys Cys Asp Pro Ser
    1550            1555                1560

Gln Gln Lys Phe Cys Asp Gly Pro Leu Lys Pro His Thr Ala Tyr
    1565            1570                1575

Arg Ile Ser Ile Arg Ala Phe Thr Gln Leu Phe Asp Glu Asp Leu
    1580            1585                1590

Lys Glu Phe Thr Lys Pro Leu Tyr Ser Asp Thr Phe Phe Ser Met
    1595            1600                1605

Pro Ile Thr Thr Glu Ser Glu Pro Leu Phe Gly Val Ile Glu Arg
    1610            1615                1620

Gly Arg His His His His His His Gly
    1625            1630
```

<210> SEQ ID NO 8
<211> LENGTH: 774
<212> TYPE: PRT
<213> ORGANISM: Artificial Sequence
<220> FEATURE:
<223> OTHER INFORMATION: human-mouse chimeric molecule

<400> SEQUENCE: 8

```
Met Leu Arg His Gly Ala Leu Thr Ala Leu Trp Ile Thr Leu Ser Val
1               5                   10                  15

Val Gln Thr Gly Val Ala Glu Pro Glu Arg Cys Asn Phe Thr Leu Ala
                20                  25                  30

Glu Ser Lys Ala Ser Ser His Ser Val Ser Ile Gln Trp Arg Ile Leu
            35                  40                  45

Gly Ser Pro Cys Asn Phe Ser Leu Ile Tyr Ser Ser Asp Thr Leu Gly
        50                  55                  60

Ala Ala Leu Cys Pro Thr Phe Arg Ile Asp Asn Thr Thr Tyr Gly Cys
65                  70                  75                  80

Asn Leu Gln Asp Leu Gln Ala Gly Thr Ile Tyr Asn Phe Lys Ile Ile
                85                  90                  95

Ser Leu Asp Glu Glu Arg Thr Val Val Leu Gln Thr Asp Pro Leu Pro
            100                 105                 110

Pro Ala Arg Phe Glu Val Asn Arg Glu Lys Thr Ala Ser Thr Thr Leu
        115                 120                 125

Gln Val Arg Trp Thr Pro Ser Ser Gly Lys Val Ser Trp Tyr Glu Val
    130                 135                 140

Gln Leu Phe Asp His Asn Asn Gln Lys Ile Gln Glu Val Gln Val Gln
145                 150                 155                 160

Glu Ser Thr Thr Trp Ser Gln Tyr Thr Phe Leu Asn Leu Thr Glu Gly
                165                 170                 175

Asn Ser Tyr Lys Val Ala Ile Thr Ala Val Ser Gly Glu Lys Arg Ser
            180                 185                 190

Phe Pro Val Tyr Ile Asn Gly Ser Thr Val Pro Ser Pro Val Lys Asp
        195                 200                 205
```

```
Leu Gly Ile Ser Pro Asn Pro Asn Ser Leu Leu Ile Ser Trp Ser Arg
    210             215                 220

Gly Ser Gly Asn Val Glu Gln Tyr Arg Leu Val Leu Met Asp Lys Gly
225             230                 235                 240

Ala Ile Val Gln Asp Thr Asn Val Asp Arg Arg Asp Thr Ser Tyr Ala
                245                 250                 255

Phe His Glu Leu Thr Pro Gly His Leu Tyr Asn Leu Thr Ile Val Thr
            260                 265                 270

Met Ala Ser Gly Leu Gln Asn Ser Arg Trp Lys Leu Val Arg Thr Ala
        275                 280                 285

Pro Met Glu Val Ser Asn Leu Lys Val Thr Asn Asp Gly Arg Leu Thr
290                 295                 300

Ser Leu Asn Val Lys Trp Gln Lys Pro Pro Gly Asp Val Asp Ser Tyr
305                 310                 315                 320

Ser Ile Thr Leu Ser His Gln Gly Thr Ile Lys Glu Ser Lys Thr Leu
                325                 330                 335

Ala Pro Pro Val Thr Glu Thr Gln Phe Lys Asp Leu Val Pro Gly Arg
                340                 345                 350

Leu Tyr Gln Val Thr Ile Ser Cys Ile Ser Gly Glu Leu Ser Ala Glu
        355                 360                 365

Lys Ser Ala Ala Gly Arg Thr Val Pro Glu Lys Val Arg Asn Leu Val
370                 375                 380

Ser Tyr Asn Glu Ile Trp Met Lys Ser Phe Thr Val Asn Trp Thr Pro
385                 390                 395                 400

Pro Ala Gly Asp Trp Glu His Tyr Arg Ile Val Leu Phe Asn Glu Ser
                405                 410                 415

Leu Val Leu Leu Asn Thr Thr Val Gly Lys Glu Glu Thr His Tyr Ala
                420                 425                 430

Leu Asp Gly Leu Glu Leu Ile Pro Gly Arg Gln Tyr Glu Ile Glu Val
        435                 440                 445

Ile Val Glu Ser Gly Asn Leu Arg Asn Ser Glu Arg Cys Gln Gly Arg
450                 455                 460

Thr Val Pro Leu Ala Val Leu Gln Leu Arg Val Lys His Ala Asn Glu
465                 470                 475                 480

Thr Ser Leu Gly Ile Thr Trp Arg Ala Pro Leu Gly Glu Trp Glu Lys
                485                 490                 495

Tyr Ile Ile Ser Leu Met Asp Arg Glu Leu Leu Val Ile His Lys Ser
                500                 505                 510

Leu Ser Lys Asp Ala Lys Glu Phe Thr Phe Thr Asp Leu Met Pro Gly
        515                 520                 525

Arg Asn Tyr Lys Ala Thr Val Thr Ser Met Ser Gly Asp Leu Lys Gln
530                 535                 540

Ser Ser Ser Ile Lys Gly Arg Thr Val Pro Ala Gln Val Thr Asp Leu
545                 550                 555                 560

His Val Asn Asn Gln Gly Met Thr Ser Ser Leu Phe Thr Asn Trp Thr
                565                 570                 575

Lys Ala Leu Gly Asp Val Glu Phe Tyr Gln Val Leu Leu Ile His Glu
                580                 585                 590

Asn Val Val Lys Asn Glu Ser Val Ser Ser Asp Thr Ser Arg Tyr
        595                 600                 605

Ser Phe Arg Ala Leu Lys Pro Gly Ser Leu Tyr Ser Val Val Val Thr
610                 615                 620
```

Thr Val Ser Gly Gly Ile Ser Ser Arg Gln Val Ala Glu Gly Arg
625                 630                 635                 640

Thr Val Pro Ser Ser Val Ser Gly Val Thr Val Asn Asn Ser Gly Arg
                645                 650                 655

Asn Asp Tyr Leu Ser Val Ser Trp Leu Pro Ala Pro Gly Glu Val Asp
            660                 665                 670

His Tyr Val Val Ser Leu Ser His Glu Gly Lys Val Asp Gln Phe Leu
        675                 680                 685

Ile Ile Ala Lys Ser Val Ser Glu Cys Ser Phe Ser Ser Leu Thr Pro
    690                 695                 700

Gly Arg Leu Tyr Asn Val Thr Val Thr Thr Lys Ser Gly Asn Tyr Ala
705                 710                 715                 720

Ser His Ser Phe Thr Glu Glu Arg Thr Lys Gly Asn Ser Ala Asp Ile
                725                 730                 735

Gln His Ser Gly Gly Arg Ser Ser Leu Glu Gly Pro Arg Phe Glu Gly
            740                 745                 750

Lys Pro Ile Pro Asn Pro Leu Leu Gly Leu Asp Ser Arg Thr Gly
        755                 760                 765

His His His His His His
    770

<210> SEQ ID NO 9
<211> LENGTH: 775
<212> TYPE: PRT
<213> ORGANISM: Artificial Sequence
<220> FEATURE:
<223> OTHER INFORMATION: human-mouse chimeric molecule

<400> SEQUENCE: 9

Met Leu Arg His Gly Ala Leu Thr Ala Leu Trp Ile Thr Leu Ser Val
1               5                   10                  15

Val Gln Thr Gly Val Ala Glu Gln Val Lys Cys Asn Phe Thr Leu Leu
            20                  25                  30

Glu Ser Arg Val Ser Ser Leu Ser Ala Ser Ile Gln Trp Arg Thr Phe
        35                  40                  45

Ala Ser Pro Cys Asn Phe Ser Leu Ile Tyr Ser Ser Asp Thr Ser Gly
    50                  55                  60

Pro Met Trp Cys His Pro Ile Arg Ile Asp Asn Phe Thr Tyr Gly Cys
65              70                  75                  80

Asn Pro Lys Asp Leu Gln Ala Gly Thr Val Tyr Asn Phe Arg Ile Val
            85                  90                  95

Ser Leu Asp Gly Glu Glu Ser Thr Leu Val Leu Gln Thr Asp Pro Leu
        100                 105                 110

Pro Pro Ala Arg Phe Gly Val Ser Lys Glu Lys Thr Thr Ser Thr Gly
    115                 120                 125

Leu His Val Trp Trp Thr Pro Ser Ser Gly Lys Val Thr Ser Tyr Glu
130                 135                 140

Val Gln Leu Phe Asp Glu Asn Asn Gln Lys Ile Gln Gly Val Gln Ile
145                 150                 155                 160

Gln Glu Ser Thr Ser Trp Asn Glu Tyr Thr Phe Phe Asn Leu Thr Ala
                165                 170                 175

Gly Ser Lys Tyr Asn Ile Ala Ile Thr Ala Val Ser Gly Gly Lys Arg
            180                 185                 190

Ser Phe Ser Val Tyr Thr Asn Gly Ser Thr Val Pro Ser Pro Val Lys
        195                 200                 205

```
Asp Leu Gly Ile Ser Pro Asn Pro Asn Ser Leu Leu Ile Ser Trp Ser
    210                 215                 220

Arg Gly Ser Gly Asn Val Glu Gln Tyr Arg Leu Val Leu Met Asp Lys
225                 230                 235                 240

Gly Ala Ile Val Gln Asp Thr Asn Val Asp Arg Arg Asp Thr Ser Tyr
                245                 250                 255

Ala Phe His Glu Leu Thr Pro Gly His Leu Tyr Asn Leu Thr Ile Val
            260                 265                 270

Thr Met Ala Ser Gly Leu Gln Asn Ser Arg Trp Lys Leu Val Arg Thr
        275                 280                 285

Ala Pro Met Glu Val Ser Asn Leu Lys Val Thr Asn Asp Gly Arg Leu
    290                 295                 300

Thr Ser Leu Asn Val Lys Trp Gln Lys Pro Pro Gly Asp Val Asp Ser
305                 310                 315                 320

Tyr Ser Ile Thr Leu Ser His Gln Gly Thr Ile Lys Glu Ser Lys Thr
                325                 330                 335

Leu Ala Pro Pro Val Thr Glu Thr Gln Phe Lys Asp Leu Val Pro Gly
            340                 345                 350

Arg Leu Tyr Gln Val Thr Ile Ser Cys Ile Ser Gly Glu Leu Ser Ala
        355                 360                 365

Glu Lys Ser Ala Ala Gly Arg Thr Val Pro Glu Lys Val Arg Asn Leu
    370                 375                 380

Val Ser Tyr Asn Glu Ile Trp Met Lys Ser Phe Thr Val Asn Trp Thr
385                 390                 395                 400

Pro Pro Ala Gly Asp Trp Glu His Tyr Arg Ile Val Leu Phe Asn Glu
                405                 410                 415

Ser Leu Val Leu Leu Asn Thr Thr Val Gly Lys Glu Glu Thr His Tyr
            420                 425                 430

Ala Leu Asp Gly Leu Glu Leu Ile Pro Gly Arg Gln Tyr Glu Ile Glu
        435                 440                 445

Val Ile Val Glu Ser Gly Asn Leu Arg Asn Ser Glu Arg Cys Gln Gly
    450                 455                 460

Arg Thr Val Pro Leu Ala Val Leu Gln Leu Arg Val Lys His Ala Asn
465                 470                 475                 480

Glu Thr Ser Leu Gly Ile Thr Trp Arg Ala Pro Leu Gly Glu Trp Glu
                485                 490                 495

Lys Tyr Ile Ile Ser Leu Met Asp Arg Glu Leu Leu Val Ile His Lys
            500                 505                 510

Ser Leu Ser Lys Asp Ala Lys Glu Phe Thr Phe Thr Asp Leu Met Pro
        515                 520                 525

Gly Arg Asn Tyr Lys Ala Thr Val Thr Ser Met Ser Gly Asp Leu Lys
    530                 535                 540

Gln Ser Ser Ser Ile Lys Gly Arg Thr Val Pro Ala Gln Val Thr Asp
545                 550                 555                 560

Leu His Val Asn Asn Gln Gly Met Thr Ser Ser Leu Phe Thr Asn Trp
                565                 570                 575

Thr Lys Ala Leu Gly Asp Val Glu Phe Tyr Gln Val Leu Leu Ile His
            580                 585                 590

Glu Asn Val Val Lys Asn Glu Ser Val Ser Ser Asp Thr Ser Arg
        595                 600                 605

Tyr Ser Phe Arg Ala Leu Lys Pro Gly Ser Leu Tyr Ser Val Val Val
    610                 615                 620

Thr Thr Val Ser Gly Gly Ile Ser Ser Arg Gln Val Val Ala Glu Gly
```

```
                625                 630                 635                 640
Arg Thr Val Pro Ser Ser Val Gly Val Thr Val Asn Asn Ser Gly
                    645                 650                 655

Arg Asn Asp Tyr Leu Ser Val Ser Trp Leu Pro Ala Pro Gly Glu Val
                660                 665                 670

Asp His Tyr Val Val Ser Leu Ser His Glu Gly Lys Val Asp Gln Phe
                675                 680                 685

Leu Ile Ile Ala Lys Ser Val Ser Glu Cys Ser Phe Ser Ser Leu Thr
            690                 695                 700

Pro Gly Arg Leu Tyr Asn Val Thr Val Thr Thr Lys Ser Gly Asn Tyr
705                 710                 715                 720

Ala Ser His Ser Phe Thr Glu Glu Arg Thr Lys Gly Asn Ser Ala Asp
                    725                 730                 735

Ile Gln His Ser Gly Gly Arg Ser Ser Leu Glu Gly Pro Arg Phe Glu
                740                 745                 750

Gly Lys Pro Ile Pro Asn Pro Leu Leu Gly Leu Asp Ser Thr Arg Thr
                755                 760                 765

Gly His His His His His His
                770                 775

<210> SEQ ID NO 10
<211> LENGTH: 774
<212> TYPE: PRT
<213> ORGANISM: Artificial Sequence
<220> FEATURE:
<223> OTHER INFORMATION: human-mouse chimeric molecule

<400> SEQUENCE: 10

Met Leu Arg His Gly Ala Leu Thr Ala Leu Trp Ile Thr Leu Ser Val
1               5                   10                  15

Val Gln Thr Gly Val Ala Glu Pro Glu Arg Cys Asn Phe Thr Leu Ala
                20                  25                  30

Glu Ser Lys Ala Ser Ser His Ser Val Ser Ile Gln Trp Arg Ile Leu
            35                  40                  45

Gly Ser Pro Cys Asn Phe Ser Leu Ile Tyr Ser Ser Asp Thr Leu Gly
        50                  55                  60

Ala Ala Leu Cys Pro Thr Phe Arg Ile Asp Asn Thr Thr Tyr Gly Cys
65                  70                  75                  80

Asn Leu Gln Asp Leu Gln Ala Gly Thr Ile Tyr Asn Phe Lys Ile Ile
                85                  90                  95

Ser Leu Asp Glu Glu Arg Thr Val Val Leu Gln Thr Asp Pro Leu Pro
                100                 105                 110

Pro Ala Arg Phe Gly Val Ser Lys Glu Lys Thr Thr Ser Thr Gly Leu
            115                 120                 125

His Val Trp Trp Thr Pro Ser Ser Gly Lys Val Thr Ser Tyr Glu Val
        130                 135                 140

Gln Leu Phe Asp Glu Asn Asn Gln Lys Ile Gln Gly Val Gln Ile Gln
145                 150                 155                 160

Glu Ser Thr Ser Trp Asn Glu Tyr Thr Phe Phe Asn Leu Thr Ala Gly
                165                 170                 175

Ser Lys Tyr Asn Ile Ala Ile Thr Ala Val Ser Gly Gly Lys Arg Ser
                180                 185                 190

Phe Ser Val Tyr Thr Asn Gly Ser Thr Val Pro Ser Pro Val Lys Asp
            195                 200                 205

Leu Gly Ile Ser Pro Asn Pro Asn Ser Leu Leu Ile Ser Trp Ser Arg
```

-continued

```
            210                 215                 220
Gly Ser Gly Asn Val Glu Gln Tyr Arg Leu Val Leu Met Asp Lys Gly
225                 230                 235                 240

Ala Ile Val Gln Asp Thr Asn Val Asp Arg Arg Asp Thr Ser Tyr Ala
                245                 250                 255

Phe His Glu Leu Thr Pro Gly His Leu Tyr Asn Leu Thr Ile Val Thr
                260                 265                 270

Met Ala Ser Gly Leu Gln Asn Ser Arg Trp Lys Leu Val Arg Thr Ala
                275                 280                 285

Pro Met Glu Val Ser Asn Leu Lys Val Thr Asn Asp Gly Arg Leu Thr
290                 295                 300

Ser Leu Asn Val Lys Trp Gln Lys Pro Pro Gly Asp Val Asp Ser Tyr
305                 310                 315                 320

Ser Ile Thr Leu Ser His Gln Gly Thr Ile Lys Glu Ser Lys Thr Leu
                325                 330                 335

Ala Pro Pro Val Thr Glu Thr Gln Phe Lys Asp Leu Val Pro Gly Arg
                340                 345                 350

Leu Tyr Gln Val Thr Ile Ser Cys Ile Ser Gly Glu Leu Ser Ala Glu
                355                 360                 365

Lys Ser Ala Ala Gly Arg Thr Val Pro Glu Lys Val Arg Asn Leu Val
370                 375                 380

Ser Tyr Asn Glu Ile Trp Met Lys Ser Phe Thr Val Asn Trp Thr Pro
385                 390                 395                 400

Pro Ala Gly Asp Trp Glu His Tyr Arg Ile Val Leu Phe Asn Glu Ser
                405                 410                 415

Leu Val Leu Leu Asn Thr Thr Val Gly Lys Glu Glu Thr His Tyr Ala
                420                 425                 430

Leu Asp Gly Leu Glu Leu Ile Pro Gly Arg Gln Tyr Glu Ile Glu Val
                435                 440                 445

Ile Val Glu Ser Gly Asn Leu Arg Asn Ser Glu Arg Cys Gln Gly Arg
450                 455                 460

Thr Val Pro Leu Ala Val Leu Gln Leu Arg Val Lys His Ala Asn Glu
465                 470                 475                 480

Thr Ser Leu Gly Ile Thr Trp Arg Ala Pro Leu Gly Glu Trp Glu Lys
                485                 490                 495

Tyr Ile Ile Ser Leu Met Asp Arg Glu Leu Leu Val Ile His Lys Ser
                500                 505                 510

Leu Ser Lys Asp Ala Lys Glu Phe Thr Phe Thr Asp Leu Met Pro Gly
                515                 520                 525

Arg Asn Tyr Lys Ala Thr Val Thr Ser Met Ser Gly Asp Leu Lys Gln
530                 535                 540

Ser Ser Ser Ile Lys Gly Arg Thr Val Pro Ala Gln Val Thr Asp Leu
545                 550                 555                 560

His Val Asn Asn Gln Gly Met Thr Ser Ser Leu Phe Thr Asn Trp Thr
                565                 570                 575

Lys Ala Leu Gly Asp Val Glu Phe Tyr Gln Val Leu Leu Ile His Glu
                580                 585                 590

Asn Val Val Val Lys Asn Glu Ser Val Ser Ser Asp Thr Ser Arg Tyr
                595                 600                 605

Ser Phe Arg Ala Leu Lys Pro Gly Ser Leu Tyr Ser Val Val Val Thr
                610                 615                 620

Thr Val Ser Gly Gly Ile Ser Ser Arg Gln Val Val Ala Glu Gly Arg
625                 630                 635                 640
```

```
Thr Val Pro Ser Ser Val Ser Gly Val Thr Val Asn Asn Ser Gly Arg
            645                 650                 655

Asn Asp Tyr Leu Ser Val Ser Trp Leu Pro Ala Pro Gly Glu Val Asp
            660                 665                 670

His Tyr Val Val Ser Leu Ser His Glu Gly Lys Val Asp Gln Phe Leu
            675                 680                 685

Ile Ile Ala Lys Ser Val Ser Glu Cys Ser Phe Ser Ser Leu Thr Pro
            690                 695                 700

Gly Arg Leu Tyr Asn Val Thr Val Thr Thr Lys Ser Gly Asn Tyr Ala
705                 710                 715                 720

Ser His Ser Phe Thr Glu Glu Arg Thr Lys Gly Asn Ser Ala Asp Ile
                725                 730                 735

Gln His Ser Gly Gly Arg Ser Ser Leu Glu Gly Pro Arg Phe Glu Gly
                740                 745                 750

Lys Pro Ile Pro Asn Pro Leu Leu Gly Leu Asp Ser Thr Arg Thr Gly
                755                 760                 765

His His His His His His
            770

<210> SEQ ID NO 11
<211> LENGTH: 89
<212> TYPE: PRT
<213> ORGANISM: Homo sapiens

<400> SEQUENCE: 11

Leu Ala Glu Pro Glu Arg Cys Asn Phe Thr Leu Ala Glu Ser Lys Ala
1               5                   10                  15

Ser Ser His Ser Val Ser Ile Gln Trp Arg Ile Leu Gly Ser Pro Cys
                20                  25                  30

Asn Phe Ser Leu Ile Tyr Ser Ser Asp Thr Leu Gly Ala Ala Leu Cys
            35                  40                  45

Pro Thr Phe Arg Ile Asp Asn Thr Thr Tyr Gly Cys Asn Leu Gln Asp
        50                  55                  60

Leu Gln Ala Gly Thr Ile Tyr Asn Phe Lys Ile Ile Ser Leu Asp Glu
65                  70                  75                  80

Glu Arg Thr Val Val Leu Gln Thr Asp
                85
```

ANTIBODIES THAT BIND HUMAN PROTEIN TYROSINE PHOSPHATASE BETA (HPTPBETA) AND USES THEREOF

CROSS REFERENCE TO RELATED APPLICATIONS

This application is a Continuation Application of Ser. No. 16/696,212 filed Nov. 26, 2019, which is a Continuation Application of U.S. application Ser. No. 15/894,442, filed Feb. 12, 2018, which is a Continuation Application of U.S. application Ser. No. 15/430,100, filed Feb. 10, 2017, now U.S. Pat. No. 9,926,367, issued Mar. 27, 2018, which is a Continuation Application of U.S. application Ser. No. 13/958,990, filed Aug. 5, 2013, which is a Divisional Application of U.S. application Ser. No. 13/115,180, filed May 25, 2011, now U.S. Pat. No. 8,524,235, issued Sep. 3, 2013, which is a Divisional Application of U.S. application Ser. No. 11/784,094, filed Apr. 5, 2007, now U.S. Pat. No. 7,973,142, issued Jul. 5, 2011, which claims the benefit of U.S. Provisional Application No. 60/790,506, filed Apr. 7, 2006, and U.S. Provisional Application No. 60/798,896, filed May 9, 2006 the content of each of which is herein incorporated by reference in its entirety.

SEQUENCE LISTING

The instant application contains a Sequence Listing which has been submitted electronically in ASCII format and is hereby incorporated by reference in its entirety. Said ASCII copy, created on Feb. 6, 2020, is named 45725704304SL.txt and is 98,773 bytes in size.

FIELD OF INVENTION

This invention relates to antibodies and antigen binding fragments thereof that bind to human protein tyrosine phosphatase beta (HPTPbeta) and uses thereof.

BACKGROUND OF THE INVENTION

Angiogenesis, the sprouting of new blood vessels from the pre-existing vasculature, plays an important role in a wide range of physiological and pathological processes (Nguyen, L. L. et al, Int. Rev. Cytol., 204, 1-48, (2001)). Angiogenesis is a complex process, mediated by communication between the endothelial cells that line blood vessels and their surrounding environment. In the early stages of angiogenesis, tissue or tumor cells produce and secrete pro-angiogenic growth factors in response to environmental stimuli such as hypoxia. These factors diffuse to nearby endothelial cells and stimulate receptors that lead to the production and secretion of proteases that degrade the surrounding extracellular matrix. The activated endothelial cells begin to migrate and proliferate into the surrounding tissue toward the source of these growth factors (Bussolino, F., Trends Biochem. Sci., 22, 251-256, (1997)). Endothelial cells then stop proliferating and differentiate into tubular structures, which is the first step in the formation of stable, mature blood vessels. Subsequently, periendothelial cells, such as pericytes and smooth muscle cells, are recruited to the newly formed vessel in a further step toward vessel maturation.

Angiogenesis is regulated by a balance of naturally occurring pro- and anti-angiogenic factors. Vascular endothelial growth factor, fibroblast growth factor, and angiopoietin represent a few of the many potential pro-angiogenic growth factors. These ligands bind to their respective receptor tyrosine kinases on the endothelial cell surface and transduce signals that promote cell migration and proliferation. Whereas many regulatory factors have been identified, the molecular mechanisms that drive this process are still not fully understood.

There are many disease states driven by persistent unregulated or improperly regulated angiogenesis. In such disease states, unregulated or improperly regulated angiogenesis may either cause a particular disease or exacerbate an existing pathological condition. For example, ocular neovascularization has been implicated as the most common cause of blindness and underlies the pathology of approximately 20 eye diseases. In certain previously existing conditions, such as arthritis, newly formed capillary blood vessels invade the joints and destroy cartilage. In diabetes, new capillaries formed in the retina invade the vitreous humor, causing bleeding and blindness.

Both the growth and metastasis of solid tumors may also be angiogenesis-dependent, Folkman et al., "Tumor Angiogenesis," Chapter 10, 206-32, in The Molecular Basis of Cancer, Mendelsohn et al., eds., W. B. Saunders, (1995). It has been shown that tumors which enlarge to greater than 2 mm in diameter must obtain their own blood supply and do so by inducing the growth of new capillary blood vessels. After these new blood vessels become embedded in the tumor, they provide nutrients and growth factors essential for tumor growth as well as a means for tumor cells to enter the circulation and metastasize to distant sites, such as liver, lung or bone (Weidner, New Eng. J. Med., 324, 1, 1-8 (1991)). When used as drugs in tumor-bearing animals, natural inhibitors of angiogenesis may prevent the growth of small tumors (O'Reilly et al., Cell, 79, 315-28 (1994)). In some protocols, the application of such inhibitors leads to tumor regression and dormancy even after cessation of treatment (O'Reilly et al., Cell, 88, 277-85 (1997)). Moreover, supplying inhibitors of angiogenesis to certain tumors may potentiate their response to other therapeutic regimens (see, e.g., Teischer et al., Int. J. Cancer, 57, 920-25 (1994)).

Although many disease states are driven by persistent unregulated or improperly regulated angiogenesis, some disease states may be treated by enhancing angiogenesis. Tissue growth and repair are biologic events wherein cellular proliferation and angiogenesis occur. Thus an important aspect of wound repair is the revascularization of damaged tissue by angiogenesis.

Chronic, non-healing wounds are a major cause of prolonged morbidity in the aged human population. This is especially the case in bedridden or diabetic patients who develop severe, non-healing skin ulcers. In many of these cases, the delay in healing is a result of inadequate blood supply either as a result of continuous pressure or of vascular blockage. Poor capillary circulation due to small artery atherosclerosis or venous stasis contributes to the failure to repair damaged tissue. Such tissues are often infected with microorganisms that proliferate unchallenged by the innate defense systems of the body which require well vascularized tissue to effectively eliminate pathogenic organisms. As a result, most therapeutic intervention centers on restoring blood flow to ischemic tissues thereby allowing nutrients and immunological factors access to the site of the wound.

Atherosclerotic lesions in large vessels may cause tissue ischemia that could be ameliorated by modulating blood vessel growth to the affected tissue. For example, atherosclerotic lesions in the coronary arteries may cause angina and myocardial infarction that could be prevented if one could restore blood flow by stimulating the growth of collateral arteries. Similarly, atherosclerotic lesions in the large arteries that supply the legs may cause ischemia in the skeletal muscle that limits mobility and in some cases necessitates amputation, which may also be prevented by improving blood flow with angiogenic therapy.

Other diseases such as diabetes and hypertension are characterized by a decrease in the number and density of small blood vessels such as arterioles and capillaries. These small blood vessels are important for the delivery of oxygen and nutrients. A decrease in the number and density of these vessels contributes to the adverse consequences of hypertension and diabetes including claudication, ischemic ulcers, accelerated hypertension, and renal failure. These common disorders and many other less common ailments, such as Burgers disease, could be ameliorated by increasing the number and density of small blood vessels using angiogenic therapy.

Thus, there is a continuing need to identify regulators of angiogenesis.

In view of the foregoing, there is a need to identify biochemical targets in the treatment of angiogenesis mediated disorders. However, angiogenesis involves the action of multiple growth factors and their cognate receptor tyrosine kinases (RTKs), Yancopoulos et al., Nature, 407, 242-248, 2000). Vascular endothelial growth factor (VEGF), for example, is important for the differentiation of endothelial cells into nascent blood vessels in the embryonic vasculature. Further, VEGF enhances blood vessel development in the adult vasculature. Administration of exogenous VEGF enhances the development of the collateral vasculature and improves blood flow to ischemic tissues.

To date, three VEGF RTKs have been identified, VEGFR1 (FLT-1), VEGFR2 (KDR), and VEGFR3 (FLT-4). Although these receptors are highly conserved, based on biochemical characterization and biological activity, each has specific and non-overlapping functions. Of the three receptors, VEGFR2 is believed to play the predominant role in mediating VEGF actions in the developing vasculature and during angiogenesis in adults. However, both VEGFR1 and VEGFR3 are required for normal development of the embryonic vasculature and may also be important for angiogenesis in adult tissues. Upon VEGF binding and dimerization, a conformational change in the VEGFR2 kinase domain enhances its kinase activity resulting in "autophosphorylation" of the other member of the pair on specific tyrosine residues. These autophosphorylation events serve to further enhance the kinase activity and provide anchor points for the association of intracellular signaling molecules.

However, activation of a single angiogenic pathway may not be sufficient to produce persistent and functional vessels that provide adequate perfusion to ischemic tissue. These findings, together with fact that multiple RTKs are involved in the assembly of embryonic vasculature, indicate that biochemical targets that modulate multiple angiogenic pathways will have advantages over administration of a single growth factor.

Protein tyrosine phosphatases (PTPs) comprise a large family of closely related enzymes that dephosphorylate proteins that contain phosphotyrosine residues. Recent evidence suggests that one function of PTPs is to limit the phosphorylation and activation of RTKs. For example, HCPTPA, a low molecular weight protein tyrosine phosphatase, was shown to associate with VEGFR2 and negatively regulate its activation in cultured endothelial cells and its biological activity in angiogenesis assays, (Huang et al., Journal of Biological Chemistry, 274, 38183-38185, 1999).

In addition to VEGFR2, signaling input from another RTK, Tie-2, the receptor for the angiopoietins (Ang1 and Ang2), is also important. Deletion of either the Ang1 or Tie-2 gene in mice may result in embryonic lethality secondary to abnormalities in the developing vasculature (Yancopoulos et al., Nature, 407, 242-248, 2000). In addition, overexpression of Ang1 in the skin increases skin vascularity and administration of exogenous Ang1 increases blood flow to ischemic skeletal muscle (Suri et al., Science, 282, 468-471, 1998). Moreover, inhibiting the activation of Tie-2 inhibits angiogenesis and limits tumor progression in animal models of cancer, (Lin et al., J Clin. Invest., 100, 2072-2078, 1997). In addition to its angiogenic activities, activation of Tie-2 by exogenous administration of Ang1 blocks VEGF mediated vascular leak and pro-inflammatory effects, but enhances its angiogenic effects (Thurston et al., Nature Medicine, 6, 460-463, 2000). Therefore, biological targets that modulate both VEGFR2 and Tie-2 signaling may yield superior proangiogenic or antiangiogenic therapies.

HPTPbeta (first described in Kruegar et al., EMBO J., 9, (1990)) has been suggested for modulating the activity of angiopoietin receptor-type tyrosine kinase Tie-2, e.g., WO 00/65088). HPTPbeta is also suggested for regulating activities of VEGFR2, e.g., US Pat. Pub. No. 2004/0077065.

It would be desirable to develop antibodies, e.g., a humanized monoclonal antibody, which selectively regulate the activity of HPTPbeta and thereby enhance angiogenic signaling, stimulate blood vessel growth (angiogenesis), and/or increase blood flow in ischemic tissue, or reduce angiogenic signaling, reduce blood vessel growth, and/or decrease blood flow to the effected tissue. Herein are described antibodies and fragments thereof that bind HPTPbeta and regulate angiogenic cell signaling, which in turn, regulates angiogenesis.

SUMMARY OF THE INVENTION

The present invention relates to antibodies that bind human protein tyrosine phosphatase beta HPTPbeta and thereby regulate angiogenic cell signaling, which in turn, regulates angiogenesis.

In one embodiment, the invention relates to an isolated antibody or antigen-binding fragment thereof which binds to human protein tyrosine phosphatase beta, wherein said antibody or antigen-binding fragment thereof regulates angiogenic cell signaling, which in turn, regulates angiogenesis.

In another embodiment, the invention relates to an antibody that binds the N-terminal portion of human protein tyrosine phosphatase beta.

In another embodiment, the invention relates to an antibody that binds the first FN3 repeat of human protein tyrosine phosphatase beta.

In another embodiment, the invention relates to an antibody that binds the first FN3 repeat of human protein tyrosine phosphatase beta, wherein the first FN3 repeat of human protein tyrosine phosphatase beta has the sequence as shown in SEQ ID NO: 11, or a portion thereof.

In another embodiment, the invention relates to an antibody wherein the antibody is a monoclonal antibody.

In another embodiment, the invention relates to an antibody wherein the antibody is the monoclonal antibody R15E6 (Mouse hybridoma, Balbc spleen cells (B cells) deposited with American Type Culture Collection (ATCC), P.O. Box 1549, Manassas, Va. 20108 USA on 4 May 2006, assigned ATCC No. PTA-7580).

In another embodiment, the invention relates to an antibody having the same, or substantially the same, biological characteristics of R15E6.

In another embodiment, the invention relates to an antibody, wherein the antibody or the antigen binding fragment is humanized.

In another embodiment, the invention relates to an antibody, wherein the antibody comprises antigen binding region residues from the monoclonal antibody R15E6 and is humanized.

In another embodiment, the invention relates to an antigen binding fragment of an antibody, wherein the fragment comprises heavy and light chain variable regions.

In another embodiment, the invention relates to an antigen binding fragment of an antibody, wherein the antigen-binding fragment is selected from the group consisting of an Fv fragment, an Fab fragment, an Fab' fragment, and an F(ab')$_2$ fragment.

In another embodiment, the invention relates to an a method of treating an angiogenesis regulated disorder in a subject, comprising: identifying a subject in need of regulation of angiogenesis; and administering to the subject an effective amount of an antibody or antigen-binding fragment thereof which binds HPTPbeta and regulates angiogenesis.

In another embodiment, the invention relates to a method of treating an angiogenesis regulated disorder in a subject, wherein the angiogenesis regulated disorder is an angiogenesis elevated disorder, and is selected from the group consisting of diabetic retinopathy, macular degeneration, cancer, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, Eales' disease, Behcet's disease, infections causing a retinitis or choroiditis, presumed ocular histoplasmosis, Best's disease, myopia, optic pits, Stargardt's disease, pars planitis, chronic retinal detachment, hyperviscosity syndrome, toxoplasmosis, trauma and post-laser complications, diseases associated with rubeosis, and proliferative vitreoretinopathy.

In another embodiment, the invention relates to a method of treating an angiogenesis regulated disorder in a subject, wherein the angiogenesis regulated disorder is an angiogenesis elevated disorder, and is selected from the group including but not limited to diabetic retinopathy, macular degeneration, cancer, rheumatoid arthritis, hemangiomas, Osler-Weber-Rendu disease, or hereditary hemorrhagic telangiectasia, and solid or blood borne tumors In another embodiment, the invention relates to a method of treating an angiogenesis regulated disorder in a subject, wherein the angiogenesis regulated disorder is an angiogenesis elevated disorder, and is selected from the group consisting of inflammatory bowel diseases such as Crohn's disease and ulcerative colitis, psoriasis, sarcoidosis, rheumatoid arthritis, hemangiomas, Osler-Weber-Rendu disease, or hereditary hemorrhagic telangiectasia, solid or blood borne tumors and acquired immune deficiency syndrome.

In another embodiment, the invention relates to a method of treating an angiogenesis regulated disorder in a subject, wherein the angiogenesis regulated disorder is an angiogenesis reduced disorder and is selected from the group including but not limited to skeletal muscle or myocardial ischemia, stroke, coronary artery disease, peripheral vascular disease, coronary artery disease, cerebrovascular disease, diabetic neuropathy and wound healing.

In another embodiment, the invention relates to a method of treating an angiogenesis regulated disorder in a subject, wherein the angiogenesis regulated disorder is an angiogenesis reduced disorder and is selected from the group consisting of skeletal muscle and myocardial ischemia, stroke, coronary artery disease, peripheral vascular disease, coronary artery disease.

In another embodiment, the invention relates to a method of treating an angiogenesis reduced disorder in a subject, wherein the angiogenesis reduced disorder is peripheral vascular disease.

In another embodiment, the invention relates to a method of treating an angiogenesis reduced disorder in a subject, wherein the angiogenesis reduced disorder is coronary artery disease.

In another embodiment, the invention relates to a pharmaceutical composition, comprising: an antibody or a fragment thereof which binds to human protein tyrosine phosphatase beta; and a pharmaceutically acceptable carrier.

In another embodiment, the invention relates to a pharmaceutical composition, comprising: an antibody or a fragment thereof which binds to human protein tyrosine phosphatase beta, wherein the antibody is the monoclonal antibody R15E6; and a pharmaceutically acceptable carrier.

In another embodiment, the invention relates to a pharmaceutical composition, comprising: an antibody or a fragment thereof which binds to human protein tyrosine phosphatase beta, wherein the antibody is a monoclonal antibody having the same, or substantially the same, biological characteristics of R15E6; and a pharmaceutically acceptable carrier.

In another embodiment, the invention relates to a pharmaceutical composition, comprising: an antibody or a fragment thereof which binds to human protein tyrosine phosphatase beta, wherein the antibody or the antigen binding fragment is humanized; and a pharmaceutically acceptable carrier.

In another embodiment, the invention relates to a pharmaceutical composition, comprising: an antibody or a fragment thereof which binds to human protein tyrosine phosphatase beta, wherein the antibody comprises antigen binding region residues from the monoclonal antibody R15E6 and is humanized; and a pharmaceutically acceptable carrier.

SEQUENCE LISTING DESCRIPTION

Figure 1:
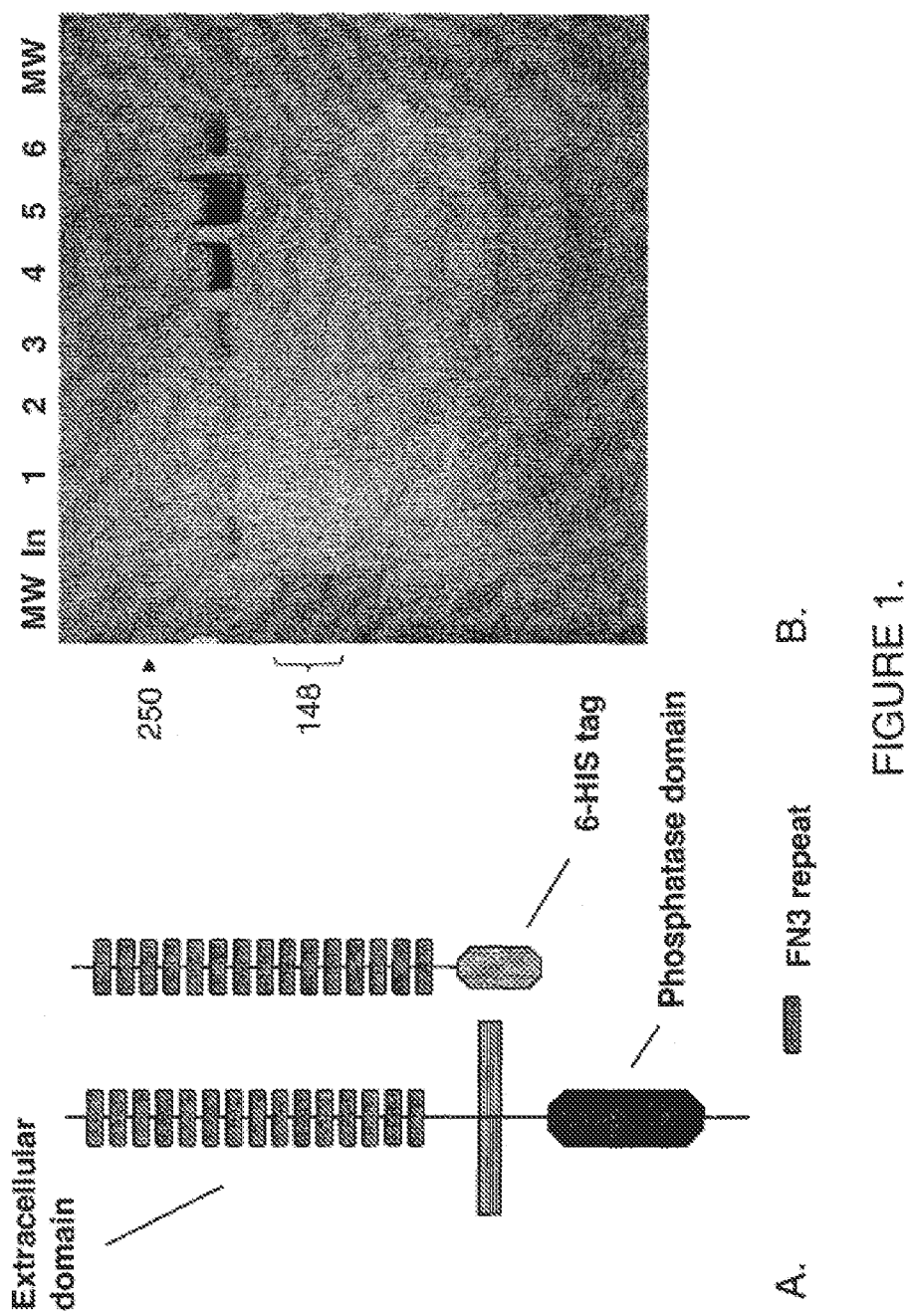
FIG. 1. Design and production of the HPTPβ ECD protein. (Panel A) Schematic representation of the full-length HPTPβ and the HPTPβ extracellular domain-6His fusion protein. (Panel B) Silver stain of Imidazole eluates from a Ni-NTA column loaded with supernatant from HEK293 cells transfected with a vector directing the expression of βECD-6His. A single high molecular weight band consistent with the HPTPβ extracellular domain-6His protein is detected.

Each of the nucleotide and protein sequences in the sequence listing, along with the corresponding Genbank or Derwent accession number(s), where applicable, and species from which it is derived, is shown in Table I.

TABLE I

| Sequence Description | SEQ ID NOs: Nucleotide, Protein | Species | Equivalent Genbank Acc. No. |
|---|---|---|---|
| Extracellular domain of HPTPbeta with His and Gly tag | 1, 2 | Homo Sapiens | |
| Extracellular domain of full-length HPTPbeta | 3 | Homo Sapiens | X54131 NM_002837 |
| ½ (AA1-730, 8 FN3's)775 aa | 4 | Homo Sapiens | |
| ¼ (AA1-376, 4 FN3's)421 aa | 5 | Homo Sapiens | |
| ⅛ (AA1-202, 2 FN3's)247 aa | 6 | Homo Sapiens | |
| Mouse full length ECD1632 aa | 7 | Mus musculus | NM_029928 |
| First human FN3-Mouse ½ | 8 | Human-mouse chimera | |
| Second human FN3-Mouse ½ | 9 | Human-mouse chimera | |
| First two human FN3,-Mouse ½ | 10 | Human-mouse chimera | |
| Human FN3, first repeat | 11 | Homo sapines | |

DETAILED DESCRIPTION OF THE INVENTION

The present invention relates to antibodies that bind HPTPbeta and uses thereof.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The techniques and procedures are generally performed according to conventional methods known in the art and as described in various general and more specific references that are cited and discussed throughout the present specification. Unless specific definitions are provided, the nomenclature utilized in connection with, and the laboratory procedures and techniques of, analytical chemistry, synthetic organic chemistry, and medicinal and pharmaceutical chemistry described herein are those known and commonly used in the art.

Standard techniques may be used for chemical syntheses, chemical analyses, pharmaceutical preparation, formulation, and delivery, and treatment of patients.

The following terms, unless otherwise indicated, shall be understood to have the following meanings:

"Protein," is used herein interchangeably with peptide and polypeptide. HPTPbeta is human protein tyrosine phosphatase as defined in the sequence listing. In some of the embodiments, various fragments of HPTPbeta are used. Homologs, orthologs, fragments, variants, and mutants of HPTPbeta protein and gene, as described below, are considered as within the scope of the term "HPTPbeta".

By "fragment" is intended a portion of the nucleotide or protein sequence. Fragments may retain the biological activity of the native protein. Fragments of a nucleotide sequence are also useful as hybridization probes and primers or to regulate expression of a gene, e.g., antisense, siRNA, or micro RNA. A biologically active portion may be prepared by isolating a portion of one of the nucleotide sequences of the invention, expressing the encoded portion (e.g., by recombinant expression in vitro), and assessing the activity of the encoded protein.

One of skill in the art would also recognize that genes and proteins from species other than those listed in the sequence listing, particularly vertebrate species, may be useful. Such species include, but are not limited to, mice, rats, guinea pigs, rabbits, dogs, pigs, goats, cows, monkeys, chimpanzees, sheep, hamsters, and zebrafish. One of skill in the art would further recognize that by using probes from the known species' sequences, cDNA or genomic sequences homologous to the known sequence could be obtained from the same or alternate species by known cloning methods. Such homologs and orthologs are contemplated to be useful in practicing the invention.

By "variants" are intended similar sequences. For example, conservative variants may include those sequences that, because of the degeneracy of the genetic code, encode the amino acid sequence of one of the polypeptides of the invention. Naturally occurring allelic variants, and splice variants may be identified with the use of known techniques, e.g., with polymerase chain reaction (PCR), single nucleotide polymorphism (SNP) analysis, and hybridization techniques. To isolate orthologs and homologs, generally stringent hybridization conditions are utilized, dictated by specific sequences, sequence length, guanine+cytosine (GC) content, and other parameters. Variant nucleotide sequences also include synthetically derived nucleotide sequences, e.g., derived by using site-directed mutagenesis. Variants may contain additional sequences from the genomic locus alone or in combination with other sequences.

The molecules of the invention also include truncated and/or mutated proteins wherein regions of the protein not required for ligand binding or signaling have been deleted or modified. Similarly, they may be mutated to modify their ligand binding or signaling activities. Such mutations may involve non-conservative mutations, deletions, or additions of amino acids or protein domains. Variant proteins may or may not retain biological activity. Such variants may result from, e.g., genetic polymorphism or from human manipulation.

Fusions proteins are also contemplated herein. Using known methods, one of skill in the art would be able to make fusion proteins of the proteins of the invention; that, while different from native form, may be useful. For example, the fusion partner may be a signal (or leader) polypeptide sequence that co-translationally or post-translationally directs transfer of the protein from its site of synthesis to another site (e.g., the yeast α-factor leader). Alternatively, it may be added to facilitate purification or identification of the protein of the invention (e.g., poly-His, Flag peptide, or fluorescent proteins).

The term "antigen" refers to a molecule or a portion of a molecule capable of being bound by a selective binding agent, such as an antibody, and additionally is capable of being used in an animal to produce antibodies capable of binding to an epitope of that antigen. An antigen may have one or more epitopes.

The term "epitope" includes any antigenic determinant, preferably a polypeptide determinant, capable of specific binding to an immunoglobulin or a T-cell receptor. In certain embodiments, epitope determinants include chemically active surface groupings such as amino acids, sugars, lipids, phosphoryl, or sulfonyl, and, in certain embodiments, may have specific three dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules. An antibody is also said to specifically bind an antigen when it exhibits higher affinity to the antigen than other related and/or unrelated molecules.

The term "antibody" (Ab) as used herein includes monoclonal antibodies, polyclonal antibodies, multi-specific antibodies (e.g. bispecific antibodies), single chain antibodies, e.g., antibodies from llama and camel, antibody fragments, e.g., variable regions and/or constant region fragments, so long as they exhibit a desired biological activity, e.g., antigen-binding activity. The term "immunoglobulin" (Ig) is used interchangeably with "antibody" herein.

An "isolated antibody" is one which has been identified, and/or separated, and/or recovered from its natural environment.

The basic four-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies may polymerize to form polyvalent assemblages comprising 2-5 of the basic 4-chain units along with J chain). In the case of IgGs, the four-chain unit is generally about 150 kilo Daltons (kDa). Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, 1994, page 71 and Chapter 6.

The L chain from any vertebrate species may be assigned to one of two clearly distinct types, called kappa and lambda, based on the amino acid sequences of their constant domains. Depending on the amino acid sequence of the constant domain of their heavy chains ($C_H$), immunoglobulins may be assigned to different classes or isotypes. There are five classes of immunoglobulins: IgA, IgD, IgE, IgG, and IgM, having heavy chains designated α, δ, ε, γ and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

Members of the Camelidae family, e.g., llama, camel, and dromedaries, contain a unique type of antibody, that are devoid of light chains, and further lack the $C_{H1}$ domain (Muyldermans, S., Rev. Mol. Biotechnol., 74, 277-302 (2001)). The variable region of these heavy chain antibodies are termed $V_{HH}$ or VHH, and constitute the smallest available intact antigen binding fragment (15 kDa) derived from a functional immunoglobulin.

The term "variable" refers to the fact that certain segments of the variable domains differ extensively in sequence among antibodies. The V domain mediates antigen binding and defines specificity of a particular antibody for its antigen. However, the variability is not evenly distributed across the 110-amino acid span of the variable domains. Instead, the V regions consist of relatively invariant stretches called framework regions (FR) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies. The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. around about residues 24-34 (L1), 50-56 (L2) and 89-97 (L3) in the $V_L$, and around about 1-35 (H1), 50-65 (H2) and 95-102 (H3) in the $V_H$; Kabat et al., *Sequences of Proteins of Immunological Interest,* 5th Ed. Public Health Service, National Institutes of Health, Bethesda, Md. (1991)) and/or those residues from a "hypervariable loop".

The term "monoclonal antibody" as used herein refers to an antibody obtained from a population of substantially homogeneous antibodies, i.e., the individual antibodies comprising the population are identical except for possible naturally occurring mutations that may be present in minor amounts. In contrast to polyclonal antibody preparations which include different antibodies directed against different epitopes, each monoclonal antibody is directed against a single epitope, i.e., a single antigenic determinant. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology or may be made using recombinant DNA methods in bacterial, eukaryotic animal or plant cells (see, e.g., U.S. Pat. No. 4,816,567). The "monoclonal antibodies" may also be isolated from phage antibody libraries, using the available techniques, e.g., Clackson et al., *Nature,* 352:624-628 (1991).

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., *Proc. Natl. Acad. Sci. USA,* 81, 6851-6855 (1984)).

An "antibody fragment" comprises a portion of a multimeric antibody, preferably the antigen binding or variable region of the intact antibody. Examples of antibody fragments include Fab, Fab', F(ab')$_2$, dimmers and trimers of Fab conjugates, Fv, scFv, minibodies; dia-, tria-, and tetrabodies; linear antibodies (See Hudson et al, Nature Med. 9, 129-134 (2003)).

"Fv" is the minimum antibody fragment which contains a complete antigen binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, and are therefore included in the definition of Fv.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding.

The terms "dia-, tria-, and tetrabodies" refer to small antibody fragments prepared by constructing sFv fragments with short linkers (about 5-10 residues) between the $V_H$ and $V_L$ domains such that inter-chain but not intra-chain pairing of the V domains is achieved, resulting in a multivalent fragment.

The term "humanized antibody" or "human antibody" refers to antibodies which comprise heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences. Means for making chimeric, CDR-grafted and humanized antibodies are known to those of ordinary skill in the art (see, e.g., U.S. Pat. Nos. 4,816,567 and 5,225,539). One method for making human antibodies employs the use of transgenic animals, such as a transgenic mouse. These transgenic animals contain a substantial portion of the human antibody producing genome inserted into their own genome and the animal's own endogenous antibody production is rendered deficient in the production of antibodies. Methods for making such transgenic animals are known in the art. Such transgenic animals may be made using XenoMouse® technology or by using a "minilocus" approach. Methods for making XenoMice® are described in U.S. Pat. Nos. 6,162,963, 6,150,584, 6,114,598 and 6,075,181. Methods for making transgenic animals using the "minilocus" approach are described in U.S. Pat. Nos. 5,545,807, 5,545,806 and 5,625,825, and WO 93/12227.

Humanization of a non-human antibody has become routine in recent years, and is now within the knowledge of one skilled in the art. Several companies provide services to make a humanized antibody, e.g., Xoma, *Aries,* Medarex, PDL, and Cambridge Antibody Technologies. Humanization protocols are extensively described in technical literature, e.g., Kipriyanov and Le Gall, Molecular Biotechnol, Vol. 26, pp 39-60 (2004), Humana Press, Totowa, N.J.; Lo, Methods Mol. Biol., Vol. 248, pp 135-159 (2004), Humana Press, Totowa, N.J.; Wu et al, J. Mol. Biol. 294, 151-162 (1999).

In certain embodiments, antibodies of the present invention may be expressed in cell lines other than hybridoma cell lines. Sequences encoding particular antibodies may be used for transformation of a suitable mammalian host cell by known methods for introducing polynucleotides into a host cell, including, for example packaging the polynucleotide in a virus (or into a viral vector) and transducing a host cell with the virus (or vector), or by transfection procedures known in the art, as exemplified by U.S. Pat. Nos. 4,399,216, 4,912,040, 4,740,461, and 4,959,455. The transformation procedure used may depend upon the host to be transformed. Methods for introduction of heterologous polynucleotides into mammalian cells are known in the art and include; but are not limited to, dextran-mediated transfection, calcium phosphate precipitation, polybrene mediated transfection, protoplast fusion, electroporation, encapsulation of the polynucleotide(s) in liposomes, mixing nucleic acid with positively-charged lipids, and direct microinjection of the DNA into nuclei.

A nucleic acid molecule encoding the amino acid sequence of a heavy chain constant region, a heavy chain variable region, a light chain constant region, or a light chain variable region of an antibody, or a fragment thereof in a suitable combination if desired, is/are inserted into an appropriate expression vector using standard ligation techniques. The antibody heavy chain or light chain constant region may be appended to the C terminus of the appropriate variable region and is ligated into an expression vector. The vector is typically selected to be functional in the particular host cell employed (i.e., the vector is compatible with the host cell machinery such that amplification of the gene and/or expression of the gene may occur). For a review of expression vectors, see Methods Enzymol. vol. 185 (Goeddel, ed.), 1990, Academic Press.

Antibodies and fragments thereof of the present invention bind HPTPbeta and regulate angiogenesis. As defined above, the term antibody is used as to denote an antigen binding fragment. The uses of such antibodies and antigen binding fragments are further described below.

Screening Assays Using In Vitro and In Vivo Models of Angiogenesis

Antibodies of the invention may be screened in angiogenesis assays that are known in the art. Such assays include in vitro assays that measure surrogates of blood vessel growth in cultured cells or formation of vascular structures from tissue explants and in vivo assays that measure blood vessel growth directly or indirectly (Auerbach, R., et al. (2003). Clin Chem 49, 32-40, Vailhe, B., et al. (2001). Lab Invest 81, 439-452).

In Vitro Models of Angiogenesis

Most of these assays employ cultured endothelial cells or tissue explants and measure the effect of agents on "angiogenic" cell responses or on the formation of blood capillary-like structures. Examples of in vitro angiogenesis assays include but are not limited to endothelial cell migration and proliferation, capillary tube formation, endothelial sprouting, the aortic ring explant assay and the chick aortic arch assay.

In Vivo Models of Angiogenesis

In these assays agents or antibodies are administered locally or systemically in the presence or absence of growth factors (i.e. VEGF or angiopoietin 1) and new blood vessel growth is measured by direct observation or by measuring a surrogate marker such as hemoglobin content or a fluorescent indicator. Examples of angiogenesis include but are not limited to chick chorioallantoic membrane assay, the corneal angiogenesis assay, and the MATRIGEL™ plug assay.

Treatment of Angiogenesis Regulated Disorders

The term "regulate" is defined as in its accepted dictionary meanings. Thus, the meaning of the term "regulate" includes, but is not limited to, up-regulate or down-regulate, to fix, to bring order or uniformity, to govern, or to direct by various means. In one aspect, an antibody may be used in a method for the treatment of an "angiogenesis elevated disorder" or "angiogenesis reduced disorder". As used herein, an "angiogenesis elevated disorder" is one that involves unwanted or elevated angiogenesis in the biological manifestation of the disease, disorder, and/or condition; in the biological cascade leading to the disorder; or as a symptom of the disorder. Similarly, the "angiogenesis reduced disorder" is one that involves wanted or reduced angiogenesis in the biological manifestations. This "involvement" of angiogenesis in an angiogenesis elevated/reduced disorder includes, but is not limited to, the following:

(1) The angiogenesis as a "cause" of the disorder or biological manifestation, whether the level of angiogenesis is elevated or reduced genetically, by infection, by autoimmunity, trauma, biomechanical causes, lifestyle, or by some other causes.

(2) The angiogenesis as part of the observable manifestation of the disease or disorder. That is, the disease or disorder is measurable in terms of the increased or reduced angiogenesis. From a clinical standpoint, angiogenesis indicates the disease; however, angiogenesis need not be the "hallmark" of the disease or disorder.

(3) The angiogenesis is part of the biochemical or cellular cascade that results in the disease or disorder. In this respect, regulation of angiogenesis may interrupt the cascade, and may control the disease. Non-limiting examples of angiogenesis regulated disorders that may be treated by the present invention are herein described below.

Antibodies of the present invention may be used to treat diseases associated with retinal/choroidal neovascularization that include, but are not limited to, diabetic retinopathy, macular degeneration, cancer, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, Eales' disease, Behcet's disease, infections causing a retinitis or choroiditis, presumed ocular histoplasmosis, Best's disease, myopia, optic pits, Stargardt's disease, pars planitis, chronic retinal detachment, hyperviscosity syndromes, toxoplasmosis, trauma and post-laser complications. Other diseases include, but are not limited to, diseases associated with rubeosis (neovascularisation of the iris) and diseases caused by the abnormal proliferation of fibrovascular or fibrous tissue including all forms of proliferative vitreoretinopathy, whether or not associated with diabetes.

Antibodies of the present invention may be used to treat diseases associated with chronic inflammation. Diseases with symptoms of chronic inflammation include inflammatory bowel diseases such as Crohn's disease and ulcerative colitis, psoriasis, sarcoidosis and rheumatoid arthritis. Angiogenesis is a key element that these chronic inflammatory diseases have in common. The chronic inflammation depends on continuous formation of capillary sprouts to maintain an influx of inflammatory cells. The influx and presence of the inflammatory cells produce granulomas and thus, maintain the chronic inflammatory state. Inhibition of angiogenesis by the compositions and methods of the present invention would prevent the formation of the granulomas and alleviate the disease.

Crohn's disease and ulcerative colitis are characterized by chronic inflammation and angiogenesis at various sites in the gastrointestinal tract. Crohn's disease is characterized by chronic granulomatous inflammation throughout the gastrointestinal tract consisting of new capillary sprouts surrounded by a cylinder of inflammatory cells. Prevention of angiogenesis inhibits the formation of the sprouts and prevents the formation of granulomas. Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhea.

The inflammatory bowel diseases also show extraintestinal manifestations such as skin lesions. Such lesions are characterized by inflammation and angiogenesis and may occur at many sites other than the gastrointestinal tract. Antibodies of the present invention may be capable of treating these lesions by preventing the angiogenesis, thus reducing the influx of inflammatory cells and the lesion formation.

Sarcoidosis is another chronic inflammatory disease that is characterized as a multisystem granulomatous disorder. The granulomas of this disease may form anywhere in the body and thus the symptoms depend on the site of the granulomas and whether the disease active. The granulomas are created by the angiogenic capillary sprouts providing a constant supply of inflammatory cells.

Antibodies of the present invention may also treat the chronic inflammatory conditions associated with psoriasis. Psoriasis, a skin disease, is another chronic and recurrent disease that is characterized by papules and plaques of various sizes. Prevention of the formation of the new blood vessels necessary to maintain the characteristic lesions leads to relief from the symptoms.

Rheumatoid arthritis is a chronic inflammatory disease characterized by nonspecific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Other diseases that may be treated according to the present invention are hemangiomas, Osler-Weber-Rendu disease, or hereditary hemorrhagic telangiectasia, solid or blood borne tumors and acquired immune deficiency syndrome.

Antibodies of the present invention may also be used to treat an "angiogenesis reduced disorder". As used herein, an "angiogenesis reduced disorder" is one that angiogenesis would be considered beneficial to treat a disease, disorder, and/or condition. The disorder is one characterized by tissue that is suffering from or at risk of suffering from ischemic damage, infection, and/or poor healing, which results when the tissue is deprived of an adequate supply of oxygenated blood due to inadequate circulation. As used herein, "tissue" is used in the broadest sense, to include, but not limited to, the following: cardiac tissue, such as myocardium and cardiac ventricles; erectile tissue; skeletal muscle; neurological tissue, such as from the cerebellum; internal organs, such as the brain, heart, pancreas, liver, spleen, and lung; or generalized area of the body such as entire limbs, a foot, or distal appendages such as fingers or toes.

Methods of Vascularizing Ischemic Tissue

In one aspect, antibodies may be used in a method of vascularizing ischemic tissue. As used herein, "ischemic tissue," means tissue that is deprived of adequate blood flow. Examples of ischemic tissue include, but are not limited to, tissue that lack adequate blood supply resulting from myocardial and cerebral infarctions, mesenteric or limb ischemia, or the result of a vascular occlusion or stenosis. In one example, the interruption of the supply of oxygenated blood may be caused by a vascular occlusion. Such vascular occlusion may be caused by arteriosclerosis, trauma, surgical procedures, disease, and/or other etiologies. Standard routine techniques are available to determine if a tissue is at risk of suffering ischemic damage from undesirable vascular occlusion. For example, in myocardial disease these methods include a variety of imaging techniques (e.g., radiotracer methodologies, x-ray, and MRI) and physiological tests. Therefore, induction of angiogenesis is an effective means of preventing or attenuating ischemia in tissues affected by or at risk of being affected by a vascular occlusion. Further, the treatment of skeletal muscle and myocardial ischemia, stroke, coronary artery disease, peripheral vascular disease, coronary artery disease is fully contemplated.

A person skilled in the art of using standard techniques may measure the vascularization of tissue. Non-limiting examples of measuring vascularization in a subject include SPECT (single photon emission computed tomography); PET (positron emission tomography); MRI (magnetic resonance imaging); and combination thereof, by measuring blood flow to tissue before and after treatment. Angiography may be used as an assessment of macroscopic vascularity. Histologic evaluation may be used to quantify vascularity at the small vessel level. These and other techniques are discussed in Simons, et al., "Clinical trials in coronary angiogenesis," Circulation, 102, 73-86 (2000).

Methods of Repairing Tissue

In one aspect, antibodies may be used in a method of repairing tissue. As used herein, "repairing tissue" means promoting tissue repair, regeneration, growth, and/or maintenance including, but not limited to, wound repair or tissue engineering. One skilled in the art appreciates that new blood vessel formation is required for tissue repair. In turn, tissue may be damaged by, including, but not limited to, traumatic injuries or conditions including arthritis, osteoporosis and other skeletal disorders, and burns. Tissue may also be damaged by injuries due to surgical procedures, irradiation, laceration, toxic chemicals, viral infection or bacterial infections, or burns. Tissue in need of repair also includes non-healing wounds. Examples of non-healing wounds include non-healing skin ulcers resulting from diabetic pathology; or fractures that do not heal readily.

Antibodies may also be used in tissue repair in the context of guided tissue regeneration (GTR) procedures. Such procedures are currently used by those skilled in the arts to accelerate wound healing following invasive surgical procedures.

Antibodies may be used in a method of promoting tissue repair characterized by enhanced tissue growth during the process of tissue engineering. As used herein, "tissue engineering" is defined as the creation, design, and fabrication of biological prosthetic devices, in combination with synthetic or natural materials, for the augmentation or replacement of body tissues and organs. Thus, the present methods may be used to augment the design and growth of human tissues outside the body for later implantation in the repair or replacement of diseased tissues. For example, antibodies may be useful in promoting the growth of skin graft replacements that are used as a therapy in the treatment of burns.

In another aspect of tissue engineering, antibodies of the present invention may be included in cell-containing or cell-free devices that induce the regeneration of functional human tissues when implanted at a site that requires regeneration. As previously discussed, biomaterial-guided tissue regeneration may be used to promote bone regrowth in, for example, periodontal disease. Thus, antibodies may be used to promote the growth of reconstituted tissues assembled into three-dimensional configurations at the site of a wound or other tissue in need of such repair.

In another aspect of tissue engineering, antibodies may be included in external or internal devices containing human tissues designed to replace the function of diseased internal tissues. This approach involves isolating cells from the body, placing them with structural matrices, and implanting the new system inside the body or using the system outside the body. For example, antibodies may be included in a cell-lined vascular graft to promote the growth of the cells contained in the graft. It is envisioned that the methods of the invention may be used to augment tissue repair, regeneration and engineering in products such as cartilage and bone, central nervous system tissues, muscle, liver, and pancreatic islet (insulin-producing) cells.

Pharmaceutical Formulations and Methods for Use

The antibodies of the invention may be administered to individuals to treat or to prevent diseases or disorders that are regulated by genes and proteins of the invention. The term "treatment" is used herein to mean that administration of a compound of the present invention mitigates a disease or a disorder in a host. Thus, the term "treatment" includes, preventing a disorder from occurring in a host, particularly when the host is predisposed to acquiring the disease, but has not yet been diagnosed with the disease; inhibiting the disorder; and/or alleviating or reversing the disorder. Insofar as the methods of the present invention are directed to preventing disorders, it is understood that the term "prevent" does not require that the disease state be completely thwarted. (See Webster's Ninth Collegiate Dictionary.) Rather, as used herein, the term preventing refers to the ability of the skilled artisan to identify a population that is susceptible to disorders, such that administration of the compounds of the present invention may occur prior to onset of a disease. The term does not imply that the disease state be completely avoided. The compounds identified by the screening methods of the present invention may be administered in conjunction with other compounds.

Safety and therapeutic efficacy of compounds identified may be determined by standard procedures using in vitro or in vivo technologies. Compounds that exhibit large therapeutic indices may be preferred, although compounds with lower therapeutic indices may be useful if the level of side effects is acceptable. The data obtained from the in vitro and in vivo toxicological and pharmacological techniques may be used to formulate the range of doses.

Effectiveness of a compound may further be assessed either in animal models or in clinical trials of patients with unregulated or improperly regulated angiogenesis.

As used herein, "pharmaceutically acceptable carrier" is intended to include all solvents, dispersion media, coatings, antibacterial and antifungal agents, isotonic and absorption delaying agents, and the like, compatible with pharmaceutical administration. The use of such media and agents for pharmaceutically active substances is known in the art. Except insofar as any conventional media or agent is incompatible with the active compound, such media may be used in the compositions of the invention. Supplementary active compounds may also be incorporated into the compositions. A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application may include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH may be adjusted with acids or bases, such as hydrochloric acid or sodium hydroxide. The parenteral preparation may be enclosed in ampoules, disposable syringes or multiple dose vials made of glass or plastic.

Pharmaceutical compositions suitable for injectable use include sterile aqueous solutions (where water-soluble), or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier may be a solvent or dispersion medium containing, for example, water, ethanol, polyol (for example, glycerol, propylene glycol, and liquid polyethylene glycol, and the like), and suitable mixtures thereof. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions may be brought about by including in the composition an agent that delays absorption, for example, aluminum monostearate and gelatin.

Sterile injectable solutions may be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Systemic administration may also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration may be accomplished using nasal sprays or suppositories. For transdermal administration, the active compounds are formulated into ointments, salves, gels, or creams as generally known in the art.

The compounds may also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, and polylactic acid. Methods for preparation of such formulations will be apparent to those skilled in the art. The materials may also be obtained commercially from Alza Corporation and Nova Pharmaceuticals, Inc. Liposomal suspensions (including liposomes targeted to infected cells with monoclonal antibodies to viral antigens) may also be used as pharmaceutically acceptable carriers. These may be prepared according to methods known to those skilled in the art, for example, as described in U.S. Pat. No. 4,522,811.

It is especially advantageous to formulate oral or parenteral compositions in dosage unit form for ease of administration and uniformity of dosage. "Dosage unit form" as used herein refers to physically discrete units suited as unitary dosages for the subject to be treated, each unit containing a predetermined quantity of active compound calculated to produce the desired therapeutic effect in association with the required pharmaceutical carrier. The specification for the dosage unit forms are dictated by and are directly dependent on the unique characteristics of the active compound and the particular therapeutic effect to be achieved, and the limitations inherent in the art of compounding such an active compound for the treatment of individuals.

EXAMPLES

Example 1. Production of the HPTPβ Extracellular Domain Protein

Methods: Full length HPTPβ is cloned from a human placental library according to the manufacturer's (Origene) instructions. The clone is identical to a previously reported cDNA clone (Genbank accession #X54131) except it is missing FNIII repeat #5. A cDNA encoding the entire soluble extracellular domain (ECD) of HPTPβ is cloned by PCR from the full length cDNA (see sequence below) coding for AA 1-1534 with an added c-terminal His-His-His-His-His-His-Gly (6His-Gly) (SEQ ID NO: 1). The resulting cDNA is cloned into mammalian expression vectors for transient (pShuttle-CMV) or stable (pcDNA3.1(−)) expression in HEK293 cells. To obtain purified HPTPβ ECD (βECD), HEK293 cells transfected with a βECD expression vector are incubated in OptiMEM-serum free (Gibco) for 24 hours under normal growth conditions. The conditioned media is then recovered, centrifuged to remove debris (1000 rpm×5 minutes), and 1 mL of washed Ni-NTA agarose (Qiagen) (500 µL packed material) is added to each 10 mL of cleared media and allowed to rock overnight at 4° C. On the following day, the mixture is loaded into a column and washed with 20 bed volumes of 50 mM NaH2PO4, 300 mM NaCl, 20 mM Imidazole, pH 8. The purified HPTPβ extracellular domain protein (SEQ ID NO: 2) is then eluted in six fractions with 200 µL/elution in 50 mM NaH2PO4, 300 mM NaCl, 250 mM Imidazole, pH 8. Fractions are analyzed for protein content using reducing-denaturing SDS-polyacrylimide gel electrophoresis and detected by silver stain (Invitrogen) and confirmed by mass spectrometry.

Results: To develop an antibody to the extracellular domain of HPTPβ, expression vectors directing the expression of a 6-His tagged HPTPβ extracellular domain protein (FIG. 1, Panel A) are developed. Subsequently, the 6-His tagged HPTPβ extracellular domain protein is purified to near homogeneity (FIG. 1, Panel B) from the conditioned media of HEK293 cells transfected with the expression vector.

Example 2. Generation of Monoclonal Antibodies to HPTPβ Extracellular Domain

Methods: For production of the HPTPβ extracellular domain immunogen, the purified HPTPβ extracellular domain-6His protein is conjugated to porcine thyroglobulin (Sigma) using EDC coupling chemistry (Hockfield, S. et al, (1993) Cold Spring Habor Laboratory Press. Volume 1 pp. 111-201, Immunocytochemistry). The resulting HPTPβ extracellular domain-thyroglobulin conjugate is dialyzed against PBS, pH 7.4. Adult Balb/c mice are then immunized subcutaneously with the conjugate (100-200 µg) and complete Freund's adjuvant in a 1:1 mixture. After 2-3 weeks, the mice are injected intraperitoneally or subcutaneously with incomplete Freund's adjuvant and the conjugate in a 1:1 mixture. The injection is repeated at 4-6 weeks. Sera are collected from mice 7 days post-third-injection and assayed for immunoreactivity to HPTPβ extracellular domain antigen by ELISA and western blotting. Mice that display a good response to the antigen are boosted by a single intra-spleen injection with 50 µl of purified HPTPβ extracellular domain protein mixed 1:1 with Alum hydroxide using a 31 gauge extra long needle (Goding, J. W., (1996) Monoclonal Antibodies: Principles and Practices. Third Edition, Academic Press Limited. p. 145). Briefly, mice are anesthetized with 2.5% avertin, and a 1 centimeter incision is created on the skin and left oblique body wall. The antigen mixture is administered by inserting the needle from the posterior portion to the anterior portion of the spleen in a longitudinal injection. The body wall is sutured and the skin is sealed with two small metal clips. Mice are monitored for safe recovery. Four days after surgery the mouse spleen is removed and single cell suspensions are made for fusion with mouse myeloma cells for the creation of hybridoma cell lines (Spitz, M., (1986) Methods In Enzymology, Volume 121. Eds. John J, Lagone and Helen Van Vunakis. PP. 33-41 (Academic Press, New York, N.Y.)). Resulting hybridomas are cultured in Dulbeccos modified media (Gibco) supplemented with 15% fetal calf serum (Hyclone) and hypoxanthine, aminopterin and thymidine.

Screening for positive hybridomas begins 8 days after the fusion and continues for 15 days. Hybridomas producing anti-HPTPβ extracellular domain antibodies are identified by ELISA on two sets of 96-well plates: one coated with the histidine tagged-HPTPβ extracellular domain and another one coated with a histidine-tagged bacterial MurA protein as a negative control. The secondary antibody is a donkey anti-mouse IgG labeled with horseradish peroxidase (HRP)

(Jackson Immunoresearch) Immunoreactivity is monitored in wells using color development initiated by ABTS tablets dissolved in TBS buffer, pH 7.5. The individual HRP reaction mixtures are terminated by adding 100 microliters of 1% SDS and reading absorbance at 405 nm with a spectrophotometer. Hybridomas producing antibodies that interact with HPTPβ extracellular domain-6His, and not with the murA-6His protein are used for further analysis. Limiting dilutions (0.8 cells per well) are performed twice on positive clones in 96 well plates, with clonality defined as having greater than 99% of the wells with positive reactivity. Isotypes of antibodies are determined using the iso-strip technology (Roche). To obtain purified antibody for further evaluation, tissue culture supernatants are affinity purified using a protein A or protein G columns.

Results: Five monoclonal antibodies immunoreactive to HPTPβ extracellular domain protein are isolated and given the following nomenclature, R15E6, R12A7, R3A2, R11C3, R15G2 and R5A8.

The monoclonal antibody R15E6 is deposited with American Type Culture Collection (ATCC), P.O. Box 1549, Manassas, Va. 20108 USA on 4 May 2006.

Example 3. R15E6 Binds to Endogenous HPTPβ on Human Endothelial Cells

A. R15E6 binds endogenous HPTPβ as demonstrated by immunoprecipitation and western blot.

Materials: Human umbilical vein endothelial cells (HUVECs), EGM media, and trypsin neutralizing solution from Cambrex; OPTIMEM I (Gibco), bovine serum albumin (BSA; Santa Cruz), phosphate buffered saline (PBS; Gibco), Growth Factors including Angiopoietin 1 (Ang1), vascular endothelial growth factor (VEGF) and fibroblast growth factor (FGF) (R&D Systems), Tie2 monoclonal antibody (Duke University/P&GP), VEGF receptor 2 (VEGFR2) polyclonal antibody (Whitaker et. al), protein A/G agarose (Santa Cruz), Tris-Glycine pre-cast gel electrophoresis/transfer system (6-8%) (Invitrogen), PVDF membranes (Invitrogen), lysis buffer (20 mm Tris-HCl, 137 mm NaCl, 10% glycerol, 1% triton-X-100, 2 mM EDTA, 1 mM NaOV, 1 mM NaF, 1 mM PMSF, 1 μg/ml leupeptin, 1 μg/ml pepstatin).

Method: HUVECs are pre-treated for 30 min with antibody (in OPTIMEM) or OPTIMEM I alone. After removal of pre-treatment, cells are treated with Ang1 (100 ng/ml) for 6 minutes in PBS+0.2% BSA and lysed in lysis buffer. Lysates are run directly on a Tris-Glycine gel or immunoprecipitated with 2-5 μg/ml Tie-2 antibody or 10 μg/ml R15E6 antibody and protein A/G agarose Immunoprecipitated samples are rinsed 1× with lysis buffer and boiled for 5 min in 1× sample buffer. Samples are resolved on a Tris-Glycine gel, transferred to a PVDF membrane, and detected by western blot using the indicated antibodies (pTYR Ab (PY99, Santa Cruz), Tie-2, VEGFR2 and/or R15E6).

Figure 2:
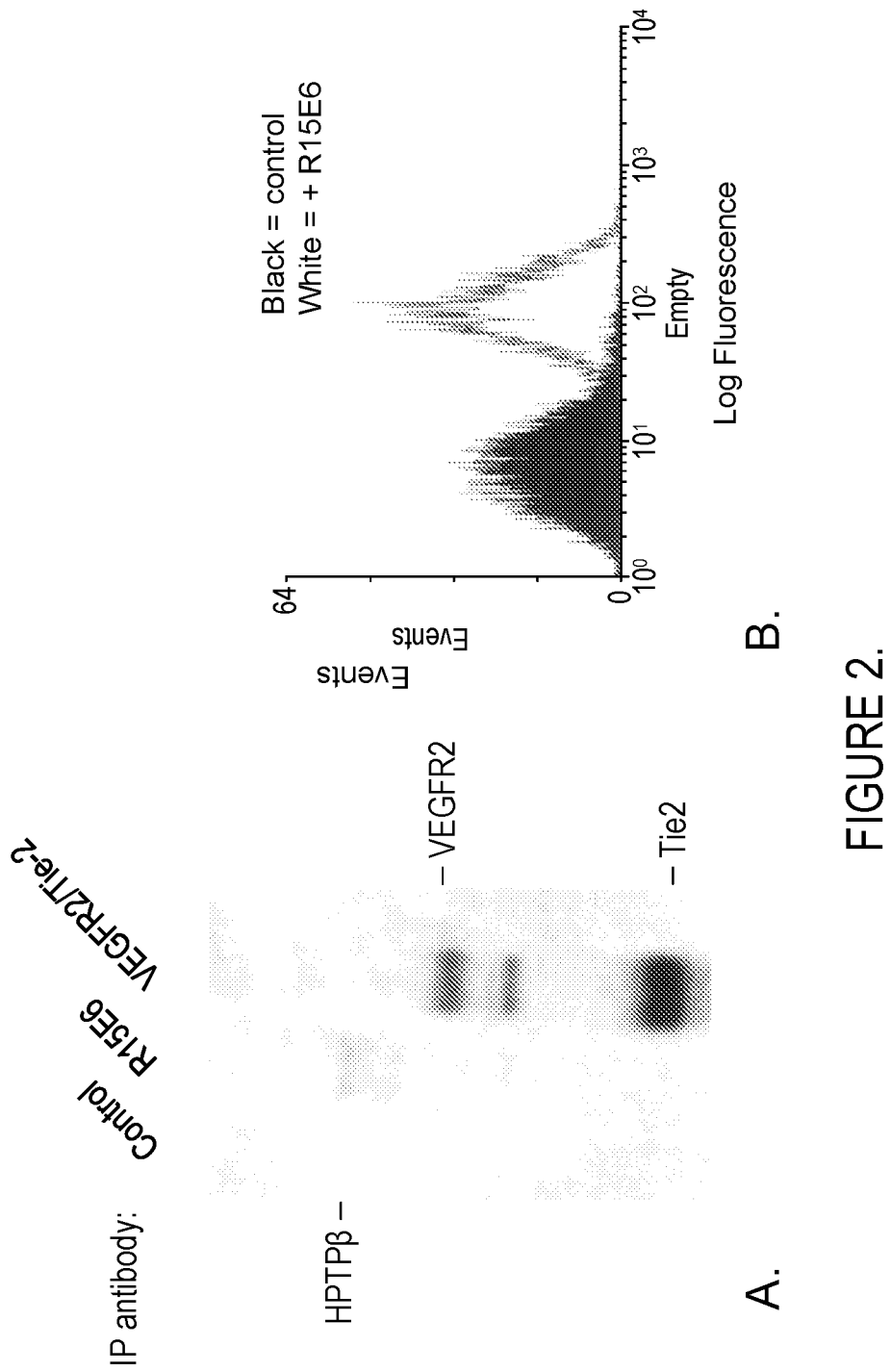
FIG. 2. R15E6 Recognizes Endogenous HPTPβ on Endothelial Cells. (Panel A) Endothelial cell lysates are immunoprecipitated with a control antibody (Lane 1), with R15E6 (Lane 2) or with a mixture of anti-Tie2 and anti-VEGFR2 antibodies (Lane 3). Immunoprecipitates are resolved by SDS-PAGE, transferred to a PVD membrane and probed by western blot with a mixture of R15E6, anti-Tie2 and anti-VEGFR2 antibodies. A single major high molecular weight band consistent with HPTPβ is seen with R15E6 (Lane 2) and not with the control antibody (Lane 1) or the mixture of anti-Tie2 and anti-VEGFR2 (Lane 3). (Panel B) Endothelial cells are subjected to FACS analysis with R15E6 (white peak) or a no primary antibody control (black peak). The robust shift in fluorescence indicates that R15E6 binds to HPTPβ on the surface of intact endothelial cells.

Results: By IP/western blotting, R15E6 recognizes a major, high molecular weight band consistent with the size of HPTPβ (FIG. 2, Panel A, Lane 2). The less intense, lower molecular weight bands likely represent less glycosylated precursor forms of HPTPβ. An immunoprecipitation (IP) with control, non-immune IgG shows no bands in the molecular weight range of HPTPβ (FIG. 2, Panel A, Lane 1), and a combined Tie2/VEGFR2 IP shows bands of the expected molecular weight (FIG. 2, Panel A, Lane 3). This result demonstrates that R15E6 recognizes and is specific for HPTPβ.

B. R15E6 binds endogenous HPTPβ as demonstrated by FACS analysis

Materials: HUVECs, EGM media, and trypsin neutralizing solution from Cambrex; Secondary Alexfluor 488-tagged antibody from Molecular Probes; Hanks balanced salt solution (Gibco); FACSCAN flow cytometer and CellQuest software from Becton Dickenson.

Method: HUVECs are trypsinized, treated with trypsin neutralizing solution and rinsed with HBSS. R15E6 antibody (0.6 μg) is added to 250,000 cells in 50 μL of HBSS and incubated on ice for 20 minutes. Cells are rinsed with 1 ml HBSS followed by adding 2 μg of fluorescent-conjugated secondary antibody for 20 minutes on ice. Cells are rinsed and resuspended in 1 ml HBSS then analyzed on the FACSCAN flow cytometer with CellQuest software. Control cells are treated with fluorescent-conjugated secondary antibody only.

Results: By FACS analysis, intact HUVECs, R15E6 causes a robust shift (>90% of cells) in the fluorescence signal compared to the secondary antibody alone (FIG. 2, Panel B). This result indicates that R15E6 binds to endogenous HPTPβ presented on the surface of intact endothelial cells.

Example 4. R15E6 Enhances Tie2 Activation, and Promotes Multiple Angiogenic Responses (Endothelial Cell Survival, Migration and Capillary Morphogenesis)

A. R15E6 enhances Tie2 phosphorylation in the absence and presence of the angiopoietin 1 (Ang1), the Tie2 ligand.

Methods: HUVECs are cultured in serum free media as described above in the presence or absence of various concentrations of R15E6 and with or without added Ang1. Lysates are prepared, immunoprecipitated with a Tie2 antibody, resolved by polyacrylamide gel electrophoresis and transferred to a PVDF membrane. Membrane-bound immunoprecipitated proteins are then serially western blotted with an antiphosphotyrosine antibody to quantify Tie2 phosphorylation followed by a Tie2 antibody to quantify total Tie2. Tie2 phosphorylation is expressed as the ratio of the antiphosphotyrosine signal over the total Tie2 signal.

Figure 3:
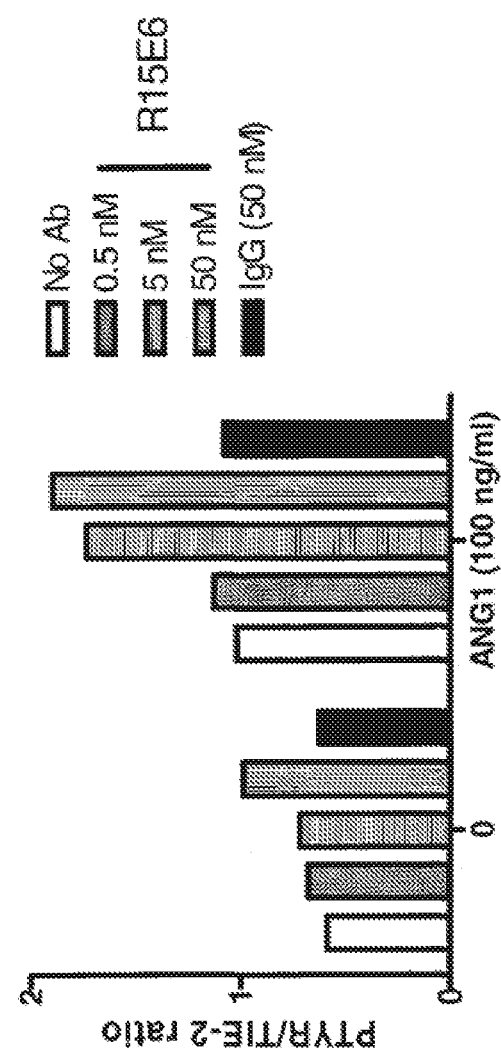
FIG. 3. R15E6 Enhances Tie2 Receptor Activation in HUVEC's. Tie2 activation is measured in human endothelial cells as described in Example 4. R15E6 dose dependently enhances both basal and Ang1-induced Tie2 activation.

Results: R15E6 enhances Tie2 phosphorylation both in the absence and presence of Ang1 (FIG. 3). This result indicates that binding of R15E6 to HPTPβ on the surface of endothelial cells modulates its biological function resulting in enhanced activation of Tie2 in the absence or presence of ligand.

B. R15E6 enhances endothelial cell survival in the absence and in the presence of endothelial growth factors.

Materials: HUVECs, EGM media, and trypsin neutralizing solution from Cambrex; DMEM (Cell Gro), Delipidized BSA (BD Falcon), Cell Titer Glo ATP Assay (Promega), Growth Factors (Ang1, VEGF 165, and FGF) (R&D Systems), Victor V Multilabel plate reader (Perkin Elmer Wallac).

Method: HUVECs are plated at 10,000 cells/well, serum starved in DMEM/0.2% BSA and treated for 72 h in the presence or absence of growth factor (Ang1, VEGF, or FGF), with or without various concentrations of R15E6 antibody. After 72 hours, the cells are rinsed with DMEM and surviving cells are quantified by measuring ATP levels using the Cell Titer Glo Luminescence Assay according to manufacturer's instructions (Promega).

Figure 4:
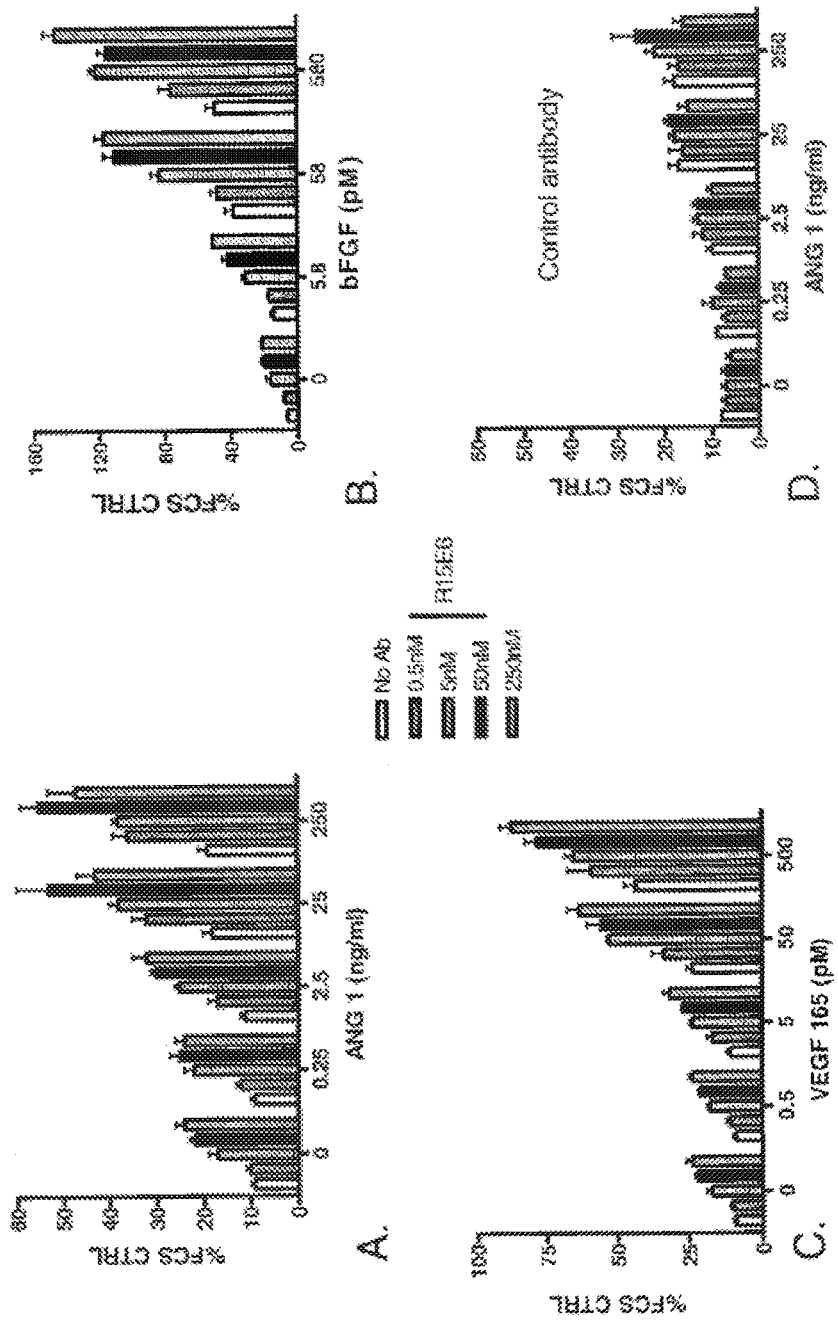
FIG. 4. R15E6 Enhances HUVEC Survival. Survival of serum starved human endothelial cells is measured as described in Example 4. Consistent with its effects on Tie2 activation, R15E6 dose dependently enhances both basal and Ang1-induced endothelial cell survival (Panel A). In addition, R15E6 also dose dependently enhances VEGF and FGF-mediated endothelial cell survival (Panels B and C). A control antibody fails to enhance endothelial cell survival (Panel D).

Results: Consistent with the results of the Tie2 activation assay, R15E6 enhances endothelial cell survival in the absence of added growth factor at concentrations between 0.5 and 5 nM (FIG. 4, Panel A). Similarly, R15E6 enhances Ang1 mediated endothelial cell survival (FIG. 4, Panel A) as well as cell survival mediated by VEGF and FGF (FIG. 4, Panels B and C). No enhanced survival is seen with a control monoclonal antibody (FIG. 4, Panel D). These results demonstrate that R15E6 binding to HPTPβ on the endothelial cell surface enhances baseline endothelial cell survival as well as cell survival mediated by multiple angiogenic pathways (Ang1, VEGF, and FGF).

C. R15E6 enhances endothelial cell migration in the absence and in the presence of VEGF.

Materials: HUVECs, EGM media, and trypsin neutralizing solution from Cambrex; EBM-phenol red free (PRF-EBM, Cambrex), Delipidized BSA (BD Falcon), BD Falcon Biocoat Endothelial Cell Migration system (BD Falcon), Calcein AM (Molecular Probes); Growth Factors (VEGF 165) (R&D Systems), Victor V Multilabel plate reader (Perkin Elmer Wallac).

Method: HUVECs are resuspended in PRF-EBM+0.1% BSA and plated at 50,000 cells/transwell (BD Bioscience, 3 μm pore size). Growth Factor/R15E6 is placed in the bottom well of the transwell chamber and incubated 4-22 h. Cells migrating through the membrane are detected by labeling with 4 μg/ml Calcein AM for 90'. Fluorescence is measured using a Victor V instrument (485/535).

Figure 5:
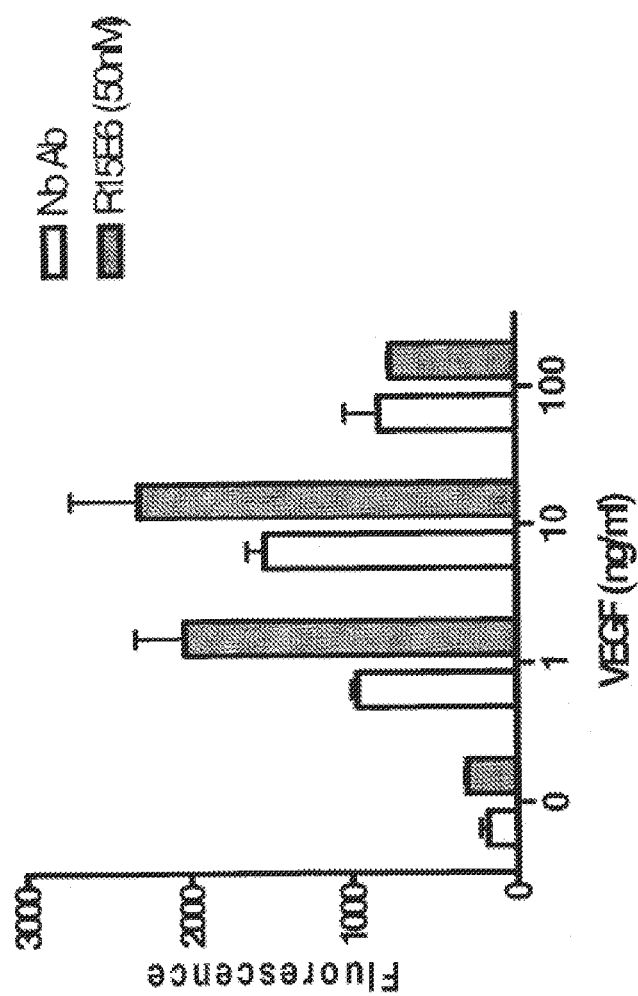
FIG. 5. R15E6 Enhances HUVEC Migration. Migration of human endothelial cells is measured as described in Example 4. R15E6 dose dependently enhances both basal and VEGF-induced endothelial cell migration.

Results: Consistent with the results in the survival study, R15E6 enhances both baseline and VEGF-mediated endothelial cell migration (FIG. 5).

D. R15E6 enhances endothelial cell sprouting and capillary morphogenesis in the absence and in the presence of endothelial growth factors.

Materials: HUVECs and EGM media from Cambrex; Cytodex beads and type I collagen from Sigma; Dulbecco's PBS and M199 media from Gibco; VEGF from R&D.

Method: HUVECs passage 4 ($2 \times 10^6$ cells) are cultured with 5 mg of Cytodex beads in 10 ml of EGM in 100 mm non-tissue culture treated bacteriological dishes for 48 hours with occasional swirling. Cell coated beads are transferred to a 50 ml conical tube and resuspended in 380 μl D-PBS. Collagen gels are prepared by adding 71.4 μl of cell coated beads to 2.8 ml of a matrix solution consisting of 3 mg/ml collagen in M199 media supplemented with 0.005 N NaOH, 20 mM HEPES, and 26 mM NaHCO$_3$. Three hundred and fifty microliters of the beads are dispensed into a well on a 24 well tissue culture plate and the matrix is allowed to solidify for 1 hour at 37° C./5% CO$_2$. One ml of EGM medium with or without VEGF (10 ng/ml) or R15E6 (7.5 μg/ml) is added per well and returned to the incubator. After 48 hours, a blinded observer visualizes the sprouts with a phase contrast inverted microscope and observes 50 beads per well, in triplicate wells, for the presence of endothelial cell sprouts. Results are expressed as the number of sprouts per bead.

Figure 6:
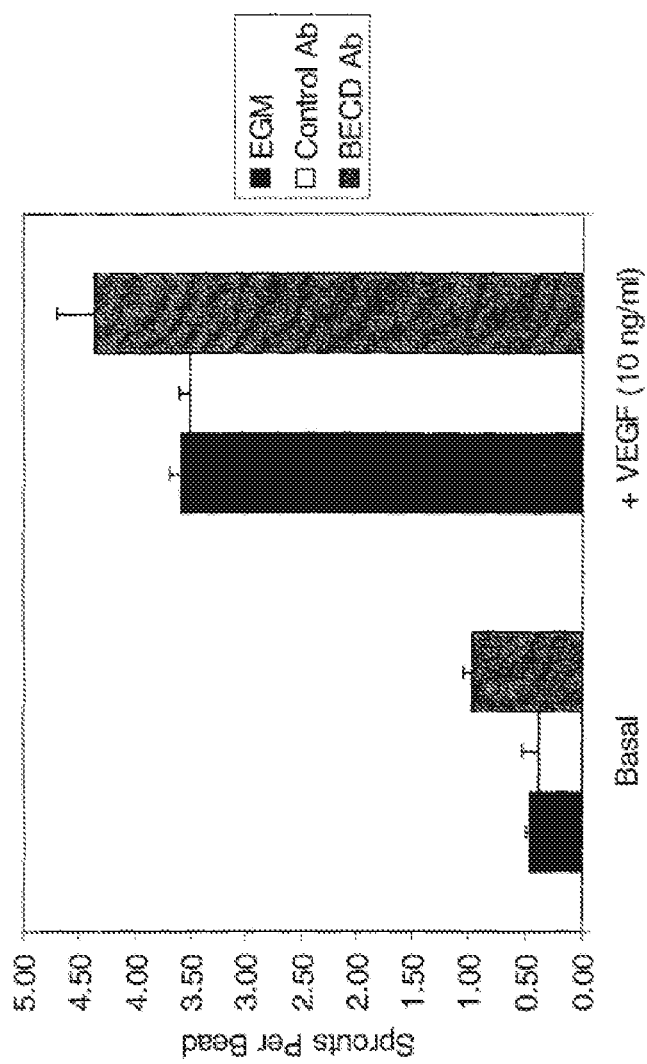
FIG. 6. R15E6 Enhances Capillary Morphogenesis in the HUVEC/Bead Sprouting Assay. Capillary morphogenesis of human endothelial cells is measured in the bead sprouting assay as described in Example 4. R15E6 enhances both basal and VEGF-induced endothelial cell capillary morphogenesis.

Results: Consistent with the results in the other assays, R15E6 also enhances baseline and VEGF mediated capillary morphogenesis in the endothelial bead sprouting assay (FIG. 6).

Example 5. The Binding Epitope for R15E6 is in the N-Terminal FN3 Repeat of the Human HPTPβ Extracellular Domain A. Western blot analysis of recombinant c-terminal truncation mutants and mouse/human chimeric proteins show that the R15E6 binding epitope is in the N-terminal FN3 repeat of the HPTPβ extracellular domain.

Methods: HEK293 cells are transfected with expression vectors encoding the indicated HPTPβ truncation mutant or mouse/human chimera. Transfected cells are then incubated in OptiMEM for an additional 24 hours after which conditioned media containing the indicated HPTPβ extracellular domain is harvested and either stored for future use or used immediately for western blot or ECL (see below) studies. For western blot analysis, 20 μl of conditioned media containing the indicated HPTPβ protein or no recombinant protein (Mock, empty vector transfected) is resolved by PAGE, transferred to a PVDF membrane and probed with R15E6.

Figure 7:
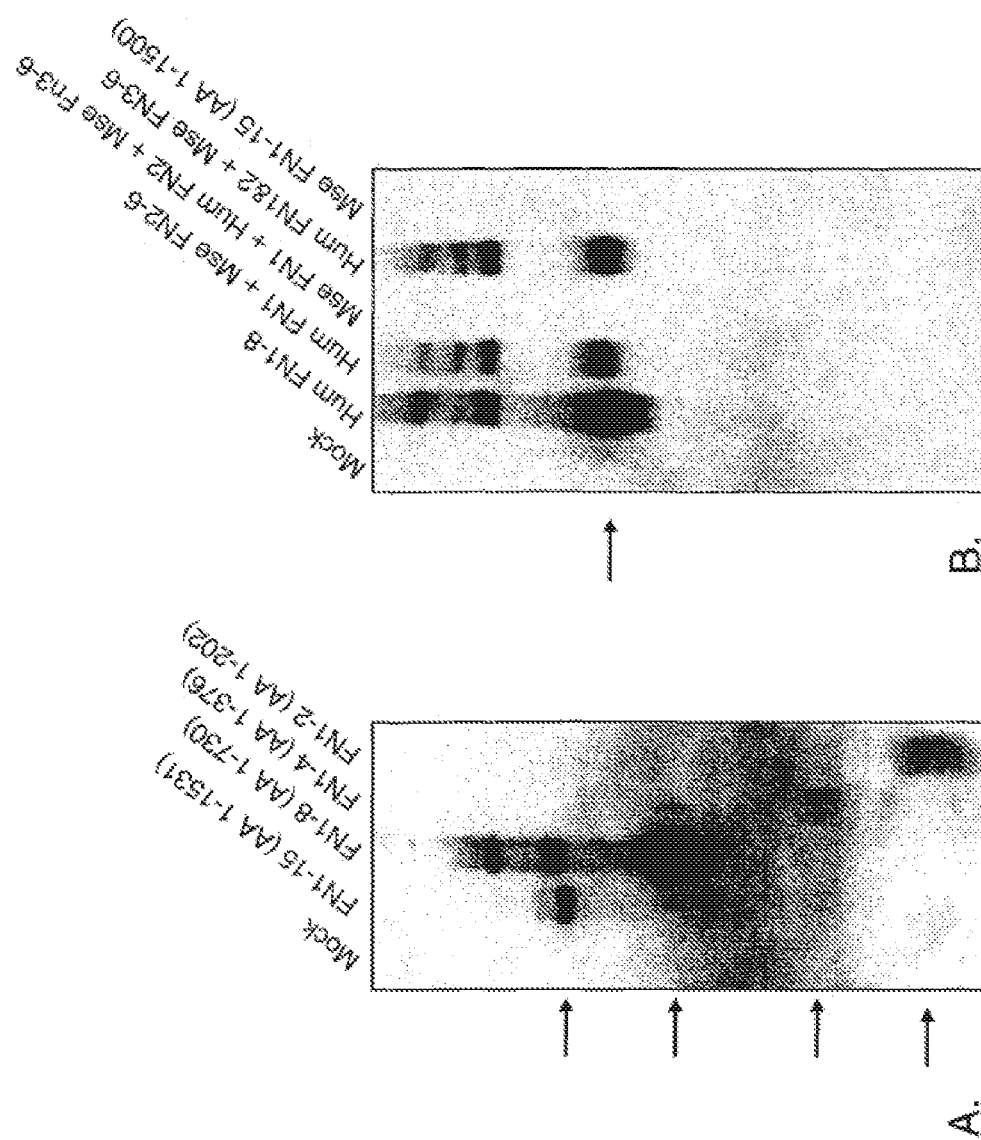
FIG. 7. Western blot analysis localizes the R15E6 binding epitope to the N-terminal FN3 repeat of the HPTPβ extracellular domain. (Panel A) By western analysis, R15E6 binds to all of the C-terminal truncation mutants demonstrating that the binding epitope is located in the N-terminal 2 FN3 repeats. (Panel B) Analysis of mouse/human chimeric proteins further localizes the R15E6 binding epitope to the HPTPβ N-terminal FN3 repeat.

Results: By western blot analysis, R15E6 binds all of the HPTPβ C-terminal deletion mutants (FIG. 7A) indicating that the binding epitope is within the first two N-terminal FN3 repeats. R15E6 fails to bind murine HPTPβ (SEQ ID NO: 7) extracellular domain demonstrating specificity for the human protein (FIG. 7B lane 6 vs. lane 2). Replacing the murine 1st or 1st and 2nd N-terminal FN3 repeats with the human sequences restored R15E6 binding (FIG. 7B lanes 3 and 5). Conversely, replacing only the murine 2nd FN3 repeat with the human sequence fails to restore binding (FIG. 7B lane 4). Taken together, these findings localize the binding epitope of R15E6 to the N-terminal FN3 repeat (~100 amino acids) of human HPTPβ.

B. ECL (electrochemiluminescent) analysis of -terminal truncation mutants and mouse/human chimeric proteins confirms that the R15E6 binding epitope is in the N-terminal FN3 repeat of the HPTPβ extracellular domain.

Methods: Supernatants containing the indicated HPTPβ protein are coated on a 96 well High bind MSD (Meso Scale Discovery) plate, allowed to dry, and blocked with 3% BSA for 1 h. The protein is then incubated with the R15E6 monoclonal antibody or the R15E6 Fab fragment (10 nM or 1.5 μg/ml) for 1 h, rinsed, and incubated with a goat anti-mouse antibody with an MSD-Tag label (10 nM) for 1 h. The excess antibody is rinsed off and MSD read buffer is added. Light emission is measured using the Sector 2400 reader (MSD). MSD utilizes electrochemiluminescent detection to detect binding events on patterned arrays. Meso Scale Discovery's technology uses proprietary MULTI-ARRAY™ and MULTI-SPOT™ microplates with electrodes integrated into the bottom of the plate. MSD's electrodes are made from carbon and biological reagents may be attached to the carbon simply by passive adsorption and retain a high level of biological activity. MSD assays use electrochemiluminescent labels for ultra-sensitive detection. These electrochemiluminescent labels emit light when electrochemically stimulated. The detection process is initiated at the built in electrodes located in the bottom of MSD's microplates and only labels near the electrode are excited and light detected at 620 nm.

Figure 8:
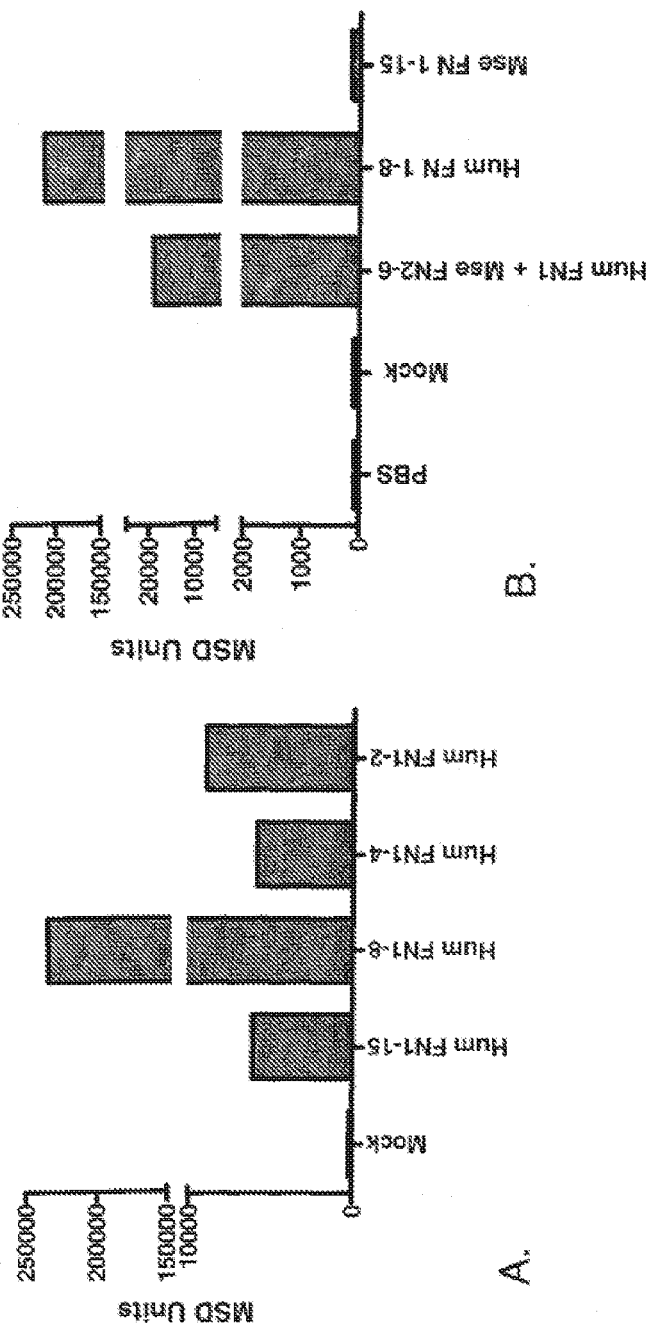
FIG. 8. MSD analysis confirms localization of the R15E6 binding epitope to the N-terminal FN3 repeat of the HPTPβ extracellular domain. (Panel A) By MSD analysis, R15E6 binds to all of the C-terminal truncation mutants confirming that the binding epitope is located in the N-terminal 2 FN3 repeats. (Panel B) Analysis of mouse/human chimeric proteins further confirms the localization of the R15E6 binding epitope to the HPTPβ N-terminal FN3 repeat.
Figure 9:
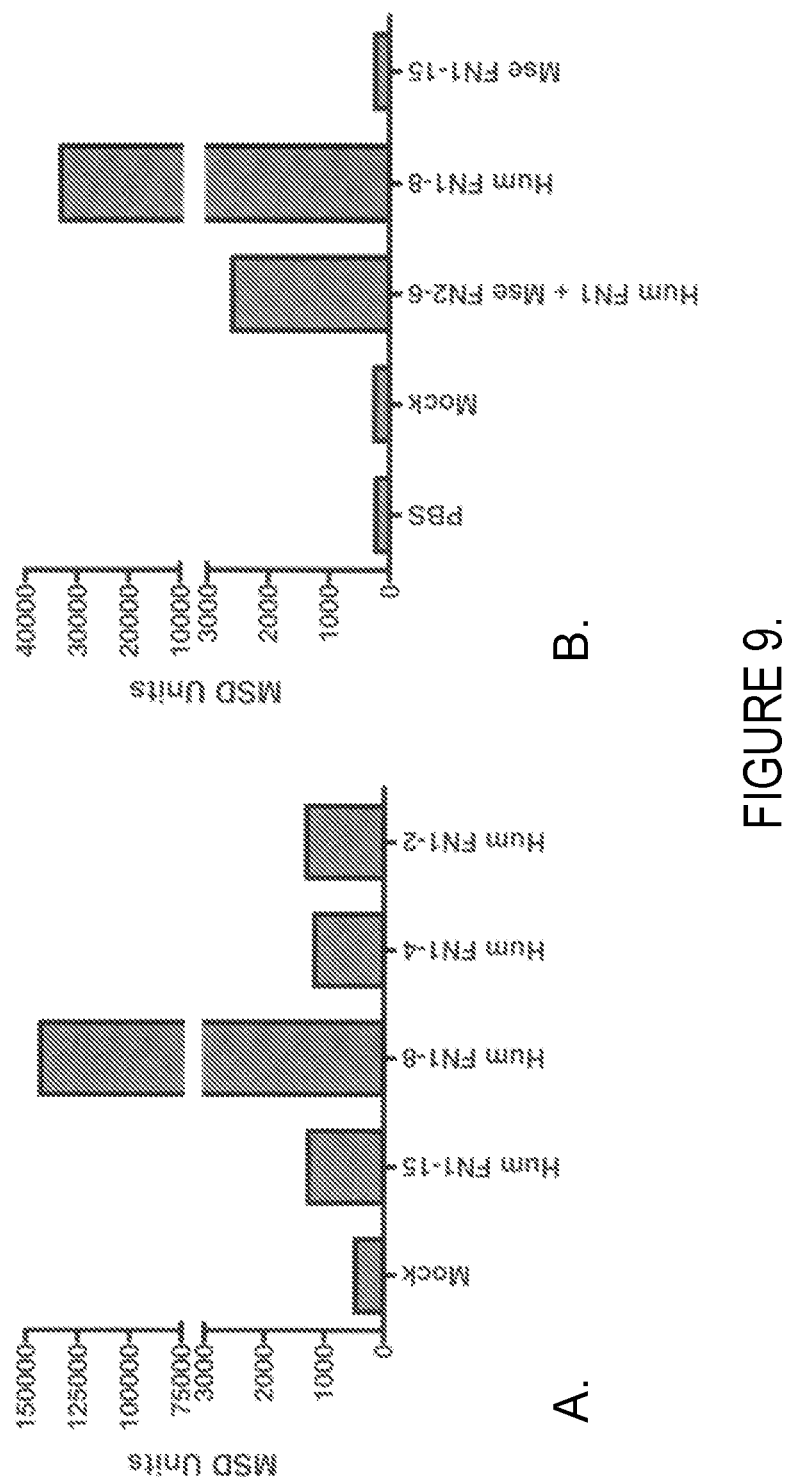
FIG. 9. MSD analysis demonstrates that the monovalent R15E6 Fab fragment also binds the N-terminal FN3 repeat of HPTPβ. (Panel A) Similar to the intact R15 E6 antibody, the R15E6 Fab fragment binds to all of the C-terminal truncation mutants confirming that the binding epitope is located in the N-terminal 2 FN3 repeats. (Panel B) Analysis of mouse/human chimeric proteins further localizes the binding epitope of the R15E6 Fab fragment to the HPTPβ N-terminal FN3 repeat.

Results: Consistent with the western blot studies, R15E6 binds to all of the HPTPβ C-terminal truncation proteins by MSD analysis (FIG. 8A). Also consistent with the western blot analysis, R15E6 fails to bind the murine HPTPβ extracellular domain but binding is restored by replacing the murine N-terminal FN3 repeat with the human N-terminal FN3 domain (FIG. 8B). These data confirm that the binding epitope of R15E6 is in the N-terminal FN3 repeat of human HPTPβ. As expected, the binding epitope of the monovalent R15E6 Fab fragment could also be mapped to the N-terminal most FN3 repeat of human HPTPβ (FIG. 9).

Example 6. A Monovalent R15E6 Fab Fragment Blocks R15E6 Mediated Tie2 Activation and Inhibits Endothelial Cell Survival and Migration Methods: Tie2 activation and endothelial cell survival and migration assays are performed as described above in example 4. Monovalent R15E6 Fab fragments are prepared as previously described. Purified R15E6 is dialyzed in 0.1M Tris-HCL, pH 8.0, containing 2 mM EDTA and 1 mM dithiothreitol. Papain (Pierce) at 1-2 mg/ml is activated in the aforementioned buffer for 15 minutes at 37° C. R15E6 at 10 mg/ml is incubated with papain in the same buffer using an enzyme:substrate ratio of 1:100, for 1 h at 37° C. The digestion is terminated by the addition of iodoacetamide (final concentration 20 mM, and held on ice for 1 h, protected from light. The papain digested material is dialyzed overnight against phosphate-buffered saline, to remove iodoacetamide. The extent of digestion is monitored by SDS-PAGE with the disappearance of the gamma heavy chain (MW 55,000 kDa) and the appearance of the Fc fragment of gamma (MW 27,000 kDa) and light chains (MW 22,000-25,000 kDa).

Figure 10:
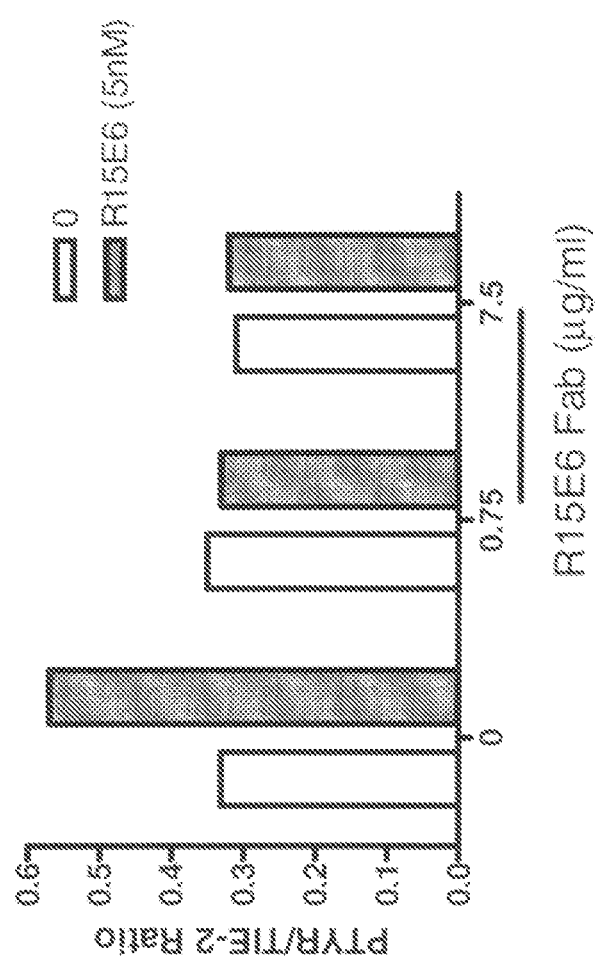
FIG. 10. The monovalent R15E6 Fab fragment fails to enhance Tie2 activation and blocks Tie2 activation by intact R15E6.
Figure 11:
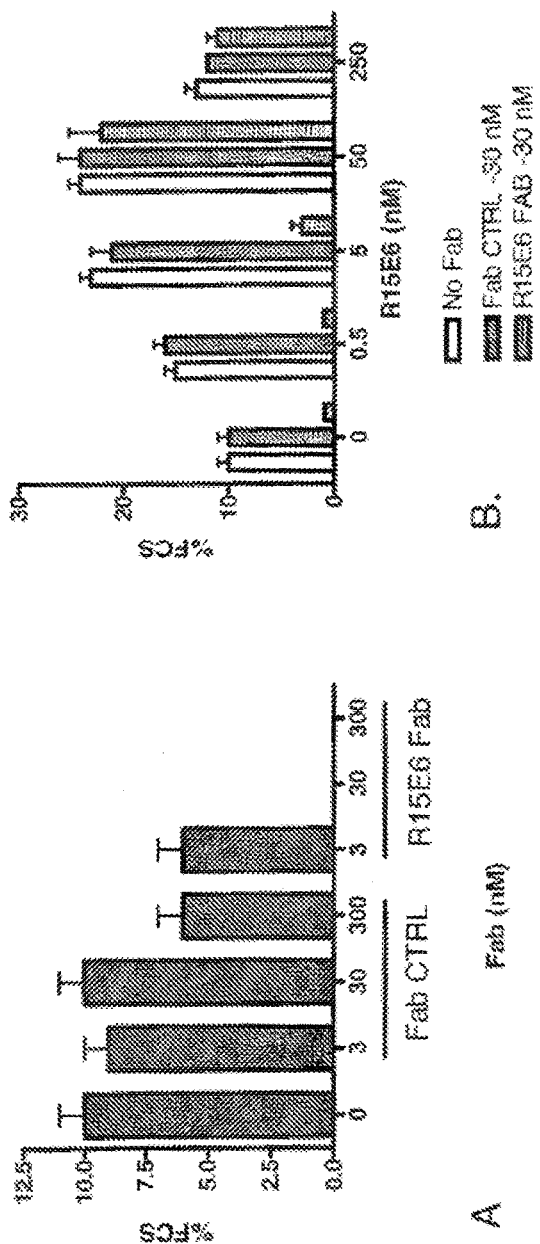
FIG. 11. The R15E6 Fab fragment potently inhibits endothelial cell survival. (Panel A) Compared to a control Fab fragment, the R15E6 Fab fragment potently inhibits endothelial cell survival. (Panel B) The inhibitory effect of the R15E6 Fab fragment is rescued by competition with intact R15E6.
Figure 12:
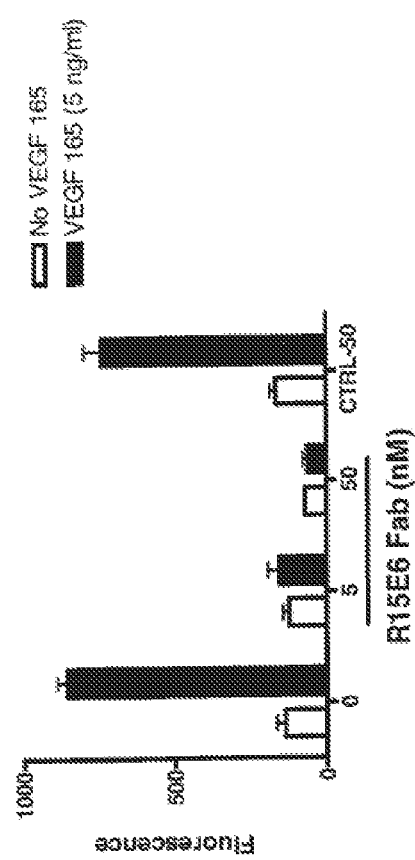
FIG. 12. The R15E6 Fab fragment inhibits VEGF mediated endothelial cell migration.

Results: Unlike the intact R15E6 antibody, the Fab fragments fails to enhance Tie2 activation (FIG. 10). Moreover, in the presence of excess Fab fragment, R15E6-mediated Tie2 activation is blocked (FIG. 10). Surprisingly, the R15E6 Fab fragment markedly inhibits endothelial cell survival compared to a control Fab (FIG. 11A) and this effect could be rescued by the addition of intact R15E6 (FIG. 11B). Consistent with the negative effect on endothelial survival, the R15E6 Fab also blocks VEGF mediated endothelial cell migration (FIG. 12). These findings demonstrate that the intact, dimeric R15E6 is required for the enhancement of angiogenic signaling and that monomeric R15E6 blocks these actions and actually has a negative effect on angiogenic endothelial cell responses.

Except as otherwise noted, all amounts including quantities, percentages, portions, and proportions, are understood to be modified by the word "about", and amounts are not intended to indicate significant digits.

Except as otherwise noted, the articles "a", "an", and "the" mean "one or more".

All documents cited are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications may be made without departing from the spirit and scope of the invention. It is therefore intended to cover in the appended claims all such changes and modifications that are within the scope of this invention.

What is claimed is:

1. An antibody or an antigen-binding fragment thereof that binds to human protein tyrosine phosphatase beta (HPTPβ), wherein the antibody or antigen-binding fragment thereof comprises antigen-binding region residues from an antibody produced by hybridoma cell line ATCC NO. PTA-7580 or a humanized form thereof, and wherein the antibody or antigen-binding fragment thereof enhances Tie-2 activation.

2. The antibody of claim 1, wherein the antibody or antigen-binding fragment thereof binds a FN3 repeat of HPTPβ.

3. The antibody of claim 1, wherein the antibody is a monoclonal antibody.

4. The antibody of claim 1, wherein the antibody is an antibody produced by hybridoma cell line ATCC NO. PTA-7580 or a humanized form thereof.

5. The antibody of claim 1, wherein the antibody or antigen-binding fragment thereof is humanized.

6. An antibody that binds to HPTPβ, wherein the antibody comprises antigen-binding region residues from an antibody produced by hybridoma cell line ATCC NO. PTA-7580 or a humanized form thereof, and wherein the antibody enhances Tie-2 activation.

7. The antibody of claim 6, wherein the antibody binds a FN3 repeat of HPTPβ.

8. The antibody of claim 6, wherein the antibody is a monoclonal antibody.

9. The antibody of claim 6, wherein the antibody is an antibody produced by hybridoma cell line ATCC NO. PTA-7580 or a humanized form thereof.

10. The antibody of claim 6, wherein the antibody is humanized.

* * * * *

UNITED STATES PATENT AND TRADEMARK OFFICE
CERTIFICATE OF CORRECTION

| | | |
|---|---|---|
| PATENT NO. | : 11,814,425 B2 | Page 1 of 1 |
| APPLICATION NO. | : 16/784970 | |
| DATED | : November 14, 2023 | |
| INVENTOR(S) | : Rotello et al. | |

It is certified that error appears in the above-identified patent and that said Letters Patent is hereby corrected as shown below:

On the Title Page

Column 1, Item (73), in "Assignee", Line 1, delete "Eye Point" and insert -- EyePoint --, therefor.

In the Specification

In Column 21, Line 50, delete "agarose" and insert -- agarose. --, therefor.

Signed and Sealed this
Twenty-second Day of October, 2024

*Katherine Kelly Vidal*

Katherine Kelly Vidal
*Director of the United States Patent and Trademark Office*